(12) United States Patent
Grund et al.

(10) Patent No.: US 12,714,509 B2
(45) Date of Patent: Aug. 25, 2026

(54) BIOSIGNAL-BASED NAVIGATION OF ELECTROPHYSIOLOGICAL MAPPING BASKETS USING STATISTICAL SHAPE MODELS

(71) Applicant: Boston Scientific Scimed, Inc., Maple Grove, MN (US)

(72) Inventors: Alessa Tabea Grund, Munich (DE); Stefan Marcel Denner, Munich (DE); David Emanuel Luksic, Munich (DE); Philip Haeusser, Munich (DE); Peter Ruppersberg, Blonay (CH); Kostiantyn Serhiyovich Ahapov, Munich (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 507 days.

(21) Appl. No.: 18/125,630

(22) Filed: Mar. 23, 2023

(65) Prior Publication Data

US 2023/0225800 A1 Jul. 20, 2023

Related U.S. Application Data

(63) Continuation-in-part of application No. 17/863,246, filed on Jul. 12, 2022, and a continuation-in-part of application No. 17/831,249, filed on Jun. 2, 2022.

(Continued)

(51) Int. Cl.

*A61B 34/20* (2016.01)
*A61B 5/00* (2006.01)

(Continued)

(52) U.S. Cl.

CPC .............. *A61B 34/20* (2016.02); *A61B 5/287* (2021.01); *A61B 5/339* (2021.01); *A61B 5/367* (2021.01);

(Continued)

(58) Field of Classification Search

None

See application file for complete search history.

(56) References Cited

U.S. PATENT DOCUMENTS 930,236 A 8/1909 Schacht
987,217 A 3/1911 Connor et al.

(Continued)

FOREIGN PATENT DOCUMENTS

CN 111655130 A 9/2020
EP 2586363 A1 5/2013

(Continued)

OTHER PUBLICATIONS

Intention to grant received for European Patent Application No. 21202891.4, mailed on May 26, 2025, 6 pages.

(Continued)

*Primary Examiner* — Kennedy Schaetzle

(74) *Attorney, Agent, or Firm* — Nelson Mullins Riley & Scarborough LLP

(57) ABSTRACT

In some embodiments, there are provided systems, devices, components, and corresponding methods configured to permit navigation and/or positioning of an intra-cardiac electrophysiological (EP) mapping basket or other EP mapping structure of an EP mapping catheter inside or near an atrium or other heart chamber of a patient's heart using biosignals or intra-cardiac signals. In one embodiment, QRS complexes are extracted or isolated from intra-cardiac signals sensed by electrodes mounted on the EP mapping basket. Using the QRS complexes and a statistical shape or other model of the EP mapping basket or other type of EP mapping structure, one or more computing devices then determine the locations of the electrodes inside or near the patient's atrium that are associated with each isolated or extracted QRS complex, and thereby permit accurate navigation within the heart and/or processing of data acquired (Continued)

400

Recording and/or Acquiring Intra-Cardiac Signals using an EP Mapping Catheter having an EP Mapping Basket or Other Mapping Structure — 401

Isolating and/or Extracting Ventricular Signals From the Intra-Cardiac Signals — 403

Determining a Shape Model of the EP Mapping Basket or Other Mapping Structure — 405

Determining the Locations of Electrodes Inside the Patient's Heart on the EP Mapping Basket or Other Mapping Structure — 407 using the EP mapping basket or other EP mapping structure. The one or more computing devices can also be used to determine changes in the three-dimensional locations and orientations of the basket and the electrodes thereof as the EP mapping basket is moved around, in, or near the patient's atrium, heart chamber, or other portion of the patient's heart, and to display to a user multiple positions of the basket inside or near the patient's heart.

28 Claims, 36 Drawing Sheets
(29 of 36 Drawing Sheet(s) Filed in Color)

Related U.S. Application Data

(60) Provisional application No. 63/323,163, filed on Mar. 24, 2022, provisional application No. 63/222,346, filed on Jul. 15, 2021, provisional application No. 63/221,291, filed on Jul. 13, 2021, provisional application No. 63/196,605, filed on Jun. 3, 2021.

(51) Int. Cl.
*A61B 5/287* (2021.01)
*A61B 5/339* (2021.01)
*A61B 5/367* (2021.01)

(52) U.S. Cl.
CPC .... *A61B 5/6858* (2013.01); *A61B 2034/2072* (2016.02)

(56) References Cited

U.S. PATENT DOCUMENTS 1,684,880 A 9/1928 Norton
1,972,114 A 9/1934 Stephenson
2,042,372 A 5/1936 Watson
2,056,018 A 9/1936 Popp
4,186,451 A 2/1980 Ruo
4,622,702 A 11/1986 Allen
4,745,641 A 5/1988 Tash
5,172,699 A 12/1992 Svenson et al.
5,239,708 A 8/1993 Irwin
5,271,411 A 12/1993 Ripley et al.
5,383,917 A 1/1995 Desai et al.
5,427,112 A 6/1995 Noren et al.
5,433,196 A 7/1995 Fiat
5,433,198 A 7/1995 Desai
5,450,846 A 9/1995 Goldreyer
5,480,422 A 1/1996 Ben-Haim
5,487,391 A 1/1996 Panescu
5,549,108 A 8/1996 Edwards et al.
5,582,173 A 12/1996 Li
5,595,183 A 1/1997 Swanson et al.
5,609,158 A 3/1997 Chan
5,617,134 A 4/1997 Lamothe
5,657,755 A 8/1997 Desai
5,662,108 A 9/1997 Budd et al.
5,687,737 A 11/1997 Branham et al.
5,718,241 A 2/1998 Ben-Haim et al.
5,752,518 A 5/1998 McGee et al.
5,795,303 A 8/1998 Swanson et al.
5,817,134 A 10/1998 Greenhut et al.
5,840,025 A 11/1998 Ben-Haim
5,848,972 A 12/1998 Triedman et al.
5,868,680 A 2/1999 Steiner et al.
5,954,665 A 9/1999 Ben-Haim
6,052,618 A 4/2000 Dahlke et al.
6,066,094 A 5/2000 Ben-Haim
6,067,668 A 5/2000 Rudd
6,115,628 A 9/2000 Stadler et al.
6,188,924 B1 2/2001 Swanson et al.
6,236,883 B1 5/2001 Ciaccio et al.
6,256,540 B1 7/2001 Panescu et al.
6,301,496 B1 10/2001 Reisfeld
6,360,121 B1 3/2002 Shoda et al.
6,393,626 B1 5/2002 Dhillon
6,434,760 B1 8/2002 Montalvo
6,480,615 B1 11/2002 Sun et al.
6,480,815 B1 11/2002 Olson et al.
6,522,905 B2 2/2003 Desai
6,550,074 B1 4/2003 Allenbaugh et al.
6,584,345 B2 6/2003 Govari
6,684,417 B1 2/2004 Schneider
6,725,085 B2 4/2004 Schwartzman et al.
6,847,839 B2 1/2005 Ciaccio et al.
6,856,830 B2 2/2005 He
6,892,091 B1 5/2005 Ben-Haim et al.
6,920,350 B2 7/2005 Xue et al.
6,941,166 B2 9/2005 Macadam et al.
6,959,212 B2 10/2005 Hsu et al.
6,975,900 B2 12/2005 Rudy et al.
6,978,168 B2 12/2005 Beatty et al.
7,016,719 B2 3/2006 Rudy et al.
7,043,292 B2 5/2006 Tarjan et al.
7,081,114 B2 7/2006 Rashidi
7,117,030 B2 10/2006 Berenfeld et al.
7,123,954 B2 10/2006 Narayan et al.
7,206,630 B1 4/2007 Tarler
7,245,962 B2 7/2007 Ciaccio et al.
7,263,397 B2 8/2007 Hauck et al.
7,283,665 B2 10/2007 Suzuki
7,283,865 B2 10/2007 Kjell
7,289,843 B2 10/2007 Beatty et al.
7,328,063 B2 2/2008 Zhang et al.
7,340,783 B2 3/2008 Leaphart et al.
7,505,810 B2 3/2009 Harlev et al.
7,515,954 B2 4/2009 Harlev et al.
7,736,785 B2 6/2010 Oda et al.
7,751,882 B1 7/2010 Helland
7,761,142 B2 7/2010 Ghanem et al.
7,761,150 B2 7/2010 Ghanem et al.
7,907,994 B2 3/2011 Stolarski et al.
7,930,018 B2 4/2011 Harlev et al.
7,930,020 B2 4/2011 Zhang et al.
8,048,063 B2 11/2011 Aeby et al.
8,150,502 B2 4/2012 Kumar et al.
8,160,682 B2 4/2012 Kumar et al.
8,165,666 B1 4/2012 Briggs et al.
8,165,671 B2 4/2012 Freeman et al.
8,175,702 B2 5/2012 Efimov et al.
8,244,335 B2 8/2012 Kumar et al.
8,521,266 B2 8/2013 Narayan et al.
8,538,503 B2 9/2013 Kumar et al.
8,560,046 B2 10/2013 Kumar et al.
8,594,777 B2 11/2013 Briggs et al.
8,639,325 B2 1/2014 Efimov et al.
8,647,284 B2 2/2014 Afonso
8,676,303 B2 3/2014 Narayan
8,700,140 B2 4/2014 Narayan et al.
8,838,222 B2 9/2014 Narayan et al.
8,838,223 B2 9/2014 Narayan et al.
8,852,130 B2 10/2014 Govari
8,868,169 B2 10/2014 Narayan et al.
8,911,917 B2 12/2014 Sato et al.
9,050,006 B2 6/2015 Narayan et al.
9,055,877 B2 6/2015 Narayan et al.
9,055,878 B2 6/2015 Narayan et al.
9,089,269 B2 7/2015 Narayan et al.
9,107,600 B2 8/2015 Narayan et al.
9,173,670 B2 11/2015 Sepulveda et al.
9,220,427 B2 12/2015 Narayan et al.
9,236,883 B2 1/2016 Guha
9,241,649 B2 1/2016 Kumar et al.
9,241,667 B2 1/2016 Narayan et al.
9,282,910 B2 3/2016 Narayan et al.
9,332,915 B2 5/2016 Narayan et al.
9,392,948 B2 7/2016 Briggs et al.
9,398,883 B2 7/2016 Narayan et al.
9,408,536 B2 8/2016 Narayan et al.
9,451,975 B2 9/2016 Sepulveda et al.
9,474,491 B2 10/2016 Li et al.

(56) References Cited

U.S. PATENT DOCUMENTS 9,597,004 B2 3/2017 Hughes et al.
9,642,674 B2 5/2017 Chmiel et al.
9,730,603 B2 8/2017 Laughner et al.
9,808,171 B2 11/2017 Balachandran et al.
9,872,653 B2 1/2018 Li et al.
9,955,887 B2 5/2018 Hughes et al.
10,098,559 B2 10/2018 Hughes et al.
10,123,703 B2 11/2018 Bardy et al.
10,136,828 B2 11/2018 Houben et al.
10,143,374 B2 12/2018 Ruppersberg
10,201,277 B2 2/2019 Ruppersberg
10,221,551 B2 3/2019 Gray
10,271,754 B2 4/2019 Bahney et al.
10,299,691 B2 5/2019 Hughes et al.
D852,965 S 7/2019 Bahney et al.
10,362,952 B2 7/2019 Basu et al.
10,362,953 B2 7/2019 Basu
10,517,500 B2 12/2019 Kumar et al.
10,772,522 B2 9/2020 Zadig
10,806,343 B2 10/2020 Ruppersberg
10,820,800 B2 11/2020 Ruppersberg
10,888,236 B2 1/2021 Ruppersberg
10,980,418 B2 4/2021 Ruppersberg
11,291,395 B2 4/2022 Ruppersberg
11,389,102 B2 7/2022 Haeusser et al.
2001/0037522 A1 11/2001 Pool et al.
2001/0056245 A1 12/2001 Mlynash et al.
2002/0010392 A1 1/2002 Desai
2002/0016548 A1 2/2002 Stadler et al.
2002/0151808 A1 10/2002 Schwartzman et al.
2003/0036696 A1 2/2003 Willis et al.
2003/0079278 A1 5/2003 Tash
2003/0236466 A1 12/2003 Tarjan et al.
2004/0073262 A1 4/2004 Lovett
2004/0133113 A1 7/2004 Krishnan
2004/0243011 A1 12/2004 Plaza
2005/0148892 A1 7/2005 Desai
2005/0182336 A1 8/2005 Sippens Groenewegen
2005/0203502 A1 9/2005 Boveja et al.
2006/0084870 A1 4/2006 Kim et al.
2006/0084970 A1 4/2006 Beatty et al.
2006/0093891 A1 5/2006 Issacci et al.
2006/0111700 A1 5/2006 Kunis et al.
2006/0161069 A1 7/2006 Li
2006/0161206 A1 7/2006 Efimov et al.
2007/0055167 A1 3/2007 Bullinga
2007/0073179 A1 3/2007 Afonso et al.
2007/0208260 A1 9/2007 Afonso
2007/0219454 A1 9/2007 Guzzetta et al.
2007/0299351 A1 12/2007 Harlev et al.
2008/0009758 A1 1/2008 Voth
2008/0051704 A1 2/2008 Patel et al.
2008/0097539 A1 4/2008 Belalcazar
2008/0109041 A1 5/2008 De Voir
2008/0114258 A1 5/2008 Zhang et al.
2008/0161669 A1 7/2008 Hauck et al.
2008/0193308 A1 8/2008 Korcoban
2008/0245955 A1 10/2008 Tachi et al.
2008/0275367 A1 11/2008 Barbagli et al.
2009/0069704 A1 3/2009 MacAdam et al.
2009/0099468 A1 4/2009 Thiagalingam et al.
2009/0112106 A1 4/2009 Zhang
2009/0112110 A1 4/2009 Zhang
2009/0112199 A1 4/2009 Zhang et al.
2009/0171274 A1 7/2009 Harlev et al.
2009/0177071 A1 7/2009 Harlev et al.
2009/0177072 A1 7/2009 Harlev et al.
2009/0177095 A1 7/2009 Aeby et al.
2009/0275828 A1 11/2009 Shachar et al.
2009/0299424 A1 12/2009 Narayan
2010/0000357 A1 1/2010 Gutmann et al.
2010/0030063 A1* 2/2010 Lee .......................... A61B 5/06 600/424
2010/0035122 A1 2/2010 Yamamoto et al.
2010/0058519 A1 3/2010 Davenport
2010/0094274 A1 4/2010 Narayan et al.
2010/0129694 A1 5/2010 Sugiura et al.
2010/0204592 A1 8/2010 Hatib et al.
2010/0217143 A1 8/2010 Whittington et al.
2010/0249627 A1 9/2010 Zhang et al.
2010/0280402 A1 11/2010 Dunbar et al.
2010/0298729 A1 11/2010 Zhang et al.
2010/0305456 A1 12/2010 Brainard, II
2011/0087121 A1 4/2011 Zhang et al.
2011/0112425 A1 5/2011 Muhlsteff et al.
2011/0130801 A1 6/2011 Maskara et al.
2011/0196249 A1 8/2011 Staeuber et al.
2011/0213231 A1 9/2011 Hall et al.
2011/0219526 A1 9/2011 Keegan
2011/0251505 A1 10/2011 Narayan et al.
2011/0257547 A1 10/2011 Zhang
2011/0270046 A1 11/2011 Paul et al.
2011/0282227 A1 11/2011 Zhang
2012/0009502 A1 1/2012 Darling et al.
2012/0011643 A1 1/2012 Schultz
2012/0129071 A1 5/2012 Sato et al.
2012/0129073 A1 5/2012 Spencer et al.
2012/0232417 A1 9/2012 Zhang
2012/0233757 A1 9/2012 Slot
2012/0238889 A1 9/2012 Yu et al.
2012/0247519 A1 10/2012 Dondurur et al.
2012/0271135 A1 10/2012 Burke et al.
2012/0283590 A1 11/2012 Afonso
2012/0321987 A1 12/2012 Goto et al.
2013/0006131 A1 1/2013 Narayan et al.
2013/0102868 A1 4/2013 Fandrey et al.
2013/0150740 A1 6/2013 Narayan et al.
2013/0150742 A1 6/2013 Briggs et al.
2013/0204142 A1 8/2013 Bertholds et al.
2013/0220032 A1 8/2013 Packirisamy et al.
2013/0226016 A1 8/2013 Narayan et al.
2013/0245476 A1 9/2013 Takizawa et al.
2013/0331718 A1 12/2013 Narayan et al.
2013/0337359 A1 12/2013 Sugiura et al.
2014/0066787 A1 3/2014 Narayan et al.
2014/0073981 A1 3/2014 Narayan et al.
2014/0088395 A1 3/2014 Dubois et al.
2014/0114204 A1 4/2014 Narayan et al.
2014/0209797 A1 7/2014 Klimovitch
2014/0228696 A1 8/2014 Narayan et al.
2014/0276152 A1 9/2014 Narayan et al.
2014/0343388 A1 11/2014 Thakur et al.
2014/0364848 A1 12/2014 Heimbecher et al.
2015/0057522 A1 2/2015 Nguyen et al.
2015/0065836 A1 3/2015 Thakur et al.
2015/0073246 A1 3/2015 Chmiel et al.
2015/0104729 A1 4/2015 Ishida et al.
2015/0105645 A1 4/2015 Subramaniam et al.
2015/0126840 A1 5/2015 Thakur et al.
2015/0126993 A1 5/2015 Gelbart et al.
2015/0164349 A1 6/2015 Gopalakrishnan et al.
2015/0208937 A1 7/2015 Bullinga
2015/0216438 A1 8/2015 Bokan et al.
2015/0250424 A1 9/2015 Govari et al.
2015/0254419 A1 9/2015 Laughner et al.
2015/0273541 A1 10/2015 Kim
2015/0289781 A1 10/2015 Grunwald et al.
2015/0313491 A1 11/2015 Edwards et al.
2015/0350502 A1 12/2015 Lin
2016/0000357 A1 1/2016 Harlev et al.
2016/0073960 A1 3/2016 Jung et al.
2016/0184028 A1 6/2016 Warner et al.
2016/0374582 A1 12/2016 Wu et al.
2017/0018205 A1 1/2017 Santhanam et al.
2017/0022694 A1 1/2017 Broten
2017/0027465 A1 2/2017 Blauer et al.
2017/0035497 A1 2/2017 Nagale et al.
2017/0065198 A1 3/2017 Ruppersberg
2017/0164858 A1 6/2017 Basu
2017/0178403 A1 6/2017 Krummen et al.
2017/0202471 A1 7/2017 Urman et al.
2017/0202515 A1 7/2017 Zrihem et al.
2017/0202521 A1 7/2017 Urman et al.
2017/0303807 A1 10/2017 Laughner et al.

(56) References Cited

U.S. PATENT DOCUMENTS

| | | | | |
|---|---|---|---|---|
| 2018/0342072 | A1 | 11/2018 | Raudins | |
| 2019/0125186 | A1 | 5/2019 | Ruppersberg | |
| 2019/0142271 | A1 | 5/2019 | Ruppersberg | |
| 2019/0284757 | A1 | 9/2019 | Chopra et al. | |
| 2019/0329302 | A1 | 10/2019 | Wu | |
| 2019/0357793 | A1 | 11/2019 | Ruppersberg | |
| 2020/0024839 | A1 | 1/2020 | Tapper | |
| 2020/0046245 | A1 | 2/2020 | Qu et al. | |
| 2020/0240127 | A1 | 7/2020 | Tash | |
| 2020/0245885 | A1 | 8/2020 | Haeusser et al. | |
| 2020/0345261 | A1 | 11/2020 | Haeusser et al. | |
| 2021/0000369 | A1 | 1/2021 | Luksic et al. | |
| 2021/0068694 | A1 | 3/2021 | Chou et al. | |
| 2021/0259765 | A1 | 8/2021 | Narayan | |
| 2021/0282693 | A1 | 9/2021 | Ruppersberg et al. | |
| 2021/0393187 | A1 | 12/2021 | Amos et al. | |
| 2022/0245885 | A1 | 8/2022 | Pags et al. | |
| 2022/0345261 | A1 | 10/2022 | Ali et al. | |
| 2022/0387099 | A1 | 12/2022 | Cohen et al. | |
| 2024/0033008 | A1* | 2/2024 | Govari | A61B 5/367 |

FOREIGN PATENT DOCUMENTS

| | | | |
|---|---|---|---|
| EP | 2638852 | A1 | 9/2013 |
| EP | 2641557 | A1 | 9/2013 |
| EP | 3192445 | A1 | 7/2017 |
| EP | 3346914 | A1 | 7/2018 |
| EP | 3346915 | A1 | 7/2018 |
| EP | 3375365 | A2 | 9/2018 |
| EP | 3192438 | B1 | 8/2019 |
| EP | 3556284 | A3 | 12/2019 |
| EP | 3686899 | A1 | 7/2020 |
| EP | 3747356 | A1 | 12/2020 |
| EP | 3918998 | A1 | 12/2021 |
| EP | 3984457 | A1 | 4/2022 |
| EP | 4029449 | A1 | 7/2022 |
| EP | 4098198 | A2 | 12/2022 |
| EP | 4119054 | A1 | 1/2023 |
| EP | 23164010 | | 7/2023 |
| ES | 2706537 | A1 | 3/2019 |
| JP | 63-270026 | A | 11/1988 |
| JP | 2012-164467 | A | 8/2012 |
| WO | WO 01/67950 | A1 | 9/2001 |
| WO | 2012/092016 | A1 | 7/2012 |
| WO | 2012/173697 | A1 | 12/2012 |
| WO | 2013/106559 | A2 | 7/2013 |
| WO | 2014/007871 | A1 | 1/2014 |
| WO | 2014/036439 | A2 | 3/2014 |
| WO | 2014/124231 | A1 | 8/2014 |
| WO | 2014/168987 | A1 | 10/2014 |
| WO | 2015/000870 | A1 | 1/2015 |
| WO | 2015/001097 | A1 | 1/2015 |
| WO | 2015/066678 | A2 | 5/2015 |
| WO | 2015/113770 | A1 | 8/2015 |
| WO | 2015/120961 | A1 | 8/2015 |
| WO | 2015/130824 | A1 | 9/2015 |
| WO | 2016/077786 | A1 | 5/2016 |
| WO | 2017/041892 | A1 | 3/2017 |
| WO | 2017/042623 | A1 | 3/2017 |
| WO | 2017/125114 | A1 | 7/2017 |
| WO | 2019/063861 | A1 | 4/2019 |

OTHER PUBLICATIONS

International Preliminary Report on Patentability received for PCT application No. PCT/EP2016/001513, mailed on Mar. 22, 2018, 12 pages.

International Preliminary Report on Patentability received for PCT application No. PCT/EP2016/001514, mailed on Mar. 22, 2018, 10 pages.

International Preliminary Report on Patentability received for PCT Patent Application No. PCT/EP2016/000087, mailed on Aug. 2, 2018, 9 pages.

International Preliminary Report on Patentability received for PCT Patent Application No. PCT/EP2016/000870, mailed on Dec. 14, 2017, 8 pages.

International Preliminary Report on Patentability received for PCT Patent Application No. PCT/EP2016/001515, mailed on Feb. 16, 2018, 26 pages.

International Preliminary Report on Patentability received for PCT Patent Application No. PCT/IB2016/001273, mailed on Mar. 22, 2018, 7 pages.

International search Report and written opinion received for PCT application No. PCT/EP2016/001513, mailed on Feb. 2, 2017, 16 pages.

International search Report and written opinion received for PCT application No. PCT/EP2016/001514, mailed on Jan. 24, 2017, 14 pages.

International Search Report and Written Opinion received for PCT Patent Application No. PCT/EP2016/000087, mailed on Sep. 14, 2016, 10 pages.

International Search Report and Written Opinion received for PCT Patent Application No. PCT/EP2016/000870, mailed on Aug. 25, 2016, 9 pages.

International Search Report and Written Opinion received for PCT Patent Application No. PCT/EP2016/001515, mailed on Nov. 23, 2016, 14 pages.

International Search Report and Written Opinion received for PCT Patent Application No. PCT/IB2016/001273, mailed on Jan. 10, 2017, 9 pages.

Kalifa, et al., “Mechanisms of Wave Fractionation at Boundaries of High Frequency Excltation in the Posterior Left Atrium of the Isolated Sheep Heart During Atrial Fibrillation,” Circulation 2006; 113:626-33.

Kirchhof et al, “2016 ESC guidelines for the management of atrial fibrillation developed in collaboration with EACTS,” European Heart Journal, vol. 37, Issue 38 2016.

Laughner et al., “Practical Considerations of Mapping Persistent Atrial Fibrillation With Whole-Chamber Basket Catheters,” JACC: Clinical Electrophysiology, vol. 2, Issue 1, Feb. 2016, pp. 55-65. Published by Hindawi in Egypt.

Liu et al, 2018, “Visual tracking in high-dimensional particle filter,” PLOS One 13 (8): e0201872, Aug. 23, 2018.

Lochmatter et al, “Swis Track—A Flexible Open Source Tracking Software for Multi-Agent Systems,” 2008 IEEE/ RSJ Int'l Conf. Intell. Robots and Systems, France 2008, pp. 4004-4010.

McEwan et al, “Efficient computational noise in GLSL,” Journal of Graphics Tools, 16(2}:85-94, 2012.

Miroslav Dura et al , “Toward panoramic in situ mapping of action potential propagation in transgenic hearts to investigate initiation and therapeutic control of arrhythmias,” Frontiers in Physiology, vol. 5, Sep. 8, 2014 pp. 1-7.

Murali et al., “Cardiac Ambulatory Monitoring. New Wireless Device Validated Against Conventional Holter Monitoring in a Case Series,” Front. Cardiovasc. Med., Nov. 30, 2020, vol. 7, Lausanne, Switzerland.

Oesterlein et al, “Basket-Type Catheters: Diagnostic Pitfalls Caused by Deformation and Limited Coverage,” BioMed Research International, vol. 2016 Article ID 5340574, published by Elsevier in The Netherlands.

Office Action received for European Application No. 16703057.6, mailed on Jun. 15, 2020, 4 pages.

Office Action received for European Application No. 16763726.3, mailed on Feb. 19, 2019, 6 pages.

Office Action received for European Application No. 16843733.3, mailed on Jul. 22, 2019, 6 pages.

Office Action received for European Application No. 16843733.3, mailed on Jun. 10, 2025, 4 pages.

Office Action received for European Application No. 16843733.3, mailed on Jun. 26, 2023, 4 pages.

Office Action received for European Application No. 18162169.9, mailed on Aug. 26, 2019 5 pages.

Office Action received for European Application No. 18162169.9, mailed on Jun. 26, 2023, 4 pages.

Office Action received for European Application No. 19219296.1, mailed on Jun. 2, 2023, 10 pages.

(56) References Cited

OTHER PUBLICATIONS

Office Action received for European Application No. 20181424.1, mailed on Apr. 23, 2024, 4 pages.
Office Action received for European Application No. 21202891.4, mailed on Oct. 16, 2024, 4 pages.
Office Action received for European Application No. 22176716.3, mailed on Jul. 31, 2023, 9 pages.
Office Action received for European Application No. 22184693.4, mailed on Feb. 3, 2025, 6 pages.
Office Action received for European Application No. 22184693.4, mailed on Nov. 10, 2023, 6 pages.
Office Action received for European Application No. 23164010.3, mailed on Aug. 25, 2025, 8 pages.
PCT Application No. PCT/EP2015/001801, filed on Mar. 16, 2017, by Ruppersberg.
PCT Application No. PCT/EP2015/001803, filed on Mar. 16, 2017, by Ruppersberg.
Potse, "Scalable and Accurate ECG Simulation for Reaction-Diffusion Models of the Human Heart," Apr. 20, 2018, 1-14, vol. 9, Art. 370, Frontiers in Physiology, Switzerland.
Rios-Munoz, "Real-time rotational activity detection in atrial fibrillation," Frontiers in Physiology, Mar. 2018, vol. 9, pp. 1-17, Frontiers Media SA, CH.
Rios-Munoz., "Rotor Detection in Atrial Fibrillation," Doctoral Thesis. Universidad Carios III de Madrid. Jun. 2018 159 pages.
Rodrigo, et al, "Body surface localization of left and right atrial high-frequency rotors in atrial fibrillation patients: A clinical-computational study," Heart Rhythm, Sep. 2014.
Smith et al, "Interactive Computer-Assisted Tracking of Speckle Trajectories in Fluorescence Microscopy: Application to Actin Polymerization and Membrane Fusion," Biophysical Journal. 2011. 101. 1794-804. 10.1016/j.bpj.2011.09.007.
Sohal, et al, "Is Mapping of Complex Fractionated Electrograrns Obsolete?" Arrhythm. Electrophysiol. Rev., Aug. 2015; 4(2): 109-1-15.
Strintzis et al, "Maximum likelihood motion estimation in ultrasound image sequences," in IEEE Signal Processing Letters, vol. 4, No. 6, pp. 156-157, Jun. 1997.
Tinevez et al, "TrackMate: An Open and Extensible Platform for Single-Particle Tracking," Methods. 2016. 115. 10.1016/j.ymeth.2016.09.016.
Vassilis Georgiadis et al, "Multielec: A MATLAB Based Application for MEA Data Analysis," PLOS One, Jun. 15, 2015, pp. 1-17.
Zhu et al, "Real-Time Motion Capture: An Overview," Complex Intelligent and Software Intensive Systems (CISIS) 2016 10th International Conference on, pp. 522-525, 2016.
"An Iterative Image Registration Technique with an Application to Stereo Vision," Bruce D. Lucas, Takeo Kanade, Proceedings of Imaging Understanding Workshop, pp. 121-130(1).
"Chaste: An Open Source C++ Library for Computational Physiology and Biology," Gary R. Mirams, et al. PLOS Computational Biology, Mar. 14, 2013, vol. 9, Issue3, e1002970.
"Horn-Schunck Optical Flow with a Multi-scale Strategy," Enric Meinhardt-Llopis et al., Image Processing On Line, 3 (2013), pp. 151-172.
"Impact of Rotor Ablation in Nonparoxysmal Atrial Fibrillation Patients," Sanghamitra Mohanty, et al., J. of the American College of Cardiology, vol. 68, No. 3, 2016.
"Interpolation with Splines in Tension: A Green's Function Approach," Paul Wessel and David Bercovici, Mathematical Geology, 77-93, vol. 30, No. 1, 1998.
"Lucas/Kanada Meets Horn/Schunck: Combining Local and Global Optic Flow Methods," Andres Bruhh, Joachim Waickert, Christoph Schnorr, International Journal of Computer Vision.
"Moving Surface Spline Interpolation Based on Green's Function," Xingsheng Deng and Zhong-an Tang, Math, Geosci (2011). 43:663-680.
"Novel Sirategy for Improved Substrate Mapping of the Atria Omnipolar Catheter and Signal Processing Technology Assesses Electrogram Signals Along Physiologic and Anatomic Directions," Deno et al., Circulation; Nov. 10, 2015, vol. 132, Issue Suppl. 3.
"Prospectively Quantifying the Propensity for Atrial Fibrillation: A Mechanistic Formulation," Carrick et al. ; Mar. 13, 2015, PLOS One, DOI:10.1371 journal.pone.0118746.
"Segmental Boundary Profile of Myocardial Motion to Localize Cardiac Abnormalities," Slamet Riyadi et al, Proceedings of the World Congress on Engineering 2010, vol. 1.
"SimpleFlow: A Non-Iterative, Sublinear Optical Flow Algorithm," Michael Tao et al. Eurographics 2012, vol. 31 (2012), No. 2.
Atienza et al,, "Mechanisms of Fractionated Electrograms Formation in the Posterior Left Atrium During Paroxysmal, Atrial Fibrillation in Humans," J Am Coll Cardiol. Mar. 1, 2011; 57(9): 1081-1092.
Bellmann, "Velocity characteristics of atrial fibrillation sources determined by electrographic flow mapping before and after catheter ablation," Int'l Journal of Card., Feb. 2019, vol. 286, pp. 56-60, Elsevier, NL.
Bellmann, B., Electrographic Flow Mapping—A New Technology for Identification of Atrial Fibrillation Drivers; Jun. 1, 2017; P239; vol. 19; pp. iiiS4-iii55.Europace; Oxford, UK.
Bellmann, Identification of active atrial fibrillation sources and their discrimination from passive rotors , Clinical Research in Cardiology, 2018, 107: 1021-1032.
Cabral et al, "Imaging vector fields using line integral convolution," Technical report, Lawrence Livermore National Lab., CA (United States), 1993.
Cantwell, C.D., "Techniques for automated local activation time annotation & conduction velocity estimation in cardiac mapping," Com. Bio. Med. 65 (2015) 229-242, Elsevier, NL.
Catmull et al, "A class of local interpolating splines," Computer Aided Geometric Design, 317-326. Elsevier, 1974.
Correa de Sa et al., Electrogram Fracfomation—The Relationship between Spatiotemporal Variation of Tissue Excitation and Electrode Spatial Resolution, Circ Arrhythm, Electrophysiol. Dec. 2011; 4(6}: 909-16.
Correll et al, 2006, "SwisTrack: A Tracking Tool for Multi-Unit Robotic and Biological Systems," IEEE International Conference on Intelligent Robots and Systems. 2185-2191.
Decision to grant a European patent received for European Application No. 15736393.8, mailed on Sep. 16, 2021, 2 pages.
Decision to grant received for European Application No. 16703057.6, mailed on Oct. 31, 2024, 2 pages.
Decision to grant received for European Application No. 16763726.3, mailed on Jul. 6, 2023, 2 pages.
Decision to grant received for European Application No. 21176633.2, mailed on Nov. 17, 2022, 2 pages.
Decision to grant received for European Application No. 22176716.3, mailed on May 3, 2024, 3 pages.
Eugene K. Lee et al., Machine learning plus optical flow a simple and sensitive method to detect cardioactive drugs, Nature, vol. 5, Jul. 3, 2015, pp. 1-12.
European Search Report received for European Application No. 18162169.9, mailed on Jun. 28, 2018, 11 pages.
European Search Report received for European Application No. 19170337.0, mailed on Aug. 27, 2019, 12 pages.
Extended European Search Report received for European Application No. 16843733.3, mailed on Sep. 12, 2018, 8 pages.
Extended European Search Report received for European Application No. 18162169.9, mailed on Nov. 19, 2018, 12 pages.
Extended European Search Report received for European Application No. 19170337.0, mailed on Nov. 27, 2019, 11 pages.
Extended European Search Report received for European Application No. 19219296.1, mailed on Jul. 1, 2020, 10 pages.
Extended European Search Report received for European Application No. 20181424.1, mailed on Nov. 2, 2020, 9 pages.
Extended European Search Report received for European Application No. 21176633.2, mailed on Nov. 5, 2021, 7 pages.
Extended European Search Report received for European Application No. 21202891.4, mailed on Feb. 15, 2022, 7 pages.
Extended European Search Report received for European Application No. 22176716.3, mailed on Nov. 29, 2022, 12 pages.

(56) References Cited

OTHER PUBLICATIONS

Extended European Search Report received for European Application No. 22184693.4, mailed on Dec. 9, 2022, 9 pages.
Extended European Search Report received for European Application No. 23164010.3, mailed on Jul. 12, 2023, 9 pages.
Ferrer ET, "Detailed Anatomical and Electrophysiological Models of Human Atria and Torso for the Simulation of Atrial Activation" PLOS One, Nov. 2, 2015.
Gall et al, "Functional Categorization of Objects using Real-time Markerless Motion Capture," IEEE Conf. on Computer Vision and Pattern Recognition (CVPR''11), 1969-1976, 2011.
Golemati et al., "Ultrasound-Image-Based Cardiovascular Tissue Motion Estimation," in IEEE Reviews in Biomedical Engineering, vol. 9, pp. 208-218, 2016.
He et al, "Video Target Tracking Based on Adaptive Kalman Filtering, Communications, Signal Processing, and Systems," CSPS 2019. Lecture Notes, vol. 571, Springer, Singapore.
Horn, et al., "Determining Optical Flow," Artificial Intelligence, vol. 17, pp. 185-204, 1981.
Hummel et al., "Atrial mapping with basket catheters—A Basket case?," JACC: Clinical Electrophysiology, vol. 2 Issue 1, Feb. 2016, pp. 66-68. (Hummel et al., continued) published by Elsevier in The Netherlands.
Intention to Grant received for European Application No. 15736393.8, mailed on May 6, 2021, 6 pages.
Intention to grant received for European Application No. 16703057.6, mailed on Jun. 19, 2024, 6 pages.
Intention to grant received for European Application No. 16763726.3, mailed on Mar. 16, 2023, 6 pages.
Intention to grant received for European Application No. 18162169.9, mailed on Aug. 21, 2025, 6 pages.
Intention to grant received for European Application No. 21176633.2, mailed on Jul. 5, 2022, 6 pages.
Intention to grant received for European Application No. 22176716.3, mailed on Dec. 20, 2023, 6 pages.
Extended European Search Report and Search Opinion received for European Application No. 25204955.6, mailed on Mar. 12, 2026, 7 pages.
Extended European Search Report and Search Opinion received for European Application No. 25225296.0, mailed on Mar. 25, 2026, 8 pages.
Office Action received for European Application No. 20181424.1, mailed on Apr. 4, 2026, 6 pages.

* cited by examiner

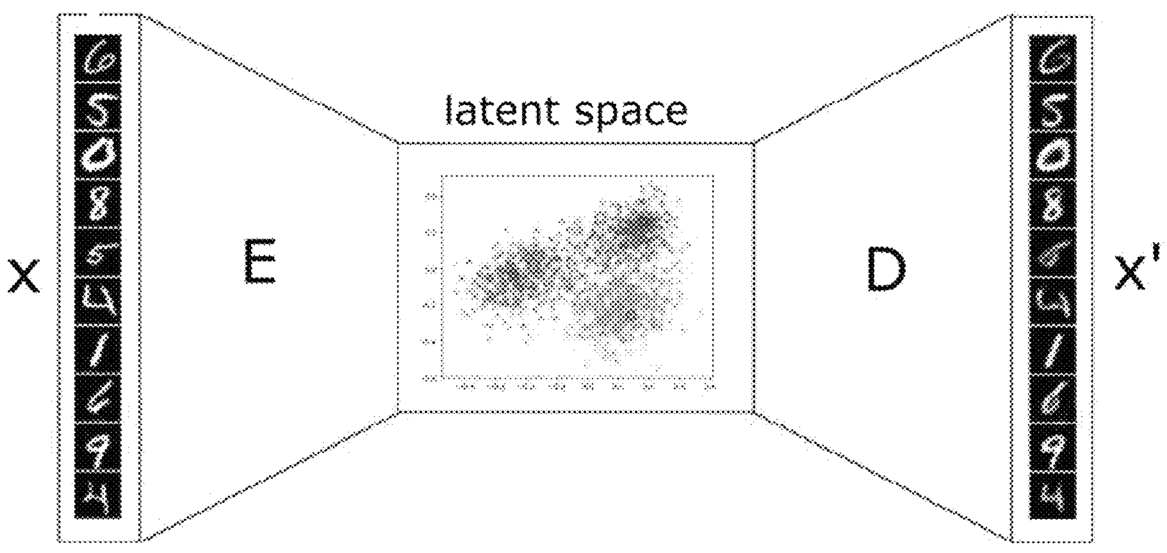
FIG. 10
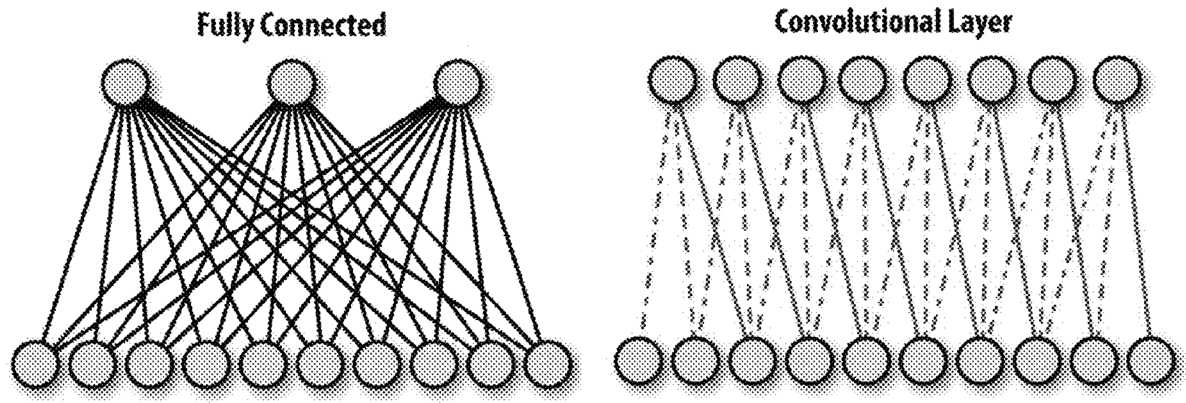
FIG. 11A
FIG. 11B

| D1 | H1 | H2 | H3 | H4 | H5 | H6 | H7 | H8 | D8 |
|---|---|---|---|---|---|---|---|---|---|
| E1 | A1 | A2 | A3 | A4 | A5 | A6 | A7 | A8 | E8 |
| F1 | B1 | B2 | B3 | B4 | B5 | B6 | B7 | B8 | F8 |
| G1 | C1 | C2 | C3 | C4 | C5 | C6 | C7 | C8 | G8 |
| H1 | D1 | D2 | D3 | D4 | D5 | D6 | D7 | D8 | H8 |
| A1 | E1 | E2 | E3 | E4 | E5 | E6 | E7 | E8 | A8 |
| B1 | F1 | F2 | F3 | F4 | F5 | F6 | F7 | F8 | B8 |
| C1 | G1 | G2 | G3 | G4 | G5 | G6 | G7 | G8 | C8 |
| D1 | H1 | H2 | H3 | H4 | H5 | H6 | H7 | H8 | D8 |
| E1 | A1 | A2 | A3 | A4 | A5 | A6 | A7 | A8 | E8 |

FIG. 18

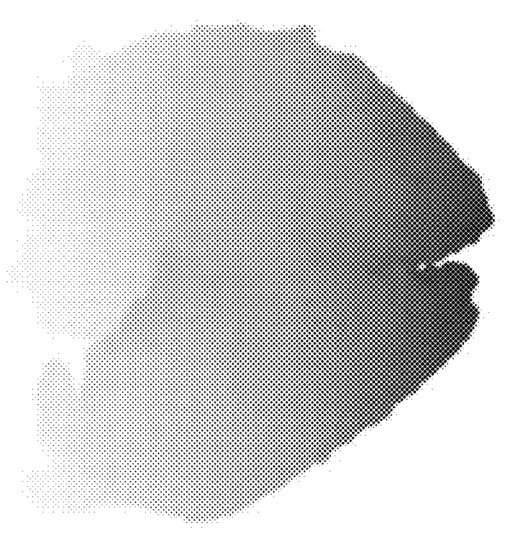
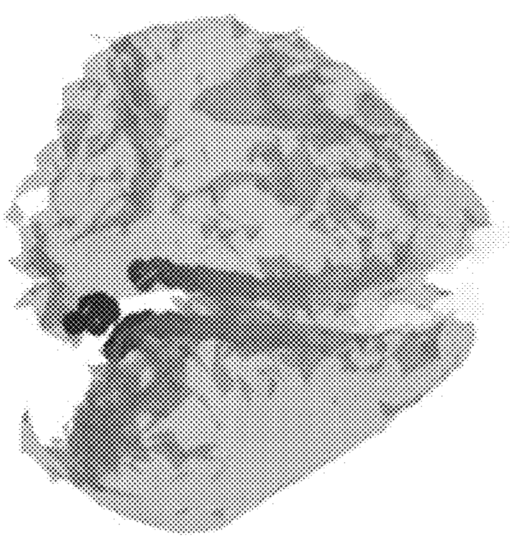
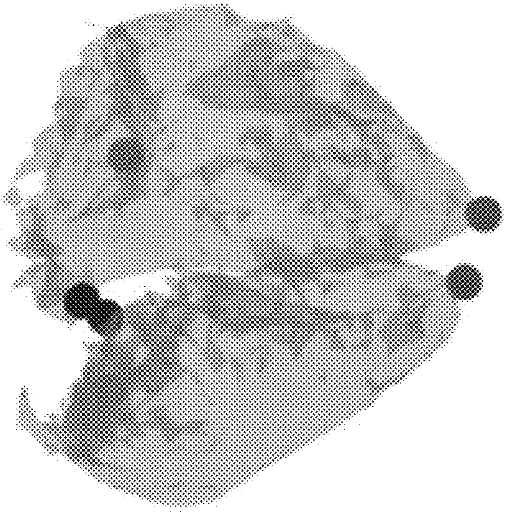
FIG. 21

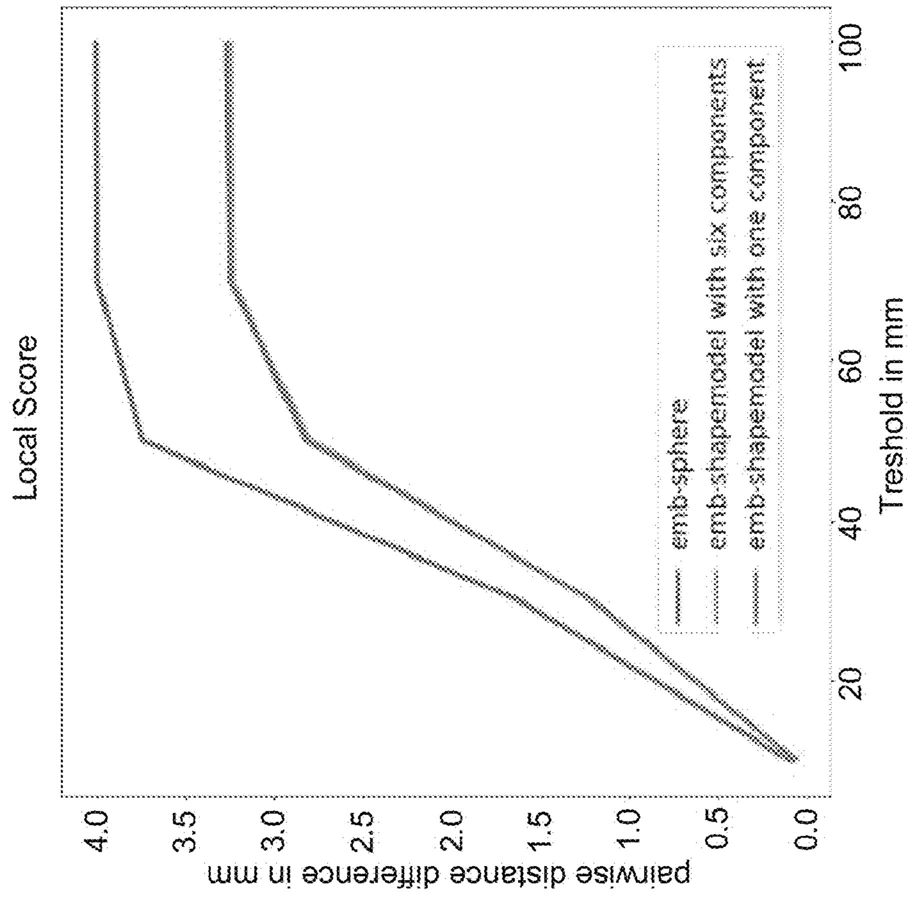
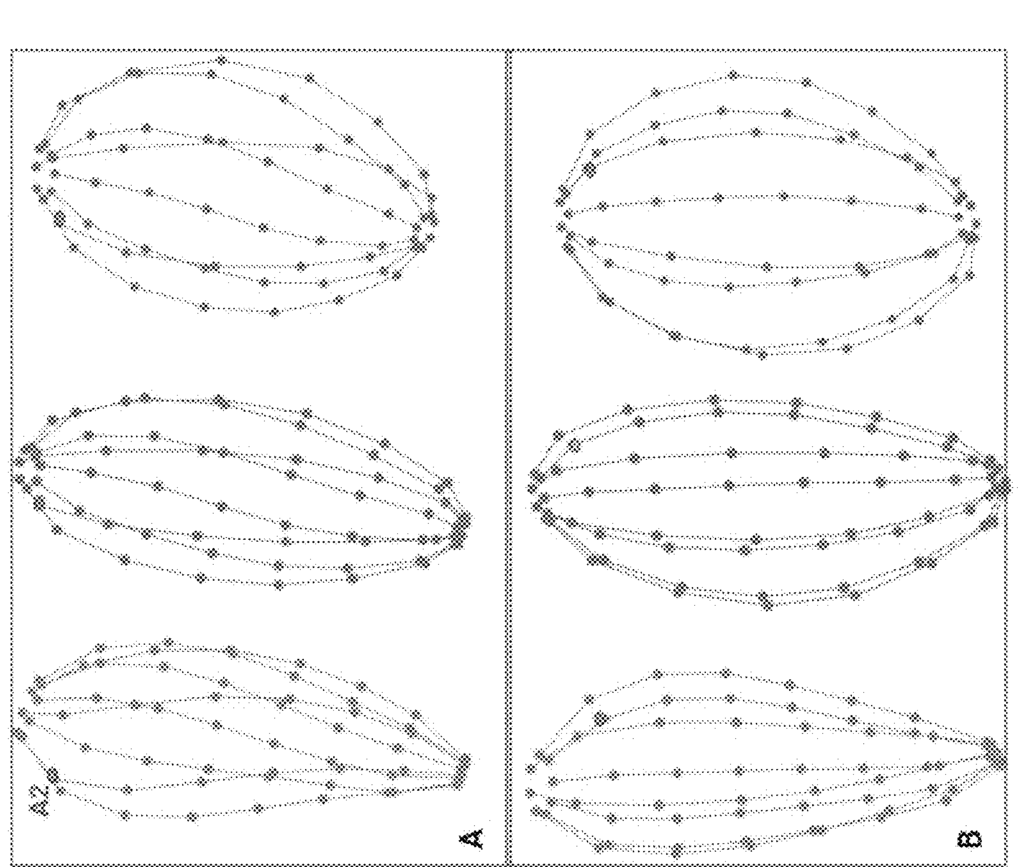
FIG. 29

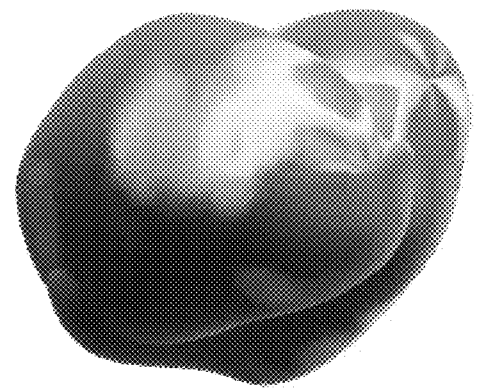
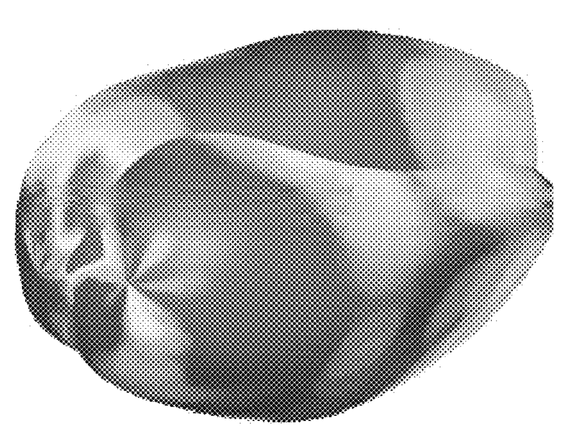
FIG. 31

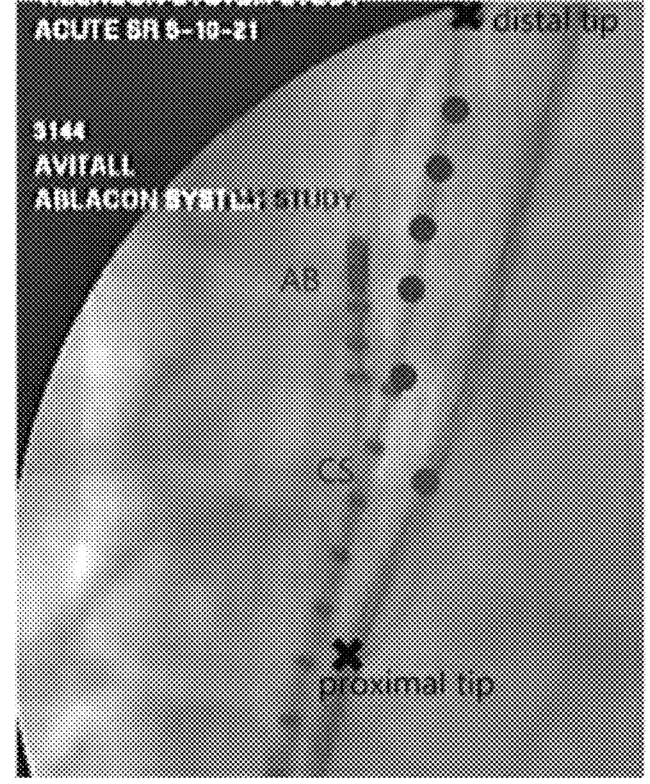
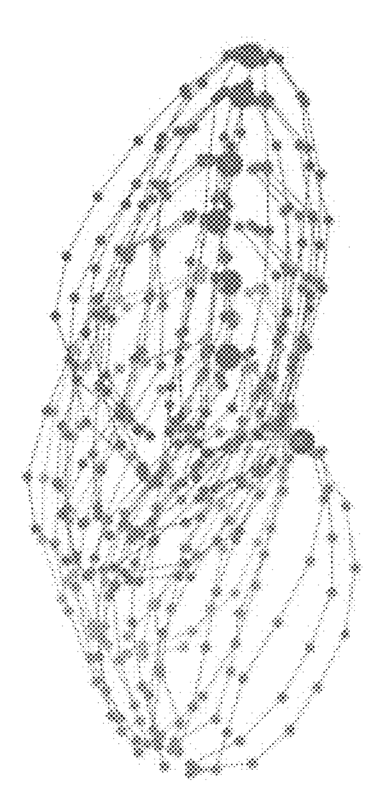
FIG. 32

| Patient name | proposed method | CARTO® |
|---|---|---|
| P-ROT-032 | ridge | ridge |
| 02-004 | inside appendage | inside appendage |
| P-ROT-046 | roof | roof |
| P-ROT-035 | septal | septal |
| 02-009 | ridge | ridge |
| P-ROT-020 | septal | septal |
| P-ROT-045 | inferior wall | inferior wall |
| P-ROT-039 | RUPV | RUPV |
| P-ROT-028 | ridge | ridge |
| 02-001 | ridge | inside appendage |
| P-ROT-001 | anterior wall | ridge |
| P-ROT-004 | anterior wall | lateral wall |
| P-ROT-006 | inside appendage | ridge |
| P-ROT-019 | RUPV | posterior wall |
| P-ROT-034 | LUPV | ridge |
| P-ROT-027 | roof | ridge |
| P-ROT-052 | posterior wall | ridge |
| P-ROT-003 | posterior wall | anterior wall |

FIG. 35

BIOSIGNAL-BASED NAVIGATION OF ELECTROPHYSIOLOGICAL MAPPING BASKETS USING STATISTICAL SHAPE MODELS

RELATED APPLICATIONS

This application is a continuation-in-part of, and claims priority and other benefits from, U.S. Utility patent application Ser. No. 17/831,249 entitled "Methods, Systems, Devices, and Components for Extracting Atrial Signals from QRS and QRST Complexes" to Tenbrink et al. filed Jun. 2, 2022 (hereafter "the '249 patent application"). The '249 patent application claims priority and other benefits from: (a) U.S. Provisional Patent Application Ser. No. 63/196,605 entitled "Methods, Systems, Devices, and Components for Extracting Atrial Signals from QRS and QRST Complexes" to Tenbrink et al. filed Jun. 3, 2021 (hereafter "the '605 patent application"); (b) U.S. Provisional Patent Application Ser. No. 63/221,291 entitled "Biosignal-Based Intracardiac Navigation Systems, Devices, Components and Methods" to Denner et al. filed Jul. 13, 2021 (hereafter "the '291 patent application"), and (c) U.S. Provisional Patent Application Ser. No. 63/222,346 entitled "Biosignal-Based Intracardiac Navigation Systems, Devices, Components and Methods" to Denner et al. filed Jul. 15, 2021 (hereafter "the '346 patent application"). Through the '249 patent application, this application claims priority and other benefits from the '605 patent application, the '291 patent application, and the '346 patent application.

This application is also a continuation-in-part of, and claims priority and other benefits from, U.S. Utility patent application Ser. No. 17/863,246 entitled "Biosignal-Based Intracardiac Navigation Systems, Devices, Components and Methods" to Denner et al. filed Jul. 12, 2022 (hereafter "the '246 patent application"). The '246 patent application claims priority and other benefits from the '291 and '346 patent applications.

This application is further related to, and claims priority and other benefits from, U.S. Provisional Patent Application Ser. No. 63/323,163 entitled "Machine Learning-Based Electroanatomical Mapping of the Heart with Generation of 3D Reconstructions from Biosignals" to Grund et al. filed Mar. 24, 2022 (hereafter "the '163 patent application").

Each of the '249, '605, '246, 291, '346 and 163 patent applications is hereby incorporated by reference herein, each in its respective entirety.

FIELD OF THE INVENTION

Various embodiments described and disclosed herein relate to the field of medicine generally, and more particularly to detecting, diagnosing, predicting and treating cardiac rhythm disorders such as atrial fibrillation in a patient's heart.

BACKGROUND

Persistent atrial fibrillation (AF) is assumed to be caused by structural changes in atrial tissue, which can manifest themselves as multiwavelet re-entry and/or stable rotor mechanisms (see, e.g., De Groot M S et al., "Electropathological Substrate of Longstanding Persistent Atrial Fibrillation in Patients with Structural Heart Disease Epicardial Breakthrough," Circulation, 2010, 3: 1674-1682). Radio frequency (RF) ablation targeting such host drivers of AF is generally accepted as the best therapeutic approach. RF ablation success rates in treating AF cases are currently limited, however, by a lack of diagnostic tools that are capable of precisely determining the source (or type), and location, of such AF drivers. Better diagnostic tools would help reduce the frequency and extent of cardiac ablation procedures to the minimum amount required to treat AF, and would help balance the benefits of decreased fibrillatory burden against the morbidity of increased lesion load.

One method currently employed to localize AF drivers is the TOPERA® RhythmView® system, which employs a basket catheter having 64 electrodes arranged in an 8×8 pattern from which the system records unipolar electrograms or electrogram signals (EGMs). The RhythmView® algorithm creates a propagation map of the 64 electrodes through a phase analysis of EGM peaks after improving the signal to noise ratio through filtering and subtraction of a simulated compound ECG artifact. The RhythmView® algorithm detects where peak sequences between electrodes show a circular pattern candidate for a re-entry cycle and indicates those locations in a Focal Impulse and Rotor Map (FIRM) using A1 to H8 chess field coordinates for the electrodes. The resolution of the TOPERA system is limited by the spacing of the electrodes and consequently does not show the details of the AF drivers. In particular, the TOPERA system cannot show if a circular EGM wavefront is actively generated by a re-entry mechanism and is therefore is a driver of AF (i.e., an active rotor), or whether a circular EGM wavefront simply represents turbulence passively generated by an EGM wavefront hitting a barrier (i.e., a passive rotor). In addition, the TOPERA system does not show the direction of AF wavefront propagation, and does not provide the spatial or temporal resolution required to detect singularities associated with the generation of an active rotor.

A recent independent multicenter study ("OASIS, Impact of Rotor Ablation in Non-Paroxysmal AF Patients: Results from a Randomized Trial," Sanghamitra Mohanty, et al. and Andrea Natale, J Am Coll Cardiol. 2016) reported that the results obtained using TOPERA FIRM technology were inferior to those provided by non-specific ablation of the posterior wall of the left atrium. Moreover, the results suggested that FIRM based ablation is not sufficient for therapeutic success without pulmonary vein isolation (PVI) being performed in parallel. Although there are some questions about the methodology of this trial, many experts are convinced that the resolution and interpretability of the TOPERA system need to be improved.

In another approach to the problem, Toronto scientists recently presented a strategy to analyze EGM wave propagation using "Omnipolar Mapping," which seeks to measure beat-by-beat conduction velocity and direction (see, e.g., "Novel Strategy for Improved Substrate Mapping of the Atria: Omnipolar Catheter and Signal Processing Technology Assesses Electrogram Signals Along Physiologic and Anatomic Directions," D. Curtis Deno et al. and Kumaraswamy Nanthakumar; Circulation. 2015; 132:A19778). This approach starts with the time derivative of a unipolar EGM as measured by a set of electrodes having known distances to one other. Assuming constant velocity, the velocity and direction representing the best fit for a spatial derivative of the measured EGM are calculated and used to represent an estimate of the E field. According to a communication by Dr. Nanthakumar at the 2016 CardioStim Convention in Nice, France, however, this method remains incapable of dealing successfully with complex data sets, such as those obtained during an episode of AF.

AF is the most common supraventricular tachyarrhythmia worldwide and is associated with a significant health burden.

Catheter ablation of pulmonary veins (PV) has been established as a therapeutic option for patients with symptomatic drug-refractory paroxysmal AF and results in high clinical success. However, the treatment of persistent and long-standing persistent AF is still challenging. A large number of patients present with recurrence of atrial tachyarrhythmia during mid- and long-term follow up. To achieve higher success rates, different ablation strategies have been reported, such as targeting additional AF sources. The initial results of focal impulse and rotor (FIRM) mapping for guiding catheter ablation of AF seemed to be promising. However, currently available systems for AF driver identification still have significant limitations, such as limited spatial resolution and difficulties in discriminating between active and passive rotors.

AF is a heart disease that prevents the upper chambers of the heart (the atria) from contracting properly, which can result in the heart quivering instead of beating in a correct rhythm. A diagnosis of AF can result in patient having a five-fold risk of stroke, a three-fold incidence of congestive heart failure, and higher mortality. For effective treatment of AF, the electrical activity of the atria needs to be understood, which can be accomplished by placing a catheter with attached electrodes inside the atria, recording the resulting intra-cardiac signals as electrograms (or EGMs), and then viewing or otherwise analyzing the resulting EGMs. To better sense and understand electrical activity in the atria, multiple EGMs with the catheter in multiple positions are generally recorded. For the placement and navigation of the catheter, 3D catheter navigation systems are typically employed, which permit accurate visualization and determination of the position of the catheter inside the atria. Unfortunately, such navigation systems have the shortcomings of either requiring additional hardware and/or introducing artifacts into the EGMs, not to mention the significant costs and technical complications associated with such navigation systems. Artifacts in EGMs can be especially critical, since EGMs are the foundation upon which treatment decisions are made. EGMs recorded with high fidelity, and not containing or containing few artifacts can be crucial to accurate diagnosis and subsequent treatment success.

What is needed are improved means and methods of acquiring and processing intracardiac electrogram signals that reliably and accurately yield the precise locations and sources of cardiac rhythm disorders in a patient's heart. Doing so would enable cardiac ablation procedures to be carried out with greater locational precision, and would result in higher rates of success in treating cardiac rhythm disorders such as AF.

SUMMARY

In one embodiment, there is provided a method of at least one of navigating and determining a position or orientation of an intra-cardiac electrophysiological (EP) mapping basket of an EP mapping catheter, the basket being disposed inside or near an atrium or other heart chamber or portion of a patient's heart, the EP mapping basket comprising a plurality of electrodes mounted on one or more arms or splines thereof, each electrode having a location or position on one or more splines or arms associated therewith, where the method comprises recording or acquiring a plurality of intra-cardiac signals inside or near the heart of the patient using the plurality of electrodes, a data acquisition or recording device, and a computing device, the data acquisition or recording device and computing device being operably connected to the EP mapping catheter and the electrodes thereof, the recorded or acquired intra-cardiac signals each having at least one electrode associated therewith; using the computing device, isolating or extracting ventricular signals from the at least some of the recorded or acquired intra-cardiac signals; and using the computing device, determining, using the extracted or isolated ventricular signals, at least one of a statistical shape model of the EP mapping basket and the locations of the electrodes inside or near the patient's atrium, heart chamber or other portion of the patient's heart that are associated with each or a plurality of isolated or extracted ventricular signals.

Such an embodiment may further comprise one or more of: (a) the computing device employing a neural network or other machine learning architecture to compute, determine or reconstruct the extracted or isolated ventricular signals; (b) the computing device employing a neural network or other machine learning architecture to generate a center of mass for each or selected positions of the EP mapping basket; (c) the computing device employing a neural network or other machine learning architecture or machine learning algorithm to align or project reconstructions of the EP mapping basket and its electrodes onto an anatomy model of the patient's heart; (d) recording or acquiring at least one body surface signal from the patient using at least one body surface electrode, the at least one body surface signal being acquired or recorded simultaneously or substantially simultaneously with the recorded or acquired intra-cardiac signals; (e) using the computing device, isolating or extracting at least one ventricular signal from the recorded or acquired body surface signal, and determining, using the extracted or isolated intra-cardiac and at least one body surface ventricular signals and the computing device, the locations of the electrodes inside the patient's heart that are associated with each isolated or extracted ventricular signal; (f) the isolated or extracted ventricular signals comprising QRS complexes; (g) moving the basket inside the patient's atrium to different positions, and recording or acquiring intra-cardiac signals at each such position; (h) using the computing device, removing low-frequency or other artefacts or noise from the recorded or acquired intra-cardiac and/or body surface signals; (i) recording or acquiring a plurality of intra-cardiac signals for each electrode while the basket is in a given position within the patient's atrium, and, using the computing device, isolating or extracting a ventricular signal for each such intra-cardiac signal; (j) using the computing device, determining changes in the three-dimensional locations and orientations of the basket and the electrodes thereof as the basket is moved around, in or near the patient's atrium or other heart chamber; (k) using the computing device and a display, navigating the basket inside or near the patient's atrium or other heart chamber; (l) providing a visual display to a user of the locations of the electrodes and/or basket inside or near the patient's atrium or other heart chamber; (m) using the computing device and the isolated or extracted ventricular signals, at least one neural network to determine the locations of the electrodes and/or basket inside or near the patient's atrium or other heart chamber, and (n) the locations of at least one of the electrodes and the basket inside or near the patient's atrium or other heart chamber being provided in a visualization to a user in near real time.

In another embodiment, there is provided a system configured to at least one of navigate and determine a position or orientation of an intra-cardiac electrophysiological (EP) mapping basket of an EP mapping catheter, the basket being disposed inside or near an atrium or other heart chamber or portion of a patient's heart, the EP mapping basket comprising a plurality of electrodes mounted on one or more arms or splines thereof, each electrode having a location or position on one or more splines or arms associated therewith, where the system comprises a data acquisition or recording device, and a computing device, the data acquisition or recording device and computing device being operably connected to the EP mapping catheter and the electrodes thereof, the data acquisition or recording device being configured to record or acquire a plurality of intra-cardiac signals inside or near the heart of the patient using the plurality of electrodes, the recorded or acquired intra-cardiac signals each having at least one electrode associated therewith; wherein the computing device is configured to isolate or extract ventricular signals from the at least some of the recorded or acquired intra-cardiac signals, and the computing device is further configured to determine, using the extracted or isolated ventricular signals, at least one of a statistical shape model of the EP mapping basket and the three-dimensional locations of the electrodes inside or near the patient's atrium, heart chamber or other portion of the patient's heart that are associated with each or a plurality of isolated or extracted ventricular signals.

Such an embodiment may further comprises one or more of (a) the computing device comprising a neural network or other machine learning architecture to compute, determine or reconstruct the extracted or isolated ventricular signals; (b) the computing device being configured to employ a neural network or other machine learning architecture to generate a center of mass for each or selected positions of the EP mapping basket; (c) the computing device being configured to employ a neural network or other machine learning architecture or machine learning algorithm to align or project reconstructions of the EP mapping basket and its electrodes onto a model of the patient's heart; (d) the system being further configured to record or acquire at least one body surface signal from the patient using at least one body surface electrode, the at least one body surface signal being acquired or recorded simultaneously or substantially simultaneously with the recorded or acquired intra-cardiac signals; (e) the system being further configured to isolate or extract at least one ventricular signal from the recorded or acquired body surface signal, and determine, using the extracted or isolated intra-cardiac and at least one body surface ventricular signals and the computing device, the locations of the electrodes inside the patient's heart that are associated with each isolated or extracted ventricular signal; (f) the isolated or extracted ventricular signals comprising QRS complexes; (g) the system being further configured to record or acquire intra-cardiac signals as the basket is moved inside the patient's atrium to different positions; (h) the computing device being configured to remove low-frequency or other artefacts or noise from the recorded or acquired intra-cardiac and/or body surface signals; (i) the computing device being configured to record or acquire a plurality of intra-cardiac signals for each electrode while the basket is in a given position within the patient's atrium, and to isolate or extract a ventricular signal for each such intra-cardiac signal; (j) the computing device being further configured to determine changes in the three-dimensional locations and orientations of the basket and the electrodes thereof as the basket is moved around, in or near the patient's atrium or other heart chamber; (k) the computing device and a display associated therewith being configured to permit the basket to be navigated inside or near the patient's atrium or other heart chamber by a user; (l) the system further comprising a visual display operably connected to the computing device configured to provide a user such that the user can see the locations of the electrodes and/or basket inside or near the patient's atrium or other heart chamber; (m) at least one neural network configured to provide the locations of the electrodes and/or basket inside or near the patient's atrium or other heart chamber; (n) the computing device and a display are configured to provide a visualization of locations of at least one of the electrodes and the basket inside or near the patient's atrium or other heart chamber to a user.

Further embodiments are disclosed herein or will become apparent to those skilled in the art after having read and understood the claims, specification and drawings hereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Different aspects of the various embodiments will become apparent from the following specification, drawings and claims in which:

FIG. 10 shows one embodiment of an example of a learned latent space in an auto-encoder;

FIGS. 11A and 11B show one embodiment of examples of connections of neurons in a fully connected layer and a convolutional layer;

FIG. 18 shows one embodiment of the inputs to convolutional layers;

FIG. 21 shows modeled propagation patterns in the ventricles;

FIG. 29 shows ground truth deformations and local score predictions:

FIG. 31 shows two different basket catheter positions and corresponding EGF maps;

FIG. 32 shows a fluoroscopic image and basket catheter positions;

FIG. 35 shows the locations of prevalent sources determined according to two different methods.

The drawings are not necessarily to scale. Like numbers refer to like parts or steps throughout the drawings.

DETAILED DESCRIPTIONS OF SOME EMBODIMENTS

Described herein are various embodiments of systems, devices, components and methods for diagnosing and treating cardiac rhythm disorders in a patient's heart using electrophysiological mapping or electrographic flow (EGF) techniques, as well as imaging, navigation, cardiac ablation and other types of medical systems, devices, components, and methods. Various embodiments described and disclosed herein also relate to systems, devices, components and methods for discovering with enhanced precision the location(s) of the source(s) of different types of cardiac rhythm disorders and irregularities. Such cardiac rhythm disorders and irregularities, include, but are not limited to, arrhythmias, atrial fibrillation (AF or A-fib), atrial tachycardia, atrial flutter, paroxysmal fibrillation, paroxysmal flutter, persistent fibrillation, ventricular fibrillation (V-fib), ventricular tachycardia, atrial tachycardia (A-tach), ventricular tachycardia (V-tach), supraventricular tachycardia (SVT), paroxysmal supraventricular tachycardia (PSVT), Wolff-Parkinson-White syndrome, bradycardia, sinus bradycardia, ectopic atrial bradycardia, junctional bradycardia, heart blocks, atrioventricular block, idioventricular rhythm, areas of fibrosis, breakthrough points, focus points, re-entry points, premature atrial contractions (PACs), premature ventricular contractions (PVCs), and other types of cardiac rhythm disorders and irregularities.

Various embodiments of EGF techniques, methods, systems, devices, and components are described and disclosed herein, which involve the acquisition of intra-cardiac and/or body surface electrograms, and the subsequent processing and analysis of such electrograms to reveal the locations of sources of cardiac rhythm disorders in a patient's heart, such as rotors and sources that cause or contribute to AF. That is, many of the various techniques, methods, systems, devices, and components described and disclosed herein may be referred to collectively as pertaining to "EGF."

Systems and methods configured to detect in a patient's heart a location of a source of at least one cardiac rhythm disorder are disclosed herein. In the following description, for the purposes of explanation, numerous specific details are set forth in order to provide a thorough understanding of example embodiments or aspects. It will be evident, however, to one skilled in the art that an example embodiment may be practiced without necessarily using all of the disclosed specific details.

Figure 1A:
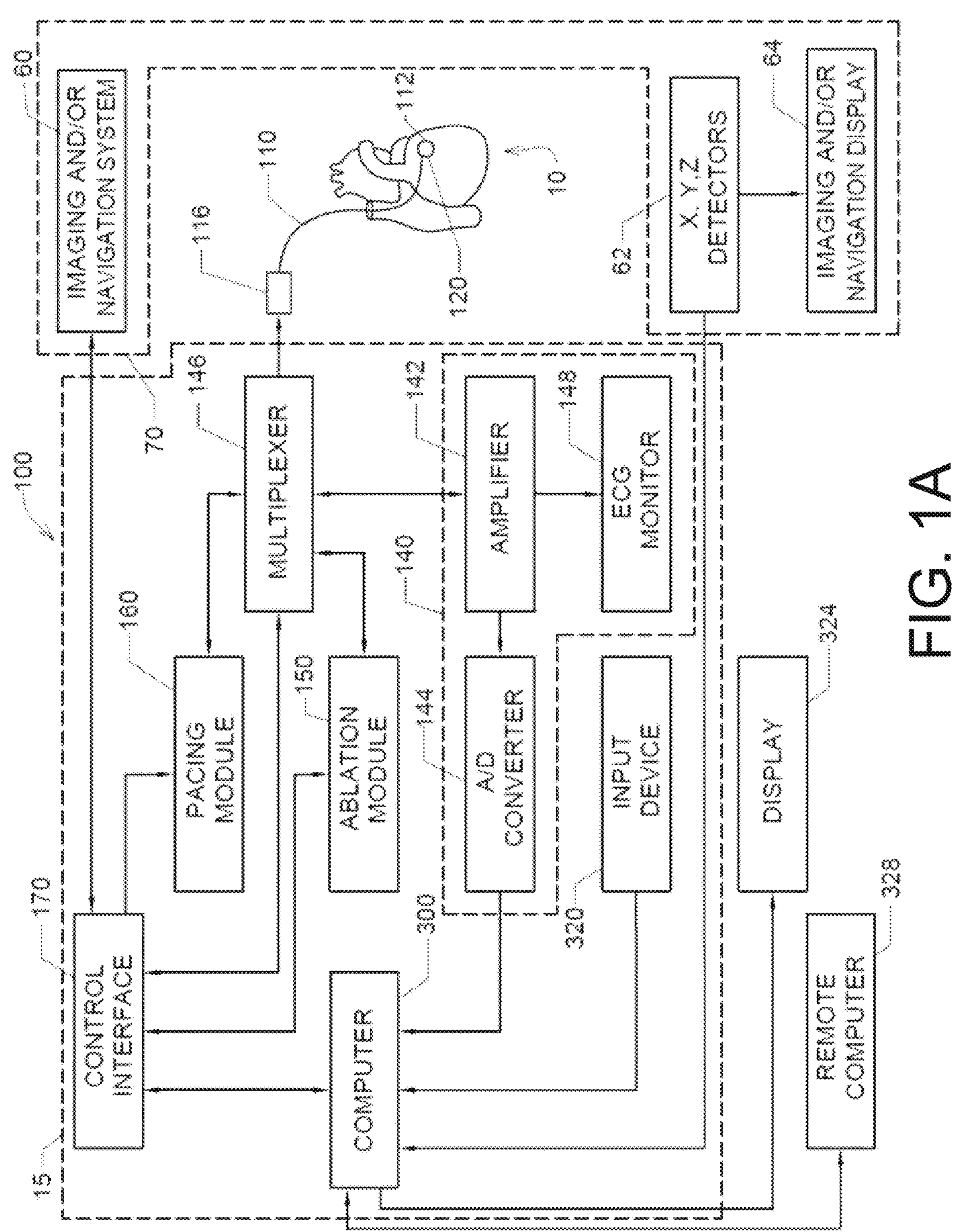
FIG. 1A shows one embodiment of a combined cardiac electrophysiological mapping (EP), pacing and ablation system 100.

Some Embodiments of Electrophysiological Mapping and Pacing and Ablation Systems, Computer Systems, Intracardiac Imaging and Navigation Systems, and Body Surface Imaging and Navigation Systems Referring now to FIG. 1A, there is illustrated one embodiment of a combined cardiac electrophysiological mapping (EP), pacing and ablation system 100. Note that in some embodiments system 100 may not include ablation module 150 and/or pacing module 160, and that the various components thereof need not be combined together into a single system.

Figure 1B:
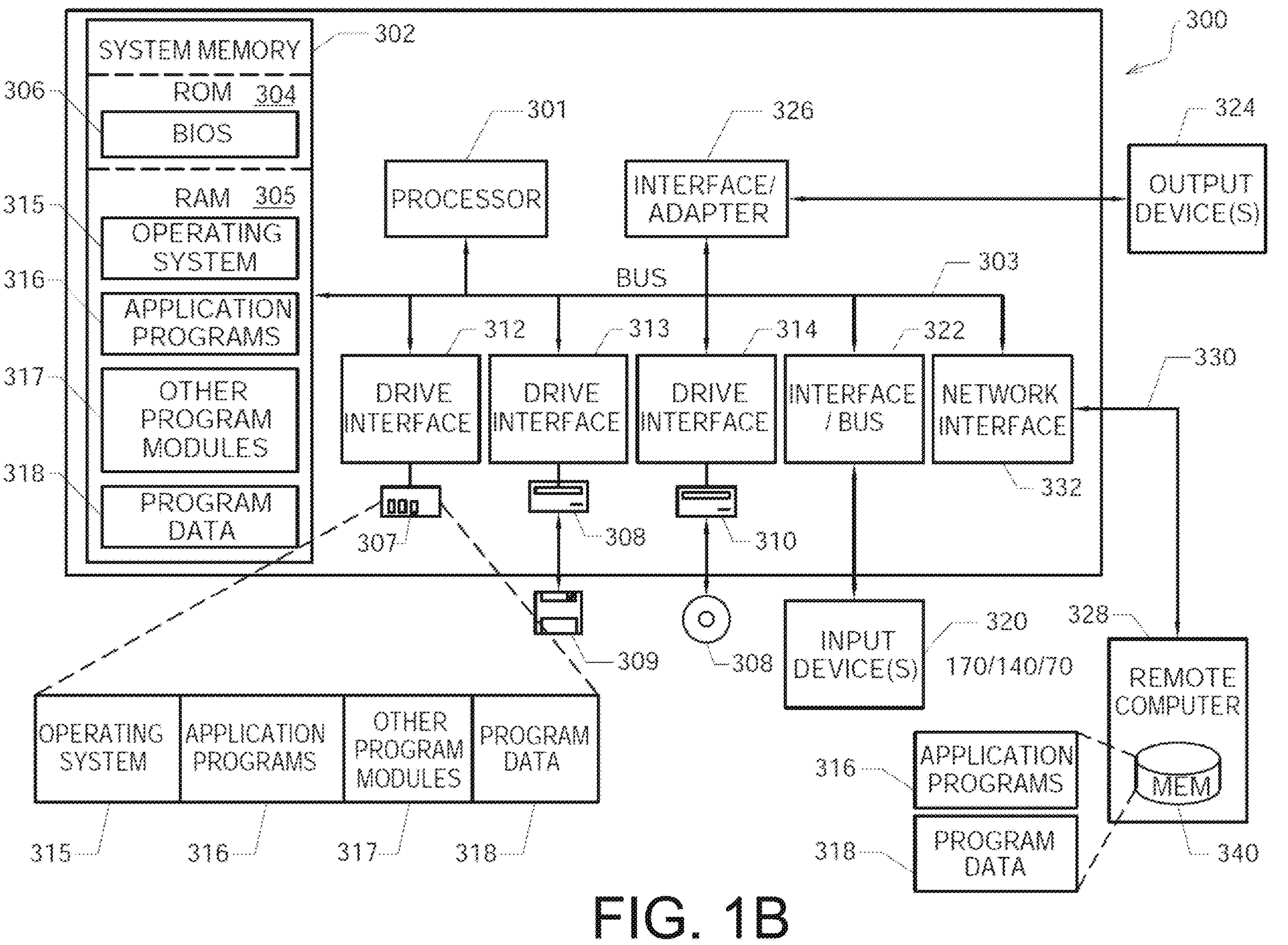
FIG. 1B shows one embodiment of a computer system 300.

Among other things, the embodiment of system 100 shown in FIG. 1B is configured to detect and reconstruct cardiac activation information acquired from a patient's heart relating to cardiac rhythm disorders and/or irregularities, and is further configured to detect and discover the location of the source of such cardiac rhythm disorders and/or irregularities with enhanced precision relative to prior art techniques. In some embodiments, system 100 is further configured to treat the location of the source of the cardiac rhythm disorder or irregularity, for example by ablating the patient's heart at the detected location.

The embodiment of system 100 shown in FIG. 1B comprises five main functional units: electrophysiological mapping (EP mapping unit) 140 (which is also referred to herein as data acquisition device 140), ablation module 150, pacing module 160, imaging and/or navigation system 70, and computer or computing device 300. Data acquisition, processing and control system 15 comprises data acquisition device 140, ablation module 150, pacing module 160, control interface 170 and computer or computing device 300. In one embodiment, at least one computer or computing device or system 300 is employed to control the operation of one or more of systems, modules and devices 140, 150, 160, 170 and 70. Alternatively, the respective operations of systems, modules or devices 140, 150, 160, 170 and 70 may be controlled separately by each of such systems, modules and devices, or by some combination of such systems, modules and devices.

Instead of being operably connected (e.g., through Bluetooth signals, a LAN or WAN network, or through the cloud), or directly connected, to computing device 300, data acquisition device 140 may be configured to provide as outputs therefrom saved or stored body surface electrogram signals, which can be, by way of example, saved or stored on a hard drive, in a memory, on a USB stick, or other suitable storage device, and where the saved or stored body surface electrogram signals are later or subsequently provided as inputs to computing device 300 for processing and analysis.

Computer or computing device 300 may be configured to receive operator inputs from an input device 320 such as a keyboard, mouse and/or control panel. Outputs from computer may be displayed on display or monitor 324 or other output devices (not shown in FIG. 1B). Computer 300 may also be operably connected to a remote computer or analytic database or server 328. At least each of components, devices, modules and systems 60, 110, 140, 146, 148, 150, 170, 300, 324 and 328 may be operably connected to other components or devices by wireless (e.g., Bluetooth) or wired means. Data may be transferred between components, devices, modules or systems through hardwiring, by wireless means, or by using portable memory devices such as USB memory sticks.

During electrophysiological (EP) mapping procedures, multi-electrode catheter 110 is typically introduced percutaneously into the patient's heart 10. Catheter 110 is passed through a blood vessel (not shown), such as a femoral vein or the aorta, and thence into an endocardial site such as the atrium or ventricle of the heart 10.

It is contemplated that other catheters, including other types of mapping or EP catheters, lasso catheters, pulmonary vein isolation (PVI) ablation catheters (which can operate in conjunction with sensing lasso catheters), ablation catheters, navigation catheters, and other types of EP mapping catheters such as EP monitoring catheters and spiral catheters may also be introduced into the heart, and that additional surface electrodes may be attached to the skin of the patient to record electrocardiograms (ECGs).

When system 100 is operating in an EP mapping mode, multi-electrode catheter 110 functions as a detector of intra-electrocardiac signals, while optional surface electrodes may serve as detectors of surface ECGs. In one embodiment, the analog signals obtained from the intracardiac and/or surface electrodes are routed by multiplexer 146 to data acquisition device 140, which comprises an amplifier 142 and an A/D converter (ADC) 144. The amplified or conditioned electrogram signals may be displayed by electrocardiogram (ECG) monitor 148. The analog signals are also digitized via ADC 144 and input into computer 300 for data processing, analysis and graphical display.

In one embodiment, catheter 110 is configured to detect cardiac activation information in the patient's heart 10, and to transmit the detected cardiac activation information to data acquisition device 140, either via a wireless or wired connection. In one embodiment that is not intended to be limiting with respect to the number, arrangement, configuration, or types of electrodes, catheter 110 includes a plurality of 64 electrodes, probes and/or sensors A1 through H8 arranged in an 8×8 grid that are included in electrode mapping assembly 120, which is configured for insertion into the patient's heart through the patient's blood vessels and/or veins. Other numbers, arrangements, configurations and types of electrodes in catheter are, however, also contemplated. In most of the various embodiments, at least some electrodes, probes and/or sensors included in catheter 110 are configured to detect cardiac activation or electrical signals, and to generate electrocardiograms or electrogram signals, which are then relayed by electrical conductors from or near the distal end 112 of catheter 110 to proximal end 116 of catheter 110 to data acquisition device 140.

Note that in some embodiments of system 100, multiplexer 146 is not employed for various reasons, such as sufficient electrical conductors being provided in catheter 110 for all electrode channels, or other hardware design considerations. In other embodiments, multiplexer 146 is incorporated into catheter 110 or into data acquisition device 140. In still further embodiments, multiplexer 146 is optional or not provided at all, and data acquisition device 140, ablation module 150, and/or pacing module 160 are employed separately and/or operate independently from one another. In addition, in some embodiments computing device may be combined or integrated with one or more of data acquisition device 140, ablation module 150, and/or pacing module 160.

In one embodiment, a medical practitioner or health care professional employs catheter as a roving catheter to locate the site of the location of the source of a cardiac rhythm disorder or irregularity in the endocardium quickly and accurately, without the need for open-chest and open-heart surgery. In one embodiment, this is accomplished by using multi-electrode catheter 110 in combination with real-time or near-real-time data processing and interactive display by computer 300, and optionally in combination with imaging and/or navigation system 70. In one embodiment, multi-electrode catheter 110 deploys at least a two-dimensional array of electrodes against a site of the endocardium at a location that is to be mapped, such as through the use of a Biosense Webster® PENTARAY® EP mapping catheter. The intracardiac or electrogram signals detected by the catheter's electrodes provide data sampling of the electrical activity in the local site spanned by the army of electrodes.

In one embodiment, the electrogram signal data are processed by computer 300 to produce a display showing the locations(s) of the source(s) of cardiac rhythm disorders and/or irregularities in the patient's heart 10 in real-time or near-real-time, further details of which are provided below. That is, at and between the sampled locations of the patient's endocardium, computer 300 may be configured to compute and display in real-time or near-real-time an estimated, detected and/or determined location(s) of the site(s), source(s) or origin)s) of the cardiac rhythm disorder(s) and/or irregularity(s) within the patient's heart 10. This permits a medical practitioner to move interactively and quickly the electrodes of catheter towards the location of the source of the cardiac rhythm disorder or irregularity.

In some embodiments of system 100, one or more electrodes, sensors or probes detect cardiac activation from the surface of the patient's body as surface ECGs, or remotely without contacting the patient's body (e.g., using magnetocardiograms). In another example, some electrodes, sensors or probes may derive cardiac activation information from echocardiograms. In various embodiments of system 100, external or surface electrodes, sensors and/or probes can be used separately or in different combinations, and further may also be used in combination with intracardiac electrodes, sensors and/or probes inserted within the patient's heart 10. Many different permutations and combinations of the various components of system 100 are contemplated having, for example, reduced, additional or different numbers of electrical sensing and other types of electrodes, sensors and/or transducers.

Continuing to refer to FIG. 1B, EP mapping system or data acquisition device 140 is configured to condition the analog electrogram signals delivered by catheter 110 from electrodes A1 through H8 in amplifier 142. Conditioning of the analog electrogram signals received by amplifier 142 may include, but is not limited to, low-pass filtering, high-pass filtering, bandpass filtering, and notch filtering. The conditioned analog signals are then digitized in analog-to-digital converter (ADC) 144. ADC 144 may further include a digital signal processor (DSP) or other type of processor which is configure to further process the digitized electrogram signals (e.g., low-pass filter, high-pass filter, bandpass filter, notch filter, automatic gain control, amplitude adjustment or normalization, artifact removal, etc.) before they are transferred to computer or computing device 300 for further processing and analysis.

As discussed above, in some embodiments, multiplexer 146 is separate from catheter 110 and data acquisition device 140, and in other embodiments multiplexer 146 is combined in catheter 110 or data acquisition device 140.

In some embodiments, the rate at which individual electrogram and/or ECG signals are sampled and acquired by system 100 can range between about 0.25 milliseconds and about milliseconds, and may be about 0.5 milliseconds, about 1 millisecond, about 2 milliseconds or about 4 milliseconds. Other sample rates are also contemplated. While in some embodiments system 100 is configured to provide unipolar signals, in other embodiments system 100 is configured to provide bipolar signals.

In one embodiment, system 100 can include a BARD® LABSYSTEM™ PRO EP Recording System, which is a computer and software driven data acquisition and analysis tool designed to facilitate the gathering, display, analysis, pacing, mapping, and storage of intracardiac EP data. Also in one embodiment, data acquisition device 140 can include a BARD® CLEARSIGN™ amplifier, which is configured to amplify and condition electrocardiographic signals of biologic origin and pressure transducer input, and transmit such information to a host computer (e.g., computer 300 or another computer).

As shown in FIG. 1B, and as described above, in some embodiments system 100 includes ablation module 150, which may be configured to deliver RF ablation energy through catheter 110 and corresponding ablation electrodes disposed near distal end 112 thereof, and/or to deliver RF ablation energy through a different catheter (not shown in FIG. 1B). Suitable ablation systems and devices include, but are not limited to, cryogenic ablation devices and/or systems, radiofrequency ablation devices and/or systems, ultrasound ablation devices and/or systems, high-intensity focused ultrasound (HIFU) devices and/or systems, chemical ablation devices and/or systems, and laser ablation devices and/or systems.

When system 100 is operating in an optional ablation mode, multi-electrode catheter fitted with ablation electrodes, or a separate ablation catheter, is energized by ablation module 150 under the control of computer 300, control interface 170, and/or another control device or module. For example, an operator may issue a command to ablation module 150 through input device 320 to computer 300. In one embodiment, computer 300 or another device controls ablation module 150 through control interface 170. Control of ablation module can initiate the delivery of a programmed series of electrical energy pulses to the endocardium via catheter 110 (or a separate ablation catheter, not shown in FIG. 1B). One embodiment of an ablation method and device is disclosed in U.S. Pat. No. 5,383,917 to Desai et al., the entirety of which is hereby incorporated by reference herein.

In an alternative embodiment, ablation module 150 is not controlled by computer 300, and is operated manually directly under operator control. Similarly, pacing module 160 may also be operated manually directly under operator control. The connections of the various components of system 100 to catheter 110, to auxiliary catheters, or to surface electrodes may also be switched manually or using multiplexer 146 or another device or module.

When system 100 is operating in an optional pacing mode, multi-electrode catheter is energized by pacing module 160 operating under the control of computer 300 or another control device or module. For example, an operator may issue a command through input device 320 such that computer 300 controls pacing module 160 through control interface 170, and multiplexer 146 initiates the delivery of a programmed series of electrical simulating pulses to the endocardium via the catheter 110 or another auxiliary catheter (not shown in FIG. 1B). One embodiment of a pacing module is disclosed in M. E. Josephson et al., in "VENTRICULAR ENDOCARDIAL PACING II, The Role of Pace Mapping to Localize Origin of Ventricular Tachycardia," The American Journal of Cardiology, vol. 50, November 1982.

Computing device or computer 300 is appropriately configured and programmed to receive or access the electrogram signals provided by data acquisition device 140. Computer further configured to analyze or process such electrogram signals in accordance with the methods, functions and logic disclosed and described herein so as to permit reconstruction of cardiac activation information from the electrogram signals. This, in turn, makes it possible to locate with at least some reasonable degree of precision the location of the source of a heart rhythm disorder or irregularity. Once such a location has been discovered, the source may be eliminated or treated by means that include, but are not limited to, cardiac ablation.

In one embodiment, and as shown in FIG. 1B, system 100 also comprises a physical imaging and/or navigation system 70. Physical imaging and/or navigation device 60 included in system 70 may be, by way of example, a 2- or 3-axis fluoroscope system, an ultrasonic system, a magnetic resonance imaging (MRI) system, a computed tomography (CT) imaging system, and/or an electrical impedance tomography EIT) system. Operation of system 70 be controlled by computer 300 via control interface 170, or by other control means incorporated into or operably connected to imaging or navigation system 70. In one embodiment, computer or another computer triggers physical imaging or navigation system 60 to take "snap-shot" pictures of the heart 10 of a patient (body not shown). A picture image is detected by a detector 62 along each axis of imaging, and can include a silhouette of the heart as well as a display of the inserted catheter 110 and its electrodes A1-H8 (more about which is said below), which is displayed on imaging or navigation display 64. Digitized image or navigation data may be provided to computer 300 for processing and integration into computer graphics that are subsequently displayed on monitor or display 64 and/or 324.

In one embodiment, system 100 further comprises or operates in conjunction with catheter or electrode position transmitting and/or receiving coils or antennas located at or near the distal end of an EP mapping catheter 110, or that of an ablation or navigation catheter 110, which are configured to transmit electromagnetic signals for intra-body navigational and positional purposes.

In one embodiment, imaging or navigation system 70 is used to help identify and determine the precise two- or three-dimensional positions of the various electrodes included in catheter 110 within patient's heart 10, and is configured to provide electrode position data to computer 300. Electrodes, position markers, and/or radio-opaque markers can be located on various portions of catheter 110, mapping electrode assembly 120 and/or distal end 112, or can be configured to act as fiducial markers for imaging or navigation system 70.

Medical navigation systems suitable for use in the various embodiments described and disclosed herein include, but are not limited to, image-based navigation systems, model-based navigation systems, optical navigation systems, electromagnetic navigation systems (e.g., BIOSENSE® WEBSTER® CARTO® system), and impedance-based navigation systems (e.g., the St. Jude® ENSITE™ VELOCITY™ cardiac mapping system), and systems that combine attributes from different types of imaging AND navigation systems and devices to provide navigation within the human body (e.g., the MEDTRONIC® STEALTHSTATION® system).

In view of the structural and functional descriptions provided herein, those skilled in the art will appreciate that portions of the described devices and methods may be configured as processes, methods, data processing systems, and/or computer methods. Accordingly, these portions of the devices and methods described herein may take the form of a hardware embodiment, a software embodiment, or an embodiment combining software and hardware, such as shown and described with respect to computer system 300 illustrated in FIG. 1B. Furthermore, portions of the devices and methods described herein may be a process or method stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, processes, and systems. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in an individual block, plurality of blocks, or block diagram.

In this regard, FIG. 1B illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, and/or transform sensor or electrode data and image data associated with the analysis of cardiac electrical activity and the carrying out of the combined electrophysiological mapping and analysis of the patient's heart 10 and ablation therapy delivered thereto.

Computer system 300 can be implemented on one or more general purpose computer systems or networked computer systems, embedded computer systems, routers, switches, server devices, client devices, various intermediate devices/nodes or standalone computer systems. Additionally, computer system 300 or portions thereof may be implemented on various mobile devices such as, for example, a personal digital assistant (PDA), a laptop computer and the like, provided the mobile device includes sufficient processing capabilities to perform the required functionality.

In one embodiment, computer system 300 includes processing unit 301 (which may comprise a CPU, controller, microcontroller, processor, microprocessor or any other suitable processing device), system memory 302, and system bus 303 that operably connects various system components, including the system memory, to processing unit 301. Multiple processors and other multi-processor architectures also can be used to form processing unit 301. System bus 303 can comprise any of several types of suitable bus architectures, including a memory bus or memory controller, a peripheral bus, or a local bus. System memory 302 can include read only memory (ROM) 304 and random access memory (RAM) 305. A basic input/output system (BIOS) 306 can be stored in ROM 304 and contain basic routines configured to transfer information and/or data among the various elements within computer system 300.

Computer system 300 can include a hard disk drive 303, a magnetic disk drive 308 (e.g., to read from or write to removable disk 309), or an optical disk drive 310 (e.g., for reading CD-ROM disk 311 or to read from or write to other optical media). Hard disk drive 303, magnetic disk drive 308, and optical disk drive 310 are connected to system bus 303 by a hard disk drive interface 312, a magnetic disk drive interface 313, and an optical drive interface 314, respectively. The drives and their associated computer-readable media are configured to provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the devices and methods described and disclosed herein.

A number of program modules may be stored in drives and RAM 303, including operating system 315, one or more application programs 316, other program modules 313, and program data 318. The application programs and program data can include functions and methods programmed to acquire, process and display electrical data from one or more sensors, such as shown and described herein. The application programs and program data can include functions and methods programmed and configured to process data acquired from a patient for assessing heart function and/or for determining parameters for delivering a therapy and/or assessing heart function, such as shown and described herein.

A health care provider or other user may enter commands and information into computer system 300 through one or more input devices 320, such as a pointing device (e.g., a mouse, a touch screen, etc.), a keyboard, a microphone, a joystick, a game pad, a scanner, and the like. For example, the user can employ input device 320 to edit or modify the data being input into a data processing method (e.g., only data corresponding to certain time intervals). These and other input devices 320 may be connected to processing unit 301 through a corresponding input device interface or port 322 that is operably coupled to the system bus, but may be connected by other interfaces or ports, such as a parallel port, a serial port, or a universal serial bus (USB). One or more output devices 324 (e.g., display, a monitor, a printer, a projector, or other type of display device) may also be operably connected to system bus via interface 326, such as through a video adapter.

Computer system 300 may operate in a networked environment employing logical connections to one or more remote computers, such as remote computer 328. Remote computer 328 may be a workstation, a computer system, a router, or a network node, and may include connections to many or all the elements described relative to computer system 300. The logical connections, schematically indicated at 330, can include a local area network (LAN) and/or a wide area network (WAN).

When used in a LAN networking environment, computer system 300 can be connected to a local network through a network interface or adapter 332. When used in a WAN networking environment, computer system 300 may include a modem, or may be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

Figure 2A:
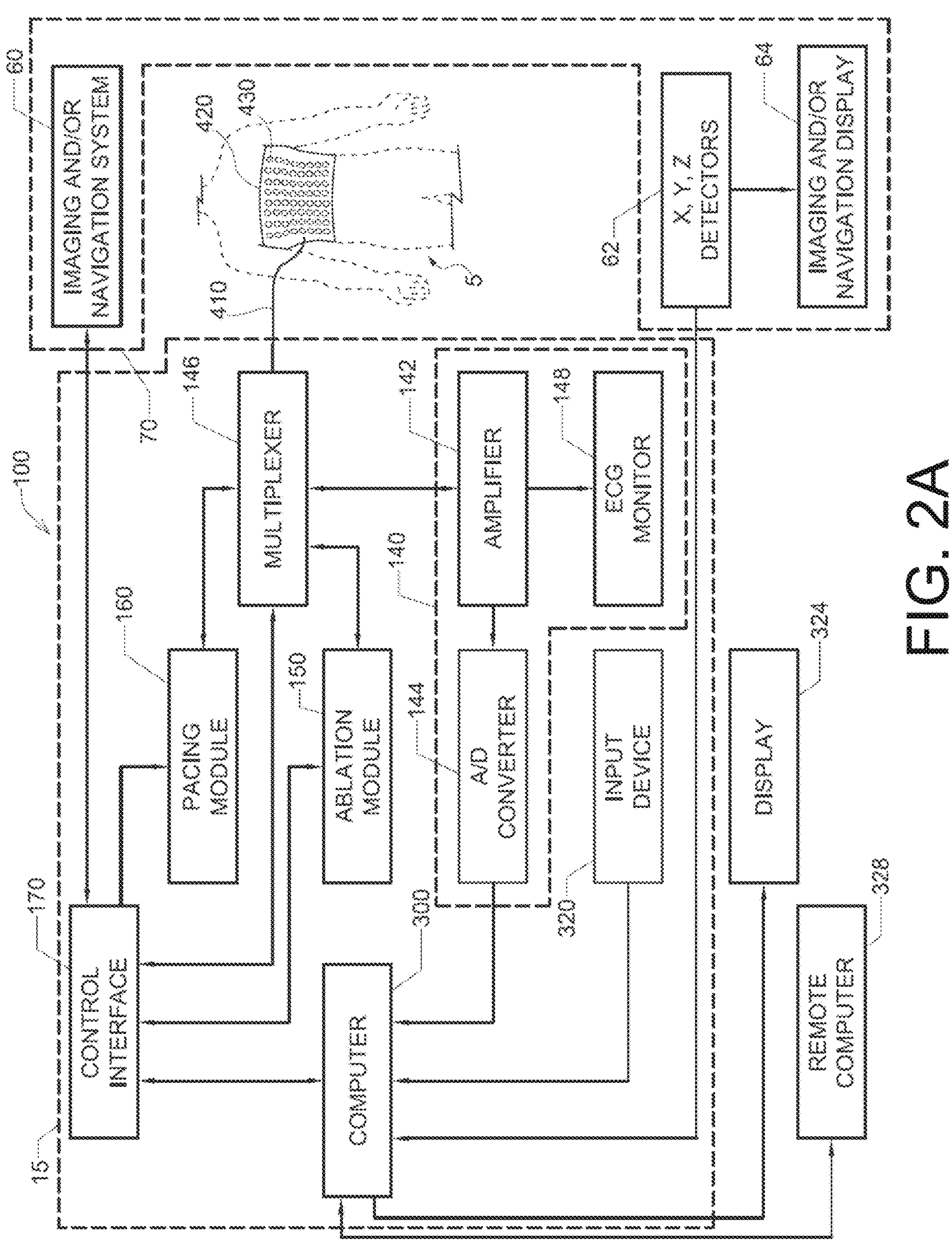
FIG. 2A shows one embodiment of an intra-cardiac imaging and/or navigation system 100.
Figure 2B:
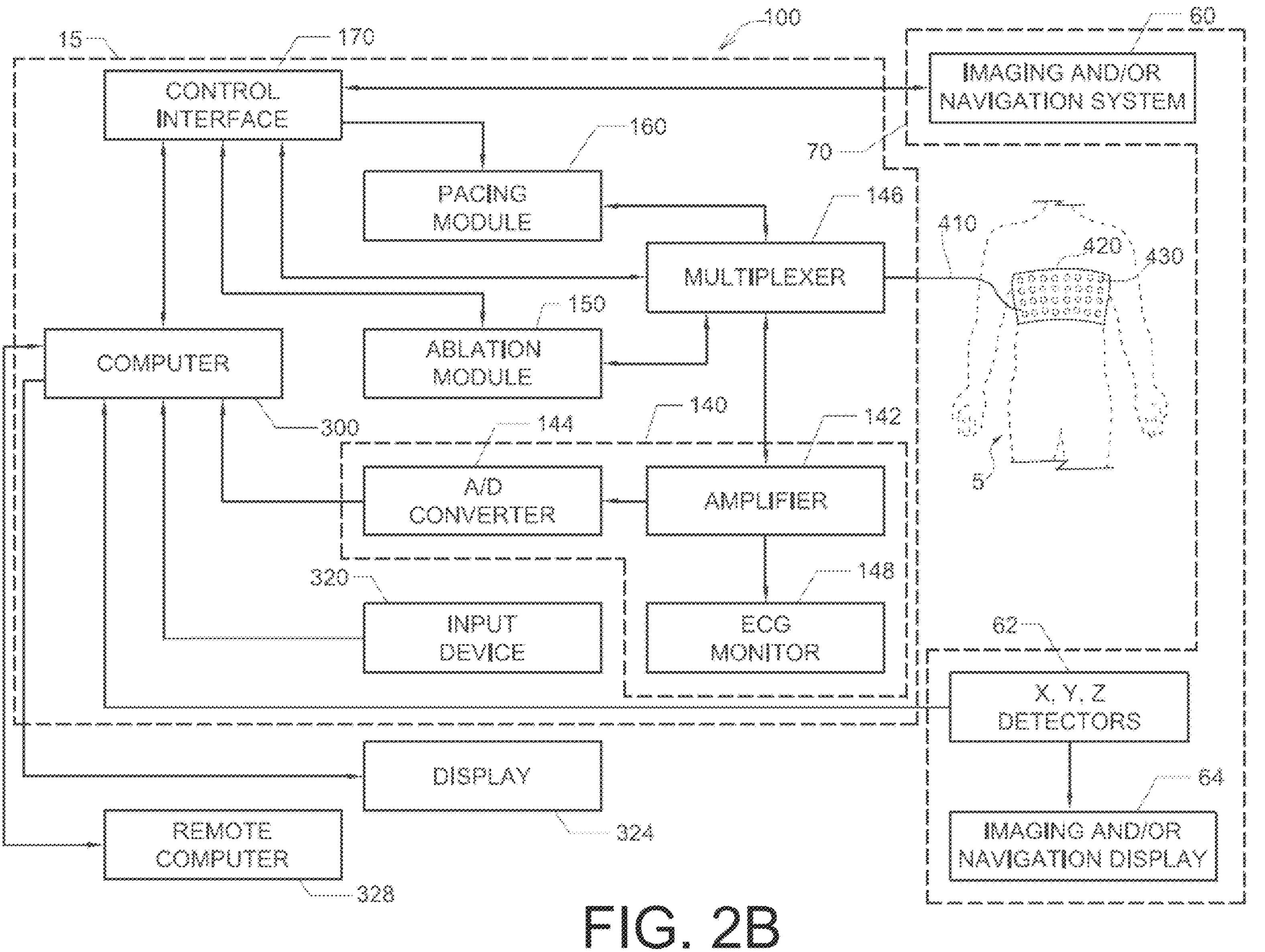
FIG. 2B shows one embodiment of a body surface imaging and/or navigation system.
Figure 3B:
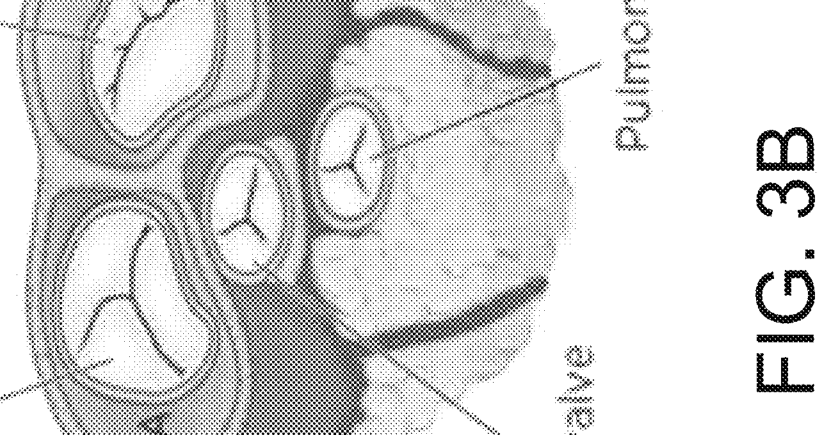
FIGS. 3A and 3B show diagrams illustrating various portions of a human heart.
Figure 3A:
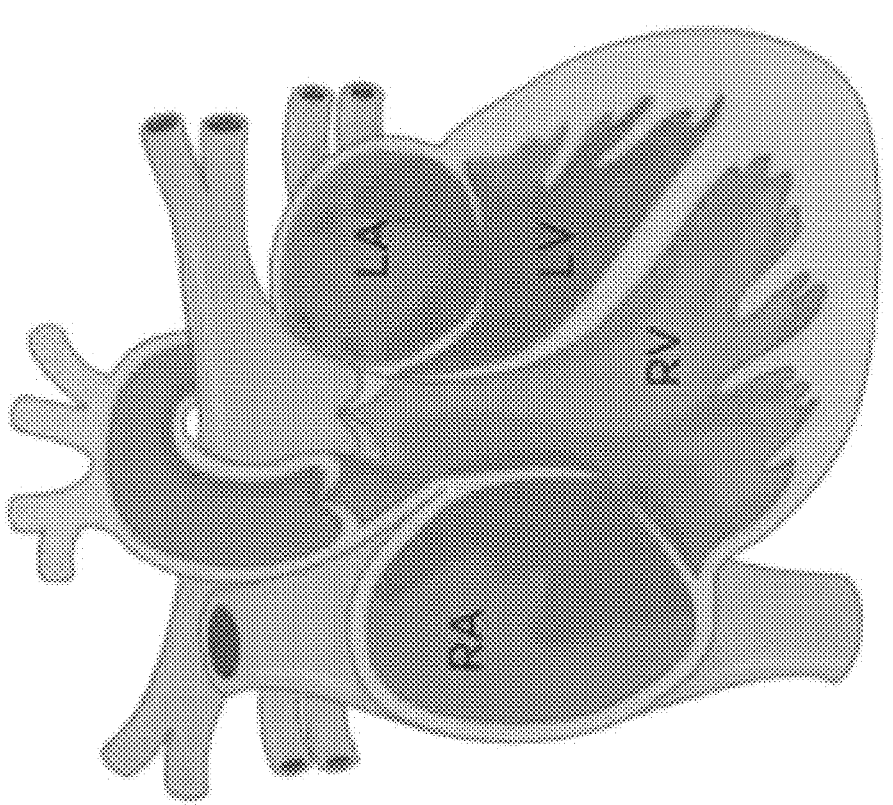
Figures 4A, 4B:
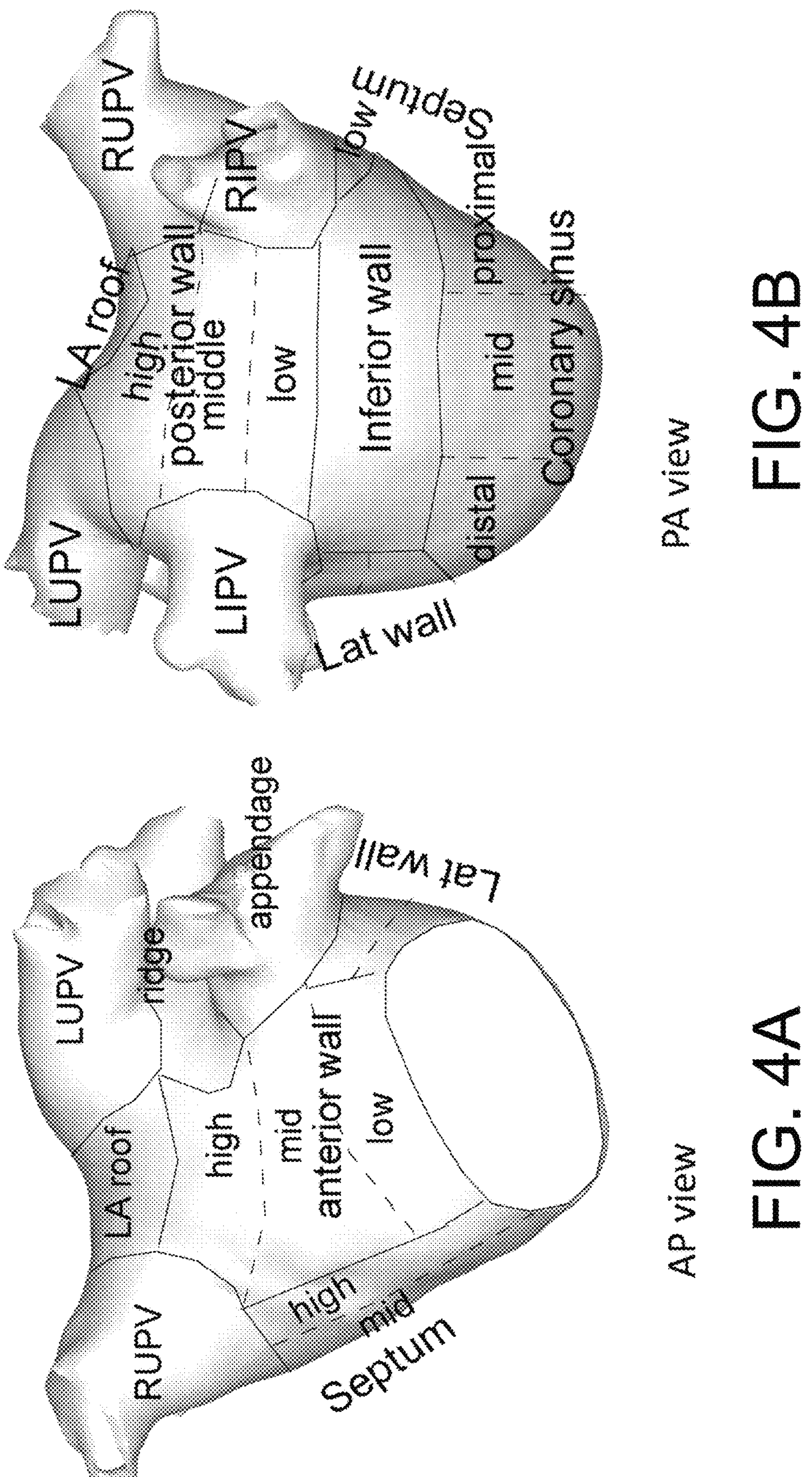
FIGS. 4A and 4B show diagrams illustrating various further portions of a human heart.

Referring now to FIGS. 2A and 2B, there are shown and illustrated various aspects of extracorporeal or body surface electrode EGF systems, devices, components, and methods, which may be employed, by way of non-limiting example, to pre-screen AF patients as described above, or as diagnostic tools for determining whether a patient has AF or AT before more complicated, involved, invasive, and/or time-consuming procedures might be employed (e.g., employing an intra-cardiac basket catheter to map a patient's atrium).

FIGS. 2A and 2B illustrate two different embodiments of a combined extracorporeal body surface electrode EGF and/or cardiac electrophysiological mapping (EP), pacing and ablation system 100. System 100 shown in FIGS. 2A and 2B shares many aspects and features with system 100 shown in FIG. 1B, where certain portions thereof may be interchanged, such as, by way of example, intra-cardiac pacing or ablation catheter 110 with external extracorporeal electrode vest 420, or may be removed, such as, by way of example, ablation module 150, pacing module 160, etc., depending of course on the particular application at hand. There is no need to repeat all the descriptions of the portions of systems 100 and 300 that are described above in connection with FIG. 1B, but that are shown in FIGS. 2A and 2B.

In FIGS. 2A and 2B there is shown a patient 5 wearing a body surface electrode vest comprising a plurality of body surface electrodes 430, which are operably connected through electrical connection 410 to multiplexer 146, and thence to modules 140 and 300. Body surface electrodes 430 are configured to sense ECGs or body surface electrogram signals originating from the patient's heart. Module 140 is configured to receive such ECGs or electrogram signals through electrical connection or cable 410, and to condition such signals for further processing by computer 300. In some embodiments, electrical connection or cable 410 is replaced by a wireless connections, such as BLUETOOTH® connection.

In FIG. 2A, there are shown 64 body surface electrodes 430 mounted on the anterior portion of vest 420, which in turn is worn on or attached to the thorax of patient 5. In some embodiments, another 64 body surface electrodes 430 may be mounted on the posterior surface of vest 420 (not shown in FIG. 2A). Other numbers and configurations of body surface electrodes are also contemplated, such as individual patches, multiple or interconnected patches, patches and electrodes configured to cover only certain tailored portions of a patient's torso determined, calculated, or known to provide locations for sensing optimum heart signals, and numbers of electrodes ranging, by way of non-limiting example, between 1 electrode and electrodes, 4 electrodes, 8 electrodes, 12 electrodes, 16 electrodes, 24 electrodes, 36 electrodes, 48 electrodes, 64 electrodes, 72 electrodes, 96 electrodes, 128 electrodes, 256 electrodes, 512 electrodes, and 1,024 electrodes.

Some examples of current manufacturers of cardiac monitoring patches include: (a) iRhythm® and their Zio XT® and Zio AT® Patch product offerings; (b) the Bardy Dx® Carnation Ambulatory Monitor (CAM™), and (c) the NUVANT® Mobile Cardiac Telemetry (MCT) Monitor, which communicates wirelessly with a cellular device. See, for example: (1) U.S. Pat. No. 10,123,703 entitled "Health monitoring apparatus with wireless capabilities for initiating a patient treatment with the aid of a digital computer" to Bardy et al. ("the '703 patent"); (2) U.S. Pat. No. 10,299,691 entitled "Wearable monitor with arrhythmia burden evaluation" to Hughes et al. ("the '691 patent"); (3) U.S. Pat. No. 10,772,522 entitled "Disposable biometric patch device" to Zadig, and (4) "Cardiac Ambulatory Monitoring: New Wireless Device Validated Against Conventional Holter Monitoring in a Case Series" to Murali et al., Front. Cardiovasc. Med., 30 Nov. 2020 (https://doi.org/10.3389/fcvm.2020.587945) describing the SmartCardia® wearable cardiac monitoring patch ("the Murali paper"). Those skilled in the art will realize that certain aspects and features disclosed and described in in the '703 patent, the '691 patent, the '522 patent, and the Murali paper can be employed in, or adapted and modified for use in, the systems, devices, components, and methods described and disclosed herein. The '703 patent, the '691 patent, the '522 patent, and the Murali paper incorporated by reference herein, each in its respective entirety. Apple iWatch®, FitBit®, Galaxy Watch3®, and Galaxy Watch Active2® are examples of watch or watch-like devices configured to acquire cardiac data from the wearer, such as ECGs, blood pressure, heart rate, etc. Such wearable devices likewise contain certain aspects and features that can be employed in, or adapted and modified for use in, the systems, devices, components, and methods described and disclosed herein.

In the example of FIG. 2B, there are shown 32 body surface electrodes 430 mounted on the anterior portion of vest 420, which in turn is worn on or attached to the thorax of patient 5. In some embodiments, by way of non-limiting example, another 32 body surface electrodes may be mounted on a posterior surface of vest 420 (not shown in FIG. 2A).

Continuing to refer to FIGS. 2A and 2B, any suitable number of body surface electrodes may be employed in system 100. Generally the more body surface electrodes 430 employed the better so as to improve resolution and avoid, for example, spatial aliasing of electrical signals originating from patient's heart 10 arriving at the surface of the patient's thorax. Other numbers, arrangements, configurations, and types of body surface electrodes are also contemplated, however. In some embodiments, at least some body surface electrodes 430 and vest 420 are together configured to detect cardiac activation or electrical signals, and to generate electrocardiograms or body surface electrogram signals, which are then relayed by electrical conductors in cable 410 from the individual electrodes 430 to data acquisition device 140.

It is further contemplated that body surface electrodes 430 may be mounted, attached or coupled to the patient's thorax by means other than a vest, such as by patches, electrode strips, individually, or by other means known in the art. For example, electrode strips manufactured by Goltec GmbH of Cremlingen, Germany can be used. Carbon and metal body surface electrode strips are available from Goltec GmbH. Carbon electrode strips have the advantage of being radio-translucent, i.e., being transparent or substantially transparent during X-ray imaging.

Electrodes may be provided only on the anterior portion of the patient's thorax, only on the posterior portion of the patient's thorax, on side or lateral portions of the patient's thorax, or on any suitable combination of anterior, posterior and/or lateral portions of the patient's thorax.

Continuing to refer to FIGS. 2A and 2B, and as mentioned above, electrodes 430 are configured to sense electrical activity originating in patient's heart 10. In addition to sensing electrodes 430, other types of devices and/or transducers, such as ground electrodes, navigation patches, position markers, or other devices may be configured to operate in conjunction with, be incorporated into, or form a portion of vest 420, electrodes 430, and/or system 10. Electrodes 430 may be reusable or disposable, unipolar or bipolar, and may be configured for use with MRT/MRI, X-Ray, and/or CAT scanning imaging systems or other types of imaging systems 60. Imaging and/or navigation system 60 may be employed used to help identify and determine the precise positions of the various electrodes 430 or position markers included in vest 430. Gels, adhesives, and liquids may be employed to improve electrical coupling of electrodes 430 with the patient's body, as is well known in the art.

Still referring to FIGS. 2A and 2B, electrodes 430 configured to sense electrical activity originating in patient's heart 10 may also be individual or interconnected cardiac monitoring patches, incorporated (or not) into a wearable structure such as a vest or band. Electrodes 430 may also form portions of standard or customized 1-lead ECG monitoring leads (which typically use 1 electrode on the torso), 3-lead ECG monitoring leads (which typically use 3 electrodes on the torso), 5-lead ECG monitoring leads (which typically use 5 electrodes on the torso), and/or 12-lead ECG monitoring leads (which typically use 10 electrodes on the torso and limbs). Cardiac monitoring patches and ECG monitoring leads may have electrodes attachable to a human torso, legs or other portions of the body using adhesives suitable for that purpose, and may also comprise circuitry required to telemeter or send data therefrom via BLUETOOTH or WiFi to system 100, eliminating the need for wired connections between electrodes 430 and system 100. Such circuitry may also be configured to receive instructions, data, and programs wirelessly from system 100 or another source.

In addition to sensing electrodes 430, other types of devices and/or transducers, such as ground electrodes, navigation patches, position markers, or other devices may be configured to operate in conjunction with, be incorporated into, or form a portion of vest 420, electrodes 430, and/or system 10. Electrodes 430 may be reusable or disposable, unipolar or bipolar, and may be configured for use with MRT/MRI, X-Ray, and/or CAT scanning imaging systems or other types of imaging systems 60.

Figure 28:
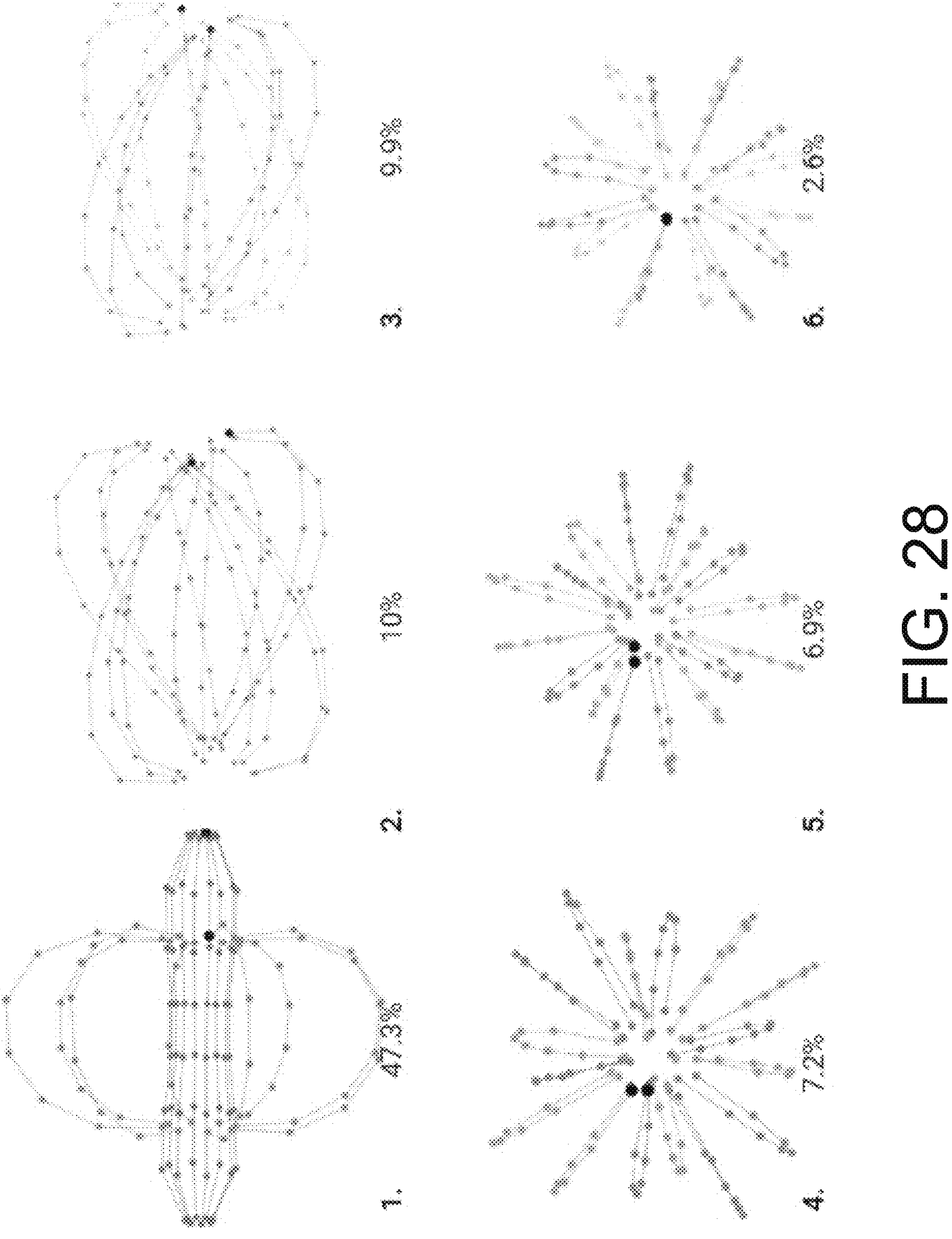
FIG. 28 shows the first six dimensions of one embodiment of an SSM.

Note that in some embodiments, system 100 of FIGS. 2A and 2B may not include multiplexer 146, ablation module 150, pacing module 160, imaging and/or navigation system, 60, or other modules or components shown in FIGS. 2A and 28. Among other things, the embodiments of system 100 shown in FIGS. 2A and 2B are configured to detect and reconstruct cardiac activation information acquired from a patient's heart relating to cardiac rhythm disorders and/or irregularities, and is further configured to detect and discover the location of the source of such cardiac rhythm disorders and/or irregularities with enhanced precision relative to prior art techniques using body surface electrodes 430. In some embodiments, system 100 is further configured to treat the location of the source of the cardiac rhythm disorder or irregularity, for example by ablating the patient's heart at the detected source location.

The embodiment of system 100 shown in FIGS. 2A and 2B comprises five main functional units: electrophysiological mapping (EP mapping unit) 140 (which is also referred to herein as data acquisition device 140), ablation module 150, pacing module 160, imaging and/or navigation system 70, and computer or computing device 300. Data acquisition, processing and control system 15 comprises data acquisition device 140, ablation module 150, pacing module 160, control interface 170 and computer or computing device 300. In one embodiment, at least one computer or computing device or system 300 is employed to control the operation of one or more of systems, modules and devices 140, 150, 160, 170 and 70. Alternatively, the respective operations of systems, modules or devices 140, 150, 160, 170 and 70 may be controlled separately by each of such systems, modules and devices, or by some combination of such systems, modules and devices.

Computer or computing device 300 may be configured to receive operator inputs from an input device 320 such as a keyboard, mouse and/or control panel. Outputs from computer may be displayed on display or monitor 324 or other output devices (not shown in FIGS. 2A and 2B). Computer 300 may also be operably connected to a remote computer or analytic database or server 328. At least each of components, devices, modules and systems 60, 110, 140, 146, 148, 150, 170, 300, 324 and 328 may be operably connected to other components or devices by wireless (e.g., BLUETOOTH) or wired means. Data may be transferred between components, devices, modules or systems through hardwiring, by wireless means, or by using portable memory devices such as USB memory sticks.

During body surface EP mapping or EGF analysis procedures, and as described above, body surface electrodes 430 are positioned on the thorax of patient 5, and by way of example may be mounted on a vest 420 that is configured to place individual electrodes 430 in predetermined positions on the patient's body. These predetermined electrode positions can also be provided to imaging and/or navigation system 60 and/or to computer 300 as a data file so that the spatial positions of body surface electrodes 430 are known (at least approximately), and so that EGF analysis can be carried out accordingly as described above in connection with intra-cardiac EGF analysis (e.g., as described above in connection with FIGS. 1B through 10(*d*)).

When system 100 of FIGS. 2A and 2B is operating in an EP mapping or EGF mode, body surface electrodes 430 function as detectors of electrocardiographic signals. In one embodiment, the analog signals obtained from body surface electrodes 430 are routed by multiplexer 146 to data acquisition device 140, which comprises an amplifier 142 and an A/D converter (ADC) 144. The amplified or conditioned electrogram signals may be displayed by electrocardiogram (ECG) monitor 148. The analog signals are also digitized via ADC 144 and input into computer 300 for data processing, EGF analysis and graphical display (as described above).

Note that in some embodiments of system 100 shown in FIGS. 2A and 2B, and as described above, multiplexer 146 may not form a portion of system 100. In addition, in some embodiments computing device 300 may be combined or integrated with one or more of data acquisition device 140, ablation module 150, and/or pacing module 160.

Biosignal-Based Navigation

We now describe a completely different and novel approach to the problem of navigating an intra-cardiac catheter inside the human heart, and determining its position therein, which employs a purely biosignal-based navigation system that does not require the use of additional expensive and complicated navigation hardware and software systems, devices and components. In one embodiment, the biosignals employed for navigation and catheter/electrode position determination are QRS- and/or QRST-complexes originating from the lower heart chambers (ventricles). The underlying hypothesis is that the QRS-complexes and/or QRST complexes appearing in intracardiac EGMs are unique for each location in the atrium, which therefore allows location information to be extracted from them.

As employed herein, the term "navigation" may include within its scope determination of the position of a catheter, a catheter basket or splines, and/or the individual or selected ones of the electrodes mounted on or attached to the catheter basket or catheter splines inside a human heart, depending on the context. That is, some of the various embodiments of the navigation systems described and disclosed herein not only permit a distal end of a catheter to be accurately guided to one or more desired target locations inside a human heart, but also permit the 3D positions of electrodes mounted on, at or near a distal end of the catheter to be determined with a high degree of accuracy.

Under some circumstances, improved precision of the various embodiments of biosignal-based navigation systems described and disclosed herein, and that have been reduced to actual practice, may be desirable for routine clinical use. Nevertheless, here we describe the actual reduction to practice that has been achieved of several embodiments of biosignal-based navigation and catheter position determination systems, and the various devices, components and methods associated therewith. Further and more precise embodiments of biosignal-based navigation and catheter position determination systems, and the various devices, components and methods associated therewith, are also contemplated and fall within the scope of the present patent application. The navigation and position determination methods described and disclosed herein that have been reduced to actual practice clearly demonstrate that accurate navigation and positioning information can be extracted successfully from intracardiac EGMs using the novel systems and methods described herein.

AF is a condition in which the control of heart rhythm is taken away from the normal sinus node pacemaker by rapid and aberrant electrical activity occurring in different areas within the upper chambers or atria of the heart. This condition can result in rapid and irregular atrial activity and, instead of contracting, the atria quiver chaotically and arrhythmically. The current estimate for the prevalence of AF in the developed world is approximately 1.5-2% of the general population, and is associated with a five-fold risk of stroke, a three-fold incidence of congestive heart failure, and higher mortality. Hospitalization of patients with AF is common.

Cardiac ablation therapy is a surgical procedure that aims to identify and ablate abnormal tissue causing an arrhythmia. The success rate of ablation therapy is highly dependent on the precise removal of the correct tissue. On the one hand, removing too little tissue can cause the arrhythmia to recur and require another procedure. On the other hand, removal of too much tissue can unnecessarily damage the heart. Therefore, accurate localization of the abnormal tissue is necessary to ensure a long-term positive outcome for patients with AF.

In most cases, AF is treated by pharmacological therapies. Among non-pharmacological therapies, cardiac ablation therapy is a common and well established technique. The aim of ablation therapy is to cause myocardial cell injury in a defined and localized manner along the atrial walls. To identify the targets of ablation therapy, the electrical activity of a patient's atrium needs to be understood. Therefore, a catheter with attached electrodes is placed inside one or more atria during a minimally invasive procedure. These electrodes are then used to create an intracardiac EGM by recording the electrical activity inside the atrium. This process is called mapping or electrophysiological (EP) mapping. To map the whole interior atrial surface, the catheter may be placed in multiple positions and intracardiac EGMs recorded. For the placement and navigation of the catheters, fluoroscopy imaging is typically used. The radiation exposure resulting from by the usage of fluoroscopy carries a known medical risk. In recent years non-fluoroscopic three-dimensional (3D) navigation systems have therefore been used to assist in mapping and ablation, which results in a reduction of x-ray exposure. Such 3D navigation systems permit the visualization of the catheter inside the atria.

Unfortunately, known 3D navigation systems have major drawbacks. On the one hand, they require additional hardware which is employed only for the purpose of navigation. To achieve the highest precision, such 3D navigation systems work best with a specific type of catheter, require additional body surface electrode patches on the patient's front and back, and an additional pad mounted underneath the patient table. Also, and importantly, such 3D navigation systems also generate an electromagnetic field which can result in noise and artefacts in the EGM. This is a critical factor, since EGMs are the foundation upon which treatment decisions are made on, and thus accurate and high-fidelity EGMs are important for treatment success. The foregoing negative factors regarding known 3D navigation systems illustrate the significant advantages of extracting accurate and reliable catheter navigation and positioning information from intracardiac EGMs alone. Catheter navigation and positioning information derived from intracardiac EGMs eliminates the need for costly additional hardware, and also helps minimize the introduction of noise into EGMs. To this end, signals emanating from the lower heart chambers (the ventricles), in particular QRS-complexes (and in some embodiments QRST-complexes) are utilized as described and disclosed herein, and as further described in the '249, '605, '246, '291, '346, '163 patent applications.

In recent years, several technologies have been developed to guide ablation to ensure more accurate identification of abnormal tissue. Electroanatomical mapping integrates information of the electrical signal flow with anatomic regions. The main goal of this technique is to visualize the electrical activity of abnormal cells on an anatomy model. An electroanatomical mapping system typically consists of three main components capable of carrying out the following steps, namely: (1) 3D reconstruction of electrophysiological catheters, (2) calculation of activation maps showing the flow of electrical signals from electrograms, and (3) the integration of electroanatomical information with an anatomy model. In particular, the integrated nature of such a system can provide valuable information to an attending physician before and after ablation.

One focus of the work described and disclosed herein is to develop algorithms for foregoing components (1) and (3). For component (2), ABLACON software can be used to extract information regarding the detailed flow of electrical signals from electrogram recordings. For component (1), some of the algorithms described and disclosed herein can be configured to use only biosignals originating from or in the heart to reconstruct a catheter position in 3D space. The advantage of a biosignal-based approach is that the heart and the patient body motion do not introduce errors, unlike impedance-based, magnetic-based, and current-based approaches. In addition, the biosignal-based approach does not require additional hardware, and therefore can be applied retrospectively. As a result, old procedures can be reevaluated and used as data for statistical analysis of the location of abnormal tissue. Furthermore, this data could be used to improve patient outcome prediction. For component (3), segmentations of CT scans can be aligned with reconstructions from component (1) using biological priors. As a result, the activation maps from component (2) can be visualized inside and over the anatomy.

Medical Background—Heart Anatomy and Physiology

The heart is a complex organ whose main function is to pump blood through the body. The heart cavity consists of four chambers shown in FIG. 3A. The two atria, the right atrium (RA) and left atrium (LA) receive blood flowing back from the body. They are separated by a wall called the septum. The two ventricles, the left ventricle (LV) and right ventricle (RV) receive blood from the atria through the tricuspid valve and the mitral valve (see FIG. 3B). From there, the blood is pumped to the lungs and the rest of the body. Each ventricle and atrium can be further subdivided into regions. The anatomy of LA is of particular importance to this work, and therefore the region of the LA is visualized in further detail in FIGS. 4A and 4B, where the LA is divided into 13 regions and visualized from the anteroposterior (AP) and posteroanterior (PA) views. The regions are named: roof, ridge, appendage, lateral wall, anterior wall, septum, left upper pulmonary vein (LUPV), left inferior pulmonary vein (LIPV), posterior wall, inferior wall, coronary sinus, right inferior pulmonary vein (RIPV) and right upper pulmonary vein (RUPV).

Figure 5:
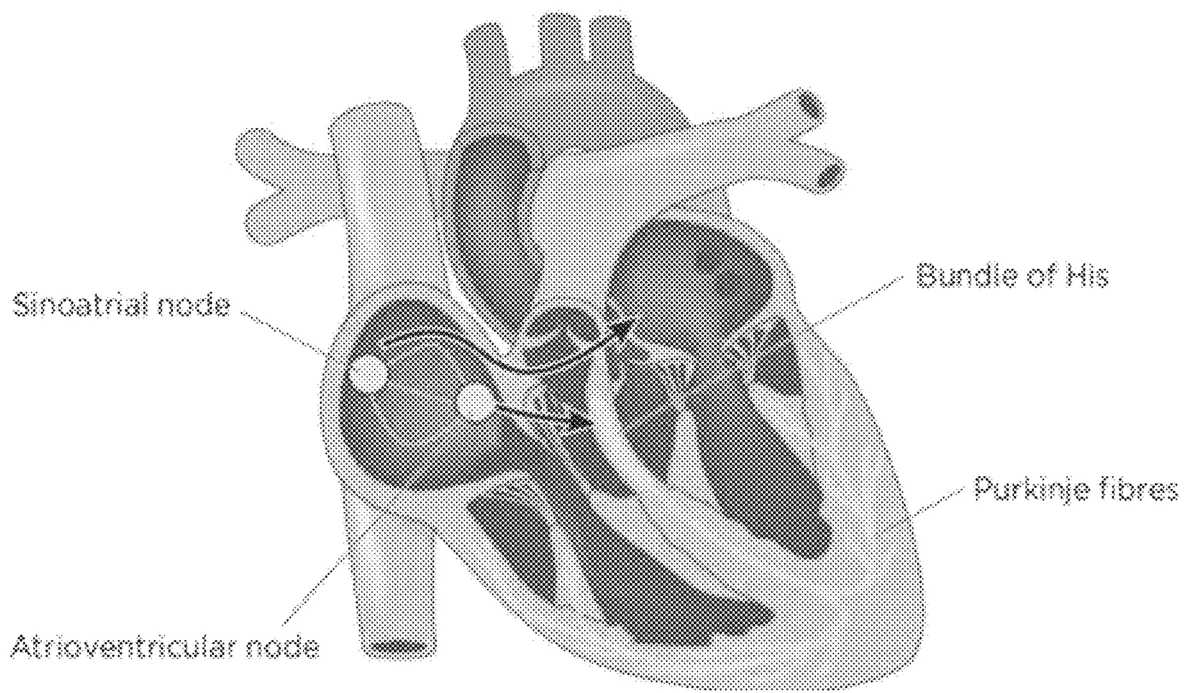
FIG. 5 shows a schematic representation of the electrical conduction system of a human heart.

FIG. 5 illustrates the electrical conduction system of the heart. To pump the blood through the body, the heart contracts. This contraction requires coordination since all muscle cells in the ventricles must be excited simultaneously. In addition, the contraction is performed rhythmically. With further reference to FIG. 5, a heartbeat cycle is initiated by the depolarization of cells in the sinoatrial node in the RA. This sinoatrial node acts as a natural pacemaker and determines the time interval between heartbeats. The excitation propagates to the LA and to the atrioventricular node, which is located in the interatrial septum and is the conduction pathway to the ventricles. From there, the signals are transmitted through the His bundle, a large bundle of specialized tissues. Through the Purkinje fibers, which are distributed throughout the LV and RV, the muscle cells are excited. The result is a strong contraction of the ventricles, which pumps blood to the body.

In AF, coordination of the conduction system is disturbed. The reason for this disturbance can be that atrial cells, that are not located in the sinoatrial node, begin to fire spontaneously, triggering cascades of signal propagation. This can lead to a variety of problems and diseases, such as coronary artery disease and myocardial infarction. Furthermore, AF has been associated with impaired cognitive function and substantial mortality.

Measurement of Cardiac Electrical Activity

Figure 6:
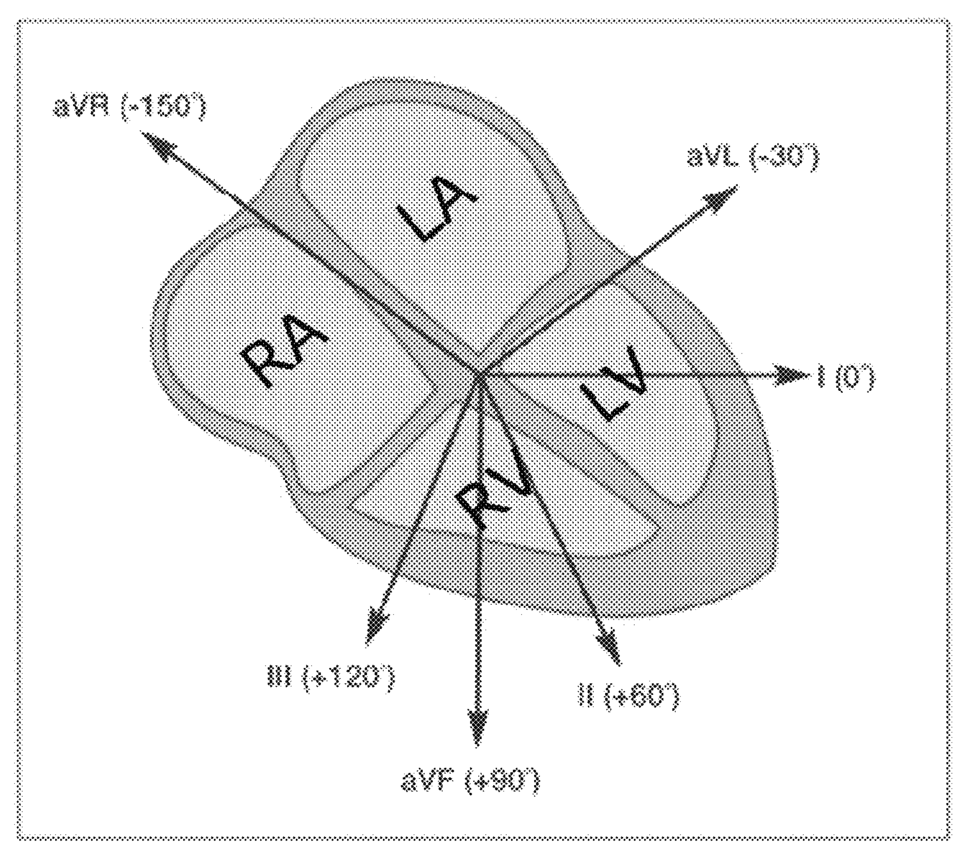
FIG. 6 shows the axes of a 12-lead ECG with respect to a human heart.

The most commonly used non-invasive method for measuring the electrical activity of the heart is the electrocardiogram (ECG). An ECG is recorded using ECG electrodes and ECG leads. One or more electrodes are placed on the surface of the body and record the electrical current. An ECG lead is calculated by analyzing multiple ECG electrodes and refers to the difference in potentials. FIG. 6 shows the axes of a conventional or standard 12-lead ECG. A 12-lead ECG is calculated using ten electrodes placed on the patient's chest, limbs, and arms. The leads are called I, II, III, aVR, aVL, aVF, V1-V6, and each of them provides information about a specific axis through the heart (see FIG. 6). A positive deflection of a lead is measured when the direction of the heart's electrical activity moves in the direction of the lead. If the deflection is negative, the direction of electrical activity moves away from the lead.

Figure 7:
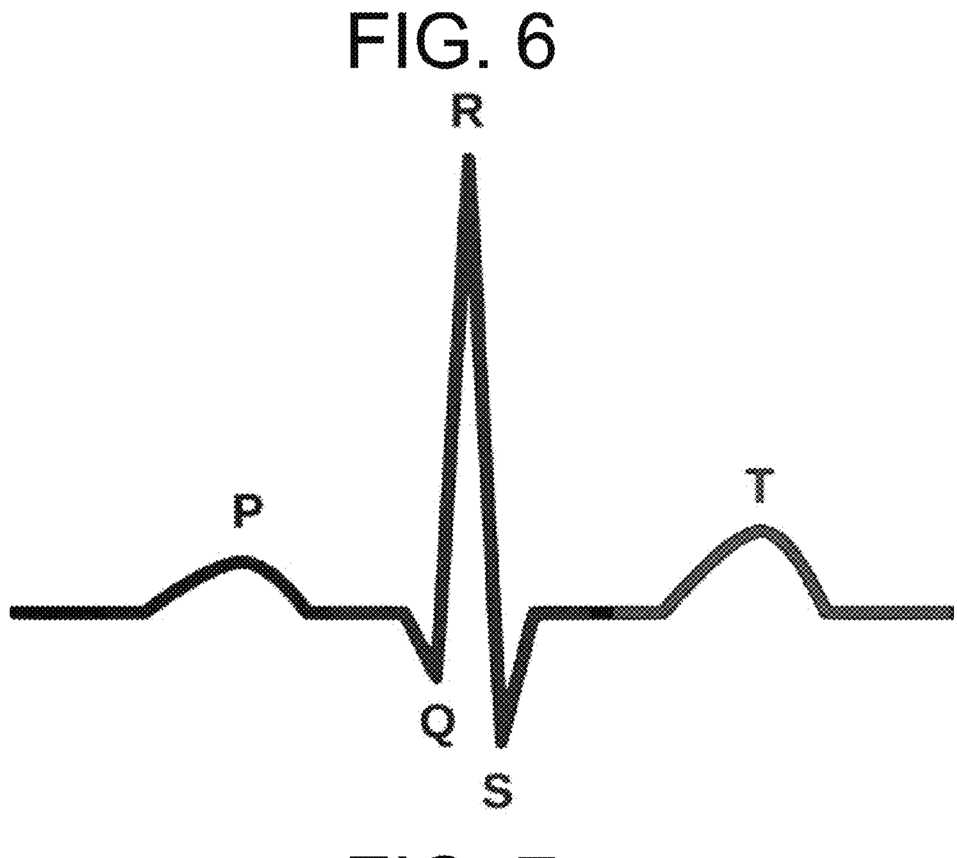
FIG. 7 shows three stages of the electrical activity of a human heart.

A typical signal of the heartbeat can be extracted by combining measurements of the first three leads (see FIG. 7). This signal provides detailed information about one cycle of a heartbeat. The P-wave indicates the depolarization of atrial cells. It starts with the depolarization of the sinoatrial node and ends with the transmission of the signal to the ventricles. This is followed by depolarization of the ventricles, which is indicated by the so-called QRS complex. It consists of a downward deflection Q, followed by a steep upward deflection R and a downward deflection S. The QRS complex typically lasts about 60 to 100 ms. After depolarization of the ventricles, the cells have a repolarization period, which is measured in the T-wave. In FIG. 7, three representative typical stages of the electrical activity of a human heart measured on the body surface are shown: P-wave (indicating atrial depolarization), QRS complex (measuring ventricular depolarization), and T-wave (indicating ventricular repolarization).

Figure 8B:
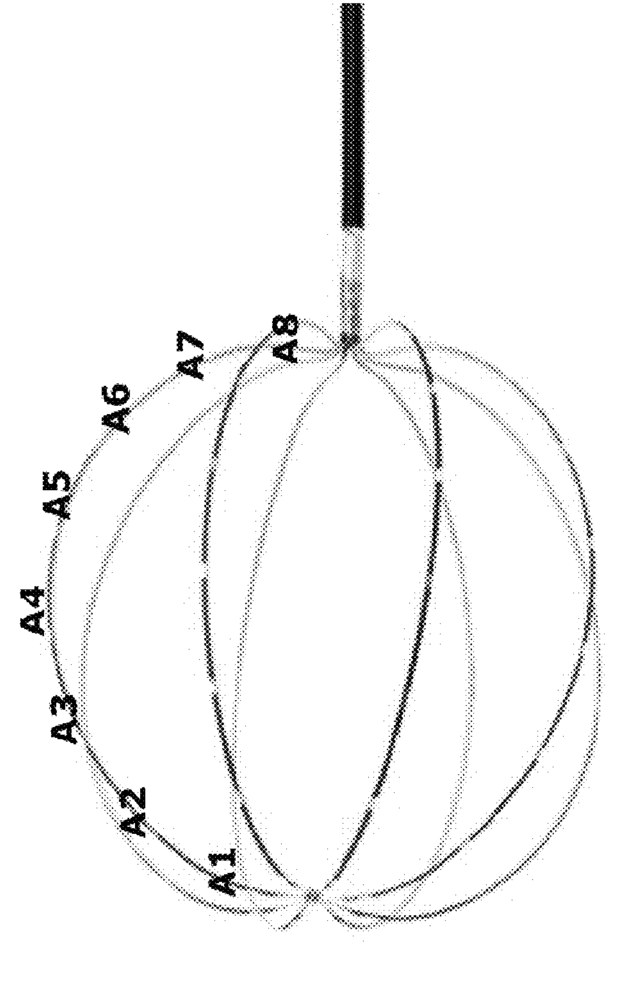
FIGS. 8A and 8B show two views of a 64-electrode basket catheter.
Figure 8A:
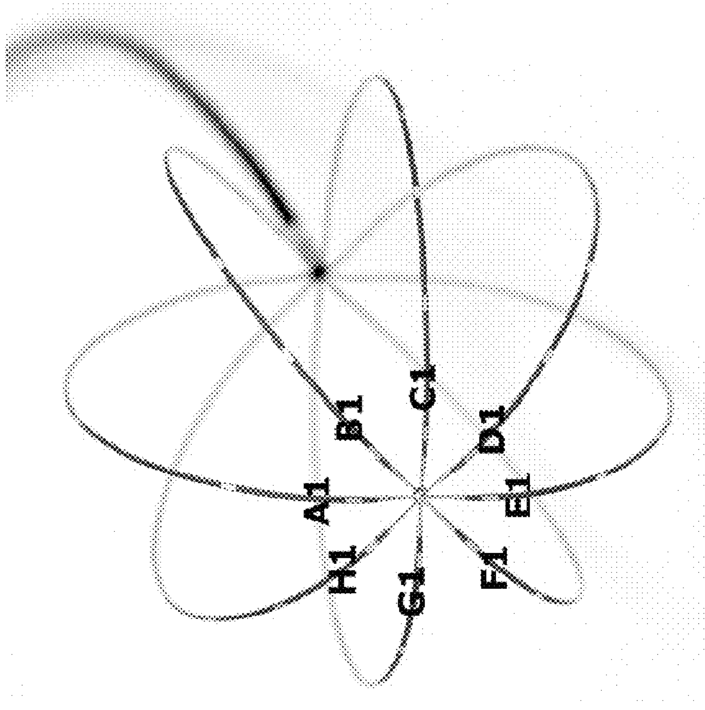

The electrical activity of the heart can also be measured from inside the heart, which is called an intracardiac electrogram (EGM). EGMs are typically obtained using electrodes arranged on a catheter that is inserted into the heart, first into the RA and then through the septum. Such a catheter can also be inserted in the L A. The choice of the catheter is critical. A 64-electrode basket catheter (BC) enables a large coverage of the heart wall. A BC usually has 8 splines, and each spline has 8 electrodes that are equally spaced (see FIGS. 8A and 8B). FIGS. 8A and 8B show conventional labelling of electrodes on a typical 64-electrode BC. The BC should be highly deformable and compressible so that it can be held inside a surrounding introducer or sheath until the distal end of the catheter has been inserted into the heart and the BC can be deployed and expanded.

The main reason for performing an EGM is to obtain more local and detailed information about the depolarization cascade. In patients with AF, EGM recordings can be used to locate atrial cells that interfere with the normal depolarization cycle. The physician can then ablate the tissue.

Electrographic Flow (EGF)

EGM recordings from a 64-electrode BC can be visualized as a map using EGF technology from Ablacon. The software calculates electrographic flow or EGF, which among other things describes the direction and strength of electrical flow across the surface of the BC. An EGF map is particularly useful for the treatment of AF because the locations of spontaneously firing aberrant cells can be determined. These cells are called generally referred to as sources, and typically can be identified in an EGF map as points of high divergence. Rotors are rotating sources that can also be drivers of AF. A distinction is made between passive and active rotors, i.e., an active rotor is a trigger of AF, whereas a passive rotor can be detected, for example, when the BC picks up signals at an entry of a vein.

Figure 9:
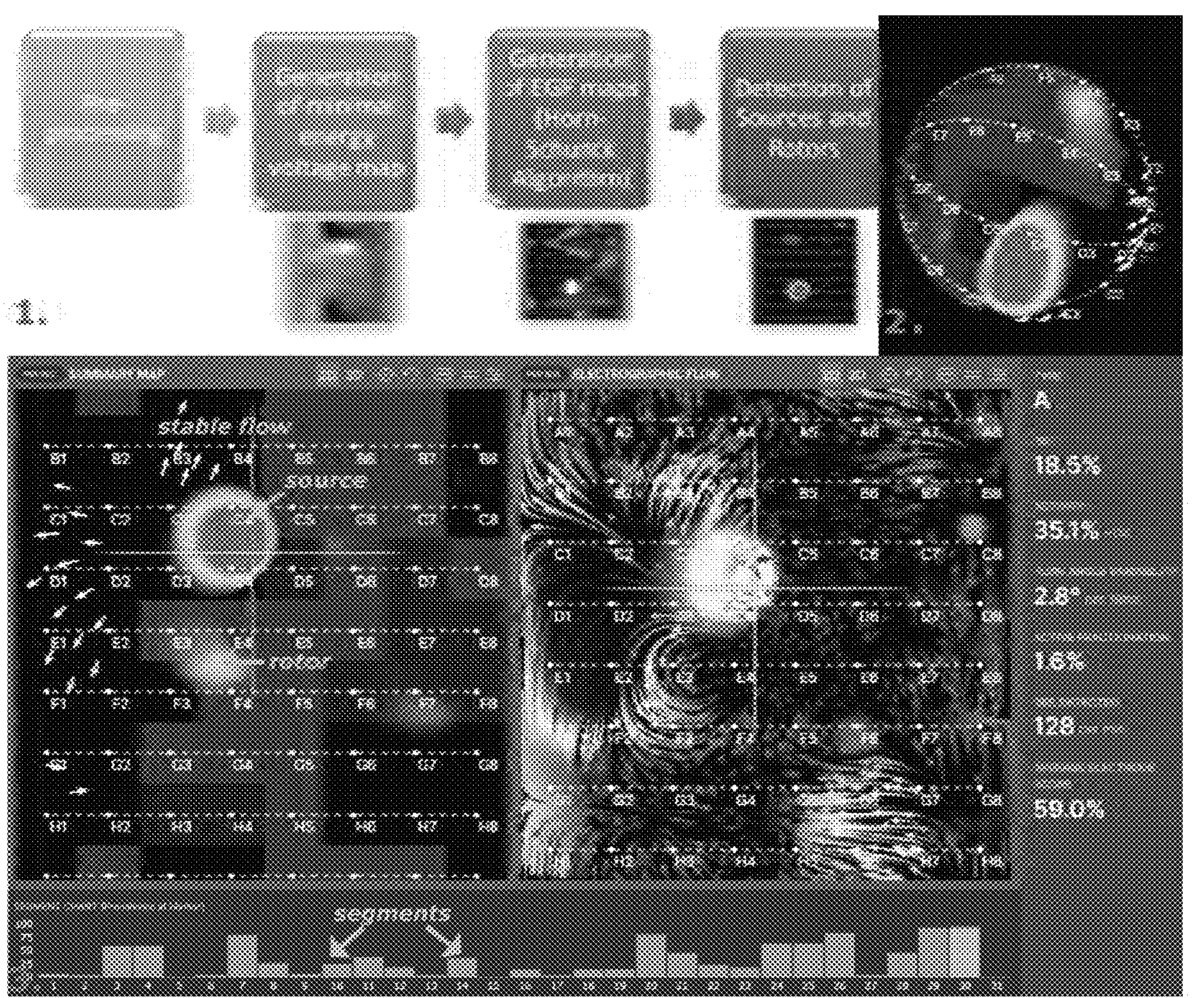
FIG. 9 shows one embodiment of a visualization of an ABLACON EGF algorithm.

FIG. 9 shows one embodiment of four generalized steps carried out by one version of Ablacon EGF software. First, the recorded signals are preprocessed by removing far-field artifacts and normalizing the signal. Then, the signal is divided into 2-second segments and a minimum energy voltage map is calculated for each segment. The subsequent voltage maps are then fed into a Horn-Schnuck algorithm and an EGF map is calculated. On each EGF map, the positions of sources and rotors are determined according to their divergence properties. To combine all the information from a 1-minute recording into a single map, a summary map can be created. The summary map can be configured to present information about how many times a source has been active in all segments. If a source has been active in many segments, it can be classified as a strong source (shown in red in FIG. 9). Also in FIG. 9, rotors are shown in white, and arrows mark the area where flow is consistent in many segments. Light squares indicate a lack of electrode contact. Two-dimensional summary maps and 2D EGF maps can be projected onto a 3D basket model for more intuitive visualization. In FIG. 9, a 2D summary map is projected onto a 3D basket model and the Ablacon user interface displays a summary map and an EGF map for the selected segment. In the summary map of FIG. 9, sources are in red, rotors are in white, and stable flow is indicated by arrows. Light squares represent poor electrode contact.

Machine Learning and Neural Network Architectures

In this section, various neural network (NN) architectures are described, such as a feed forward NN, an autoencoder, a CNN, and a Siamese NN. It will be understood by those skilled in the art, however, that in addition to the embodiments of NNs described explicitly herein, other types and configurations of neural networks may also be employed to carry out the methods described and disclosed herein.

In the general case, an NN is configured to iteratively approximate a function by updating its parameters. In most embodiments of NN, the parameters are updated to minimize a loss function using gradient descent and backpropagation. The smallest units of NN are called neurons and are organized into layers. In a fully connected feed-forward NN, all neurons in one layer are connected to all neurons in the previous and following layers. Each connection has a weight and a bias. In some embodiments, all weights and biases of the NN constitute the trainable parameters of the model, which are updated at each learning step. The input data are divided into training data, validation data and test data. Training data is input to the NN during training, and parameters are turned or modified based on the training data. Validation and test data are used to evaluate how well the NN performs on untrained input data.

An autoencoder model is a very powerful NN for unsupervised learning, and is configured to learn a compressed representation of all input data and identify the most important factors of variation in the data. In some embodiments, the autoencoder comprises two parts, both of which can be fully connected NNs: the encoder E and the decoder D. E compresses all input data x into a vector $\vec{v}\in n$ and D reconstructs the input data x' (see, e.g., FIG. 10). The loss function L is the difference between the original input x and the reconstructed input x' for all input data. The vectors representing the compressed version of IC the input, form what is called the latent space or embedding space. This space is considered meaningful because the distances between the vectors represent a similarity measure for the input data. There can be many extensions to an autoencoder, such as a constrained autoencoder, which applies additional constraints to the latent space. In FIG. 10, there is shown an example of a learned latent space of an autoencoder trained on handwritten digits. Input image x is fed through encoder E and mapped into the latent space. Decoder D then reconstructs x' from the position in the latent space. As it can be seen in the visualization of the latent space, images of the same number which are represented with the same color are grouped together.

A CNN architecture is a special architecture that is optimal for data with a known grid-like topology (e.g., images). Instead of connecting all neurons between layers, only certain neurons are connected. FIGS. 11A and 11B show an example of a connection pattern where one neuron is connected to three neurons in the next layer and all weights are shared between neurons. In FIGS. 11A and 11B, examples of connections of neurons in a fully connected layer and in a convolutional layer are illustrated. In the convolutional layer there are shared weights (red, green, blue) across all neurons and each neuron is only connected to a small neighborhood of neurons in the next layer. Weights can also be thought of as a kernel that slides over the input. For images, this concept has proven very successful, as a kernel with a small number of parameters can detect a particular feature (e.g., an edge) in the entire input image. Some embodiments of CNN architecture can be configured to exhibit many parallels to the biological processes of vision in animals and humans.

A Siamese NN can be configured to learn from very little training data in comparison to many other NN models. A Siamese NN generally uses a high number of shared weights to constrain the number of parameters and thus achieve good generalization. The network consists of two or more identical subnetworks that share weights. Given inputs, it predicts the similarities between the inputs. This similarity value can be used to determine whether the inputs belong to the same class or to a different class. Such a model can be easily extended to detect more classes, and it can also perform well on data from unknown classes.

Rigid Registration 3D object registration refers to the problem of aligning two objects with respect to one another. A transformation t is computed to transform the object $o_1$ so that it is aligned with the object $o_2$. The type of registration is determined by the degrees of freedom of the parametric transformation. A rigid transformation in 3D has six degrees of freedom, three for rotation R and three for translation t. The scale and all angles are preserved in a rigid transformation. Given pairs of corresponding 3D points, the optimal rigid transformation that minimizes the mean squared error can be found using Kabsch's algorithm. First, both objects must be translated so that their centers are at zero. Then, the optimal rotation is calculated using the covariance matrix and a singular value decomposition (SVD). The quality of the solution depends on the noise in the corresponding point pairs.

Figure 12:
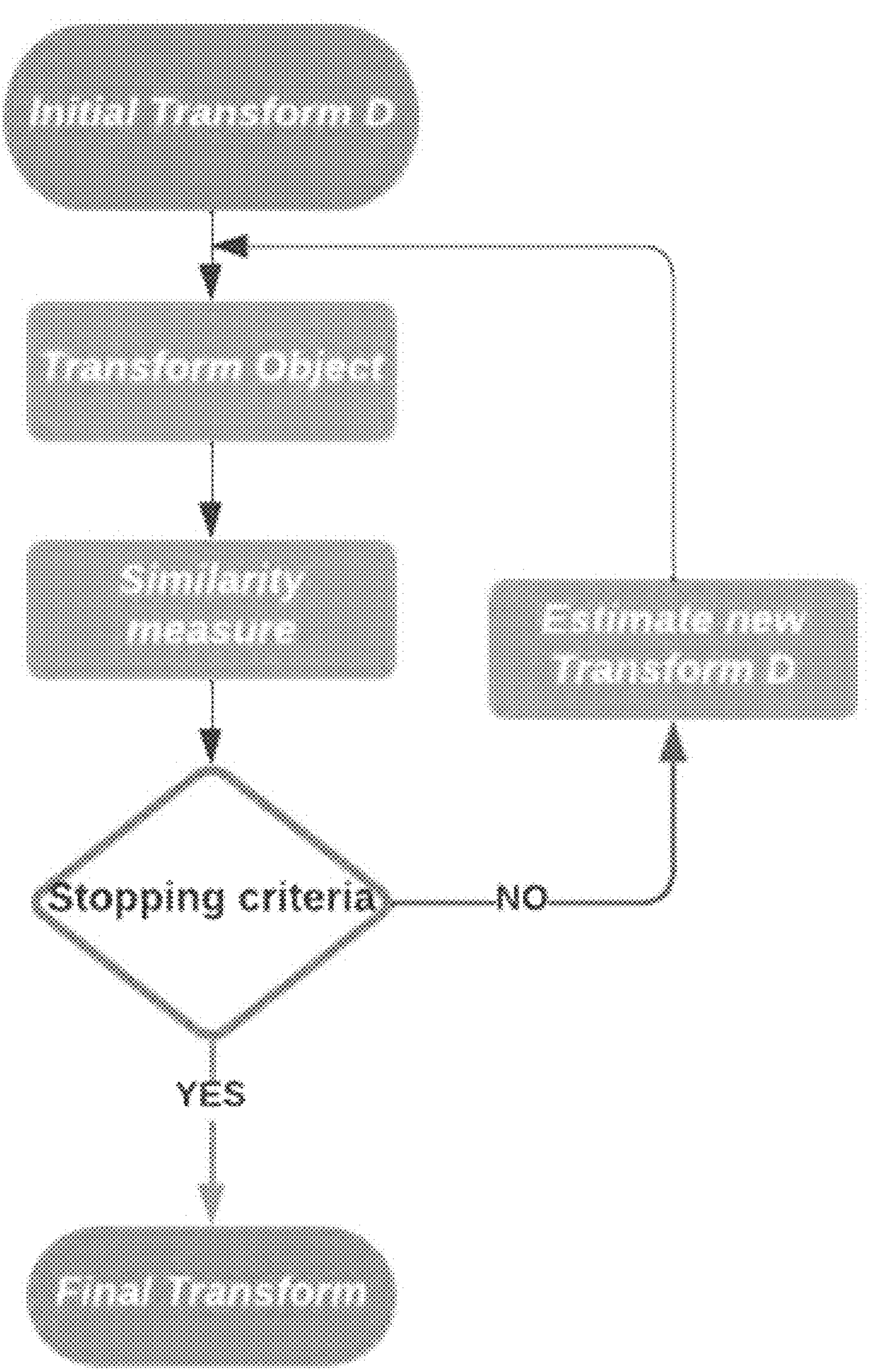
FIG. 12 shows one embodiment of a flow chart of an iterative approach to finding transformational parameters.

There are also iterative approaches to finding the best rigid transformation that do not require corresponding points. Instead, a similarity function is used, which can be based, for example, on comparing the overlap of the objects or color values. One embodiment of such an iterative scheme is shown in FIG. 12, where a flow chart of an iterative approach to find the best transformation parameters D is illustrated.

3D Reconstruction

Various methods have been developed for estimating the spatial position of catheter electrodes in the heart. In the earliest systems, fluoroscopic images were taken during surgery. After each change of position, fluoroscopic images were made that provided the physician with information about the current position of the catheter. However, these systems have mostly been replaced due to high radiation levels. Technologies for magnetic-based 3D reconstructions are implemented in the CARTO3® (Biosense Webster), ENSITE PRECISION® (Abbott) and RHYTHMIA® systems (Boston Scientific). Multiple coils are placed under the operation table. Each coil emits a different low-intensity magnetic field. The strength of the fields can be detected from sensors located on electrodes inside the heart. Distance to coil and strength of the field are inversely propositional to one another. Consequently, the distance to each coil can be estimated and 3D reconstructions displayed. These systems generally require compensation for respiratory and cardiac movement. Magnetic-based systems have been combined with other technologies to improve their performance.

In the CARTO3 system, magnetic-based 3D reconstructions are combined with a current-based approach. For current-based 3D reconstruction, six patches are positioned on the patient, three on the back and three on the chest. Then, the system sends a small current across the catheter electrodes. Each electrode emits current at a unique frequency. Based on the current strength recorded at each of the six patches, an electrode location can be estimated.

In the ENSITE PRECISION system, the magnetic approach is combined with an impedance-based approach. For impedance-based 3D reconstruction, an electrical field is created along three orthogonal axes. For this, three-paired patches are placed on the skin of the patient. The first axis is created by a pair of patches placed at the chest and the back of the patient. Another pair of patches is attached to the back of the neck and the inner left thigh to generate a second axis. The last pair of patches is placed on both sides of the patient. Electrical current is transmitted between the patches and a 3D electrical field is generated with the heart at its center. The electrodes in the heart are configured to record relative voltage in comparison to a reference electrode. This process enables the estimation of the 3D location of electrodes. Due to the nonlinear impedance of the human body, electrode locations can be distorted, and additional compensation may be required.

The accuracy of hybrid magnetic navigation systems is estimated to be less than 1 mm. The accuracy of such systems can be assessed on phantoms, where, e.g., in Bourier et al. point localization performance is estimated to be 0.46±0.17 mm in the CARTO3 system and 0.79±0.83 mm in the ENSITE system.

Biosignal-based 3D reconstruction has been proposed by Denner. The assumption is that at every location in the heart, a unique QRS signal can be recorded. In addition, the more similar two recorded QRS morphologies are to one another, the closer the location of the electrodes. A constraint autoencoder model can be trained for each patient to learn 3D representations of BCs in a 3D space. The constraint in the latent space forces the electrodes to have a similar pairwise distance to each other than the electrodes in an undeformed BC model. As a result, the latent space learns to represent a 3D space, where every position of an electrode is represented with x, y, z values. Compared to CARTO reconstructions, an average electrode distance of 8.8 mm, a deformation value of 6.8 mm, and an error of 5.3 mm for estimating the center of mass has been reported.

Alignment to Anatomy

Electroanatomical systems such as CARTO and EnSite provide the function to fuse or register 3D reconstructions to segmentations of CT or MRI. See Rolf et al. In general, an intraprocedural estimation of the anatomy is done first, which is then registered with the CT/MRI data.

CARTO3 has the following three modules that can achieve registration in different ways: CARTOSound, CARTOMERGE, and CARTOUnivu. In CARTOSound, intracardiac echocardiography is used to extract anatomical information at the start of the procedure. For this, a tiny catheter with an ultrasound sensor is inserted into the heart. The transducer provides 90° sector images with depth control and can generate multiple 2D cross-sections. From these cross-sections, a 3D model can be created, which then can be registered with CT/MRI scans (see Rolf et al.). For CARTOMERGE, an intraprocedural model of the atrium is created by moving a mapping catheter along the atrial wall. Then, the physician selects the same landmarks in the CT/MRI scan and the created model. The scan and the 3D model are then fused. See Sommer. CARTOUnivu allows using static fluoroscopic images to improve the details of the created 3D model. In the ENSITE system, intraprocedural atrial geometry is generated using a circular mapping catheter. Then similar to CARTOMerge, a rigid fusion is performed based on three fiducial corresponding points in CT/MRI and the 3D model. Locally also some deformable registration is performed to improve the alignment (see Sommer).

Figure 13:
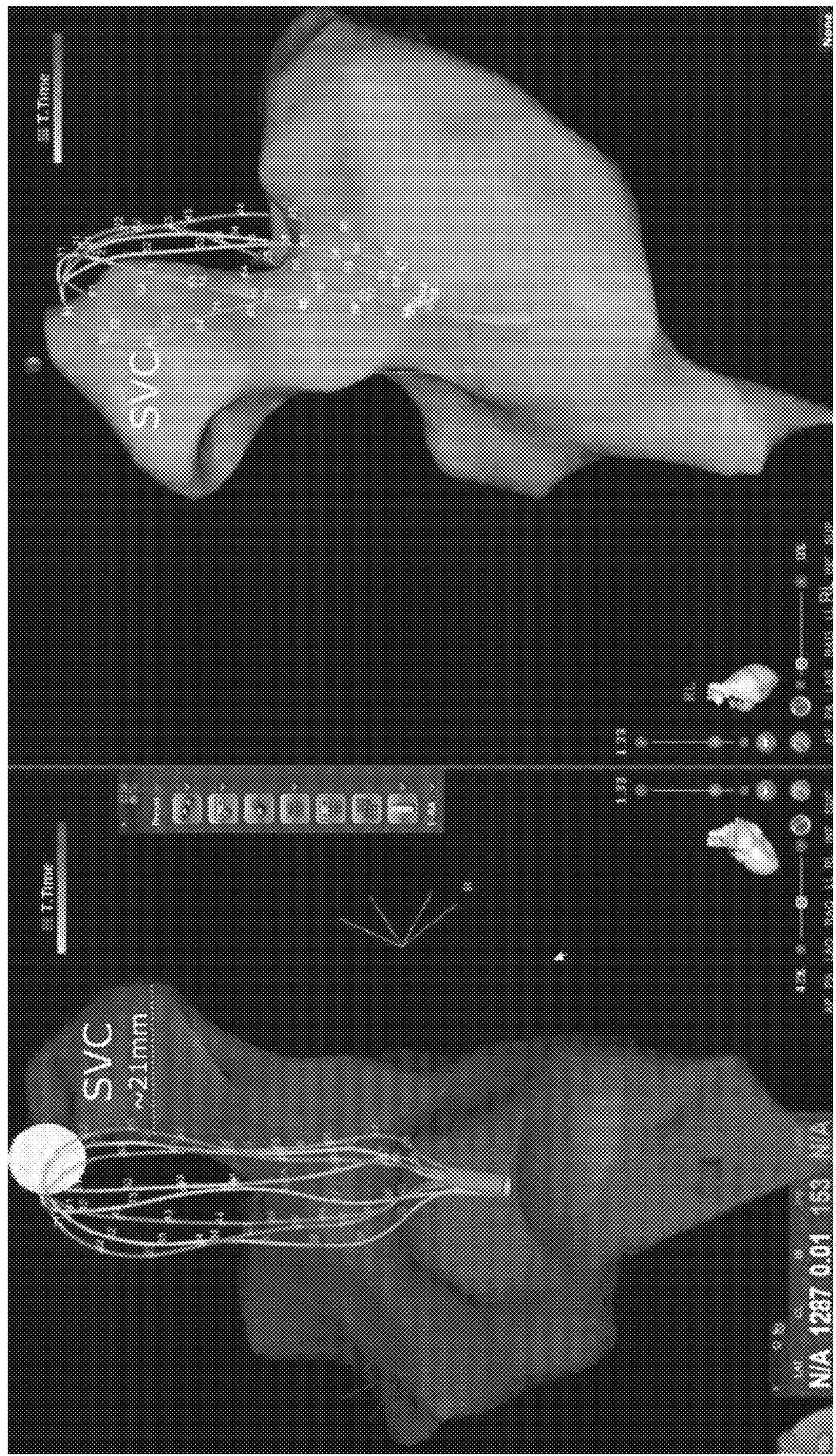
FIG. 13 shows examples of screenshots from a CARTO® system.

In Bourier et al. the accuracy of registration in a phantom model has been reported to be 1.62±0.77 mm in CARTO3 and 2.02±1.2 mm in ENSTE. These values only evaluate the registration of intraprocedural anatomy with MRI/CT, and not the fit of the 3D reconstructions to the anatomy. No study was found evaluating the performance of such a fit, and therefore an example image is provided in FIG. 13. In FIG. 13, an exemplary screenshot visualizing the fit of 3D reconstructions to intraprocedural anatomy is shown. The screenshots shown in FIG. 13 were taken from a CARTO3 system. Visualized in FIG. 13 are the intraprocedural anatomy and a 3D reconstruction of a BC. Most electrodes are mapped outside of the anatomy. The Superior Vena Cava (SVC) is estimated to have a diameter of around 21 mm. See, e.g., Sonovane et al.

Statistical Shape Modelling (SSM)

The advantages of a BC are twofold: first it can nestle against the atrial wall and therefore provide large coverage, and second it has a close enough spacing between electrodes so that the propagation of an atrial signal can be estimated. See, e.g., Oesterlein et al. The biggest challenge when using a BC is ability to deform significantly. Since a BC is very flexible, it can be deformed strongly, making the deformation relevant for estimating propagation of atrial signal.

Figure 14:
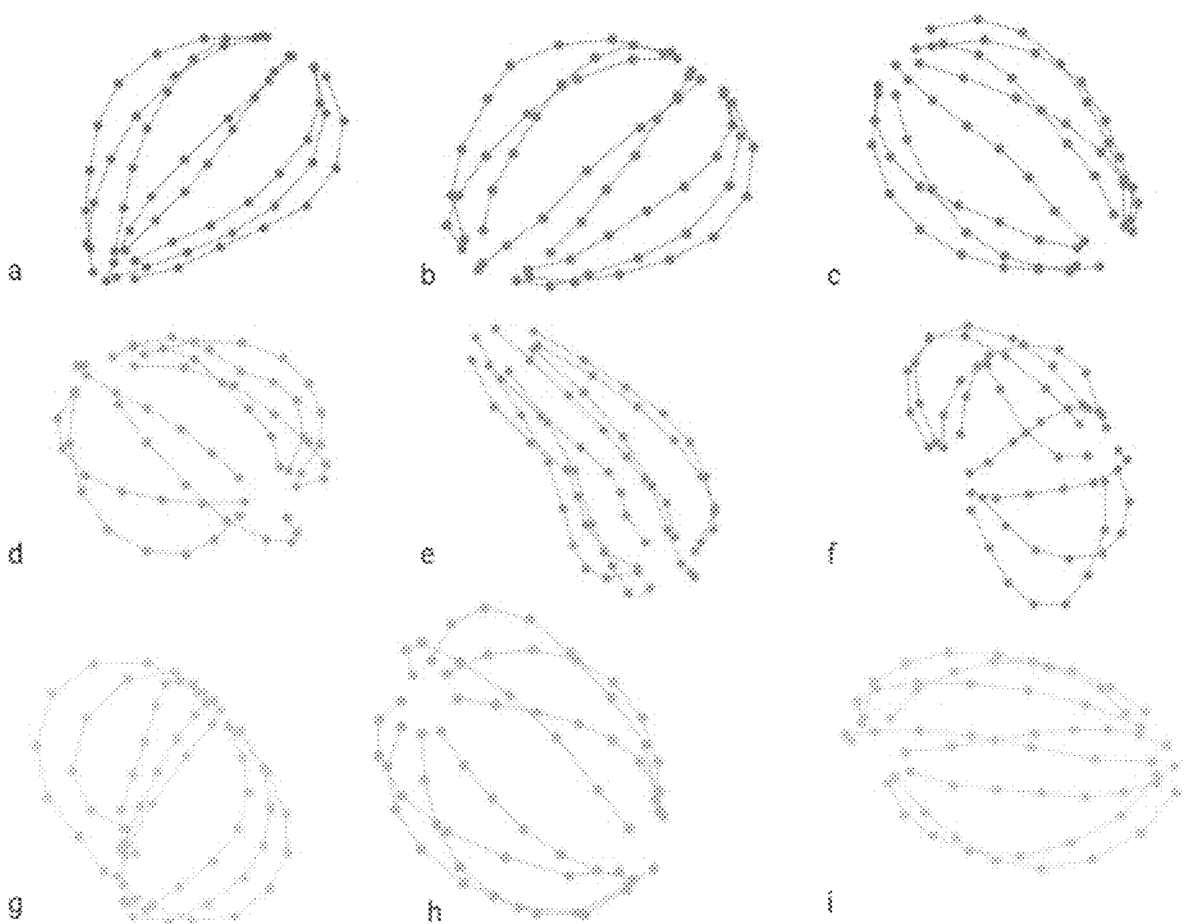
FIG. 14 shows 3D reconstructions of a basket catheter using a CARTO system.

Here, an SSM is computed to provide a space of possible deformation of a BC. At any location of any spline, pressure can lead to a deformation, therefore, every spline can be deformed independently. The two factors that are completely stable are the geodesic length of a spline and the geodesic distance of all electrodes along a spline. Furthermore, electrode distances between splines are more stable for electrodes at the poles. Estimated deformations of a BC from a CARTO3 navigation system are displayed in FIG. 14, CARTO was able to estimate a large variety of deformations of BCs, including those that are not physically plausible. This can be especially seen for electrodes at or near the poles of a BC. FIG. 14 shows 3D BC reconstructions obtained using a CARTO system. BC electrodes located near the poles show unrealistic positioning (see, e.g., illustrations g, h and I in FIG. 14).

Preprocessing

Figure 15:
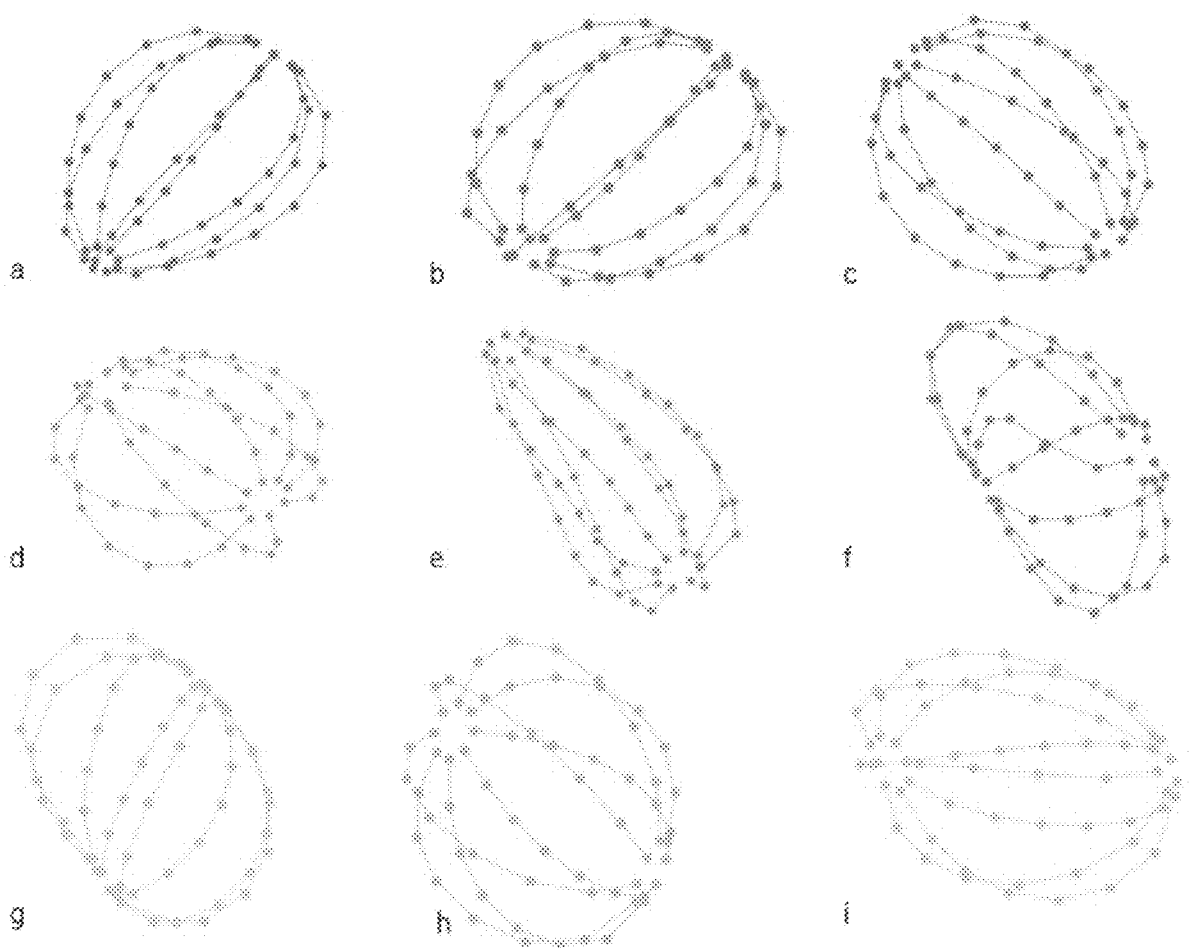
FIG. 15 shows preprocessed CARTO reconstructions from FIG. 14.
Figure 16:
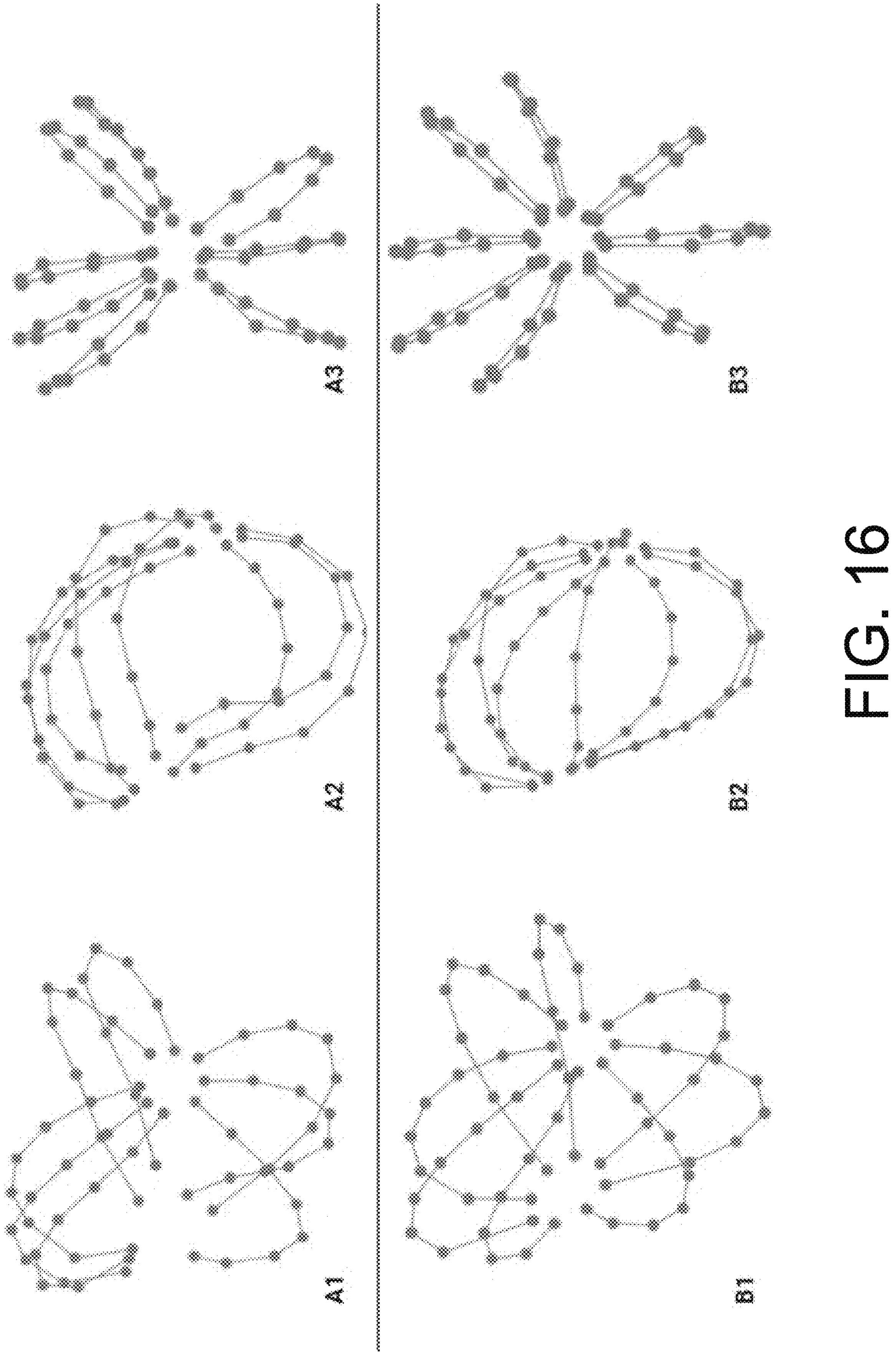
FIG. 16 shows basket catheter deformations from different angles.

The dataset employed contained 160 BC deformations estimated by CARTO. To ensure all shapes were physically realistic, the data were preprocessed using radial basis function (RBF) smoothing. Furthermore, the geodesic distance along a spline was used to correctly position electrodes. After preprocessing, all data samples showed realistic deformations at the poles and along the spline, but preserved a large variety of deformations (see FIGS. 15 and 16). FIG. 15 shows preprocessed CARTO3D reconstructions obtained using data from FIG. 14. FIG. 16 shows one BC deformation displayed from different angles. A1-A3 shows the 3D reconstruction from CARTO and B1-B3 show the same BC position after preprocessing.

Principle Component Analysis (PCA)

To develop an SSM, we used principle component analysis (PCA), which assumes a multi-variate Gaussian distribution of the data samples. Before applying PCA, all data samples must be aligned to a common coordinate frame. The undeformed basket model is chosen as the base model and all data samples are aligned to this model using the Kabsch algorithm. From the covariance matrix calculated by PCA, n eigenvectors $\phi_i$ and the corresponding eigenvalues $\lambda_i$ are calculated. PCA also computes the mean value of the data $\bar{x}$. Any data sample x from the training set can be approximated using the formula:

$$x \approx \bar{x} + \Phi \cdot d \quad (1)$$

with $\phi=(\phi_1, \phi_2, \ldots \phi_n)$ and where d is a n dimensional vector given by $$d = \Phi^T(x - \bar{x}) \quad (2)$$

The values of vector d are parameter values for the deformation of the BC, and by varying these values, new realistic deformations can be generated. To force the deformation variables to be in a similar range as in the training data, a limit can be applied. For each id component of d, the variance is given by $\lambda_i$. To force a deformation similar to the training data, $d_i$ can be constrained to lie in the range $[-3\sqrt{\lambda_i} + 3\sqrt{\lambda_i}]$.

3D Reconstruction

The goal is to reconstruct BC geometries throughout the atrium. All BC positions from the same procedure should be arranged in a meaningful space with correct spacing between electrodes. Such a system would be able to: (1) reconstruct the correct deformation of each basket, and (2) reconstruct the relationships between different BC positions. Denner has shown that far-field QRS complexes can be fed into a constraint autoencoder, and that a mapping between QRS morphology and 3D space can be learned. This architecture is extended here to allow only realistic deformations of splines, and also to increase the number of different deformations that a network can learn.

Preprocessing

First, a far-field QRS has to be extracted from the raw signals. For this a pipeline from Tenbrink was used. First the ventricular signal has to be estimated. For this a modelling of the signal is used which divides the signal into its atrial components, ventricular components, low-frequency high-amplitude components, and narrow frequency band components originating from nearby electronic devices. After extraction of the far-field signal from the intracardiac recordings, the start of the QRS signal has to be detected. To extract the start of a QRS signal, an ECG signal is used because QRS signals can be detected robustly from the body surface. Then, a clustering algorithm as described by Ester et al. is applied that filters out the QRS complexes which do not belong to the biggest cluster.

Autoencoder Model

Figure 17:
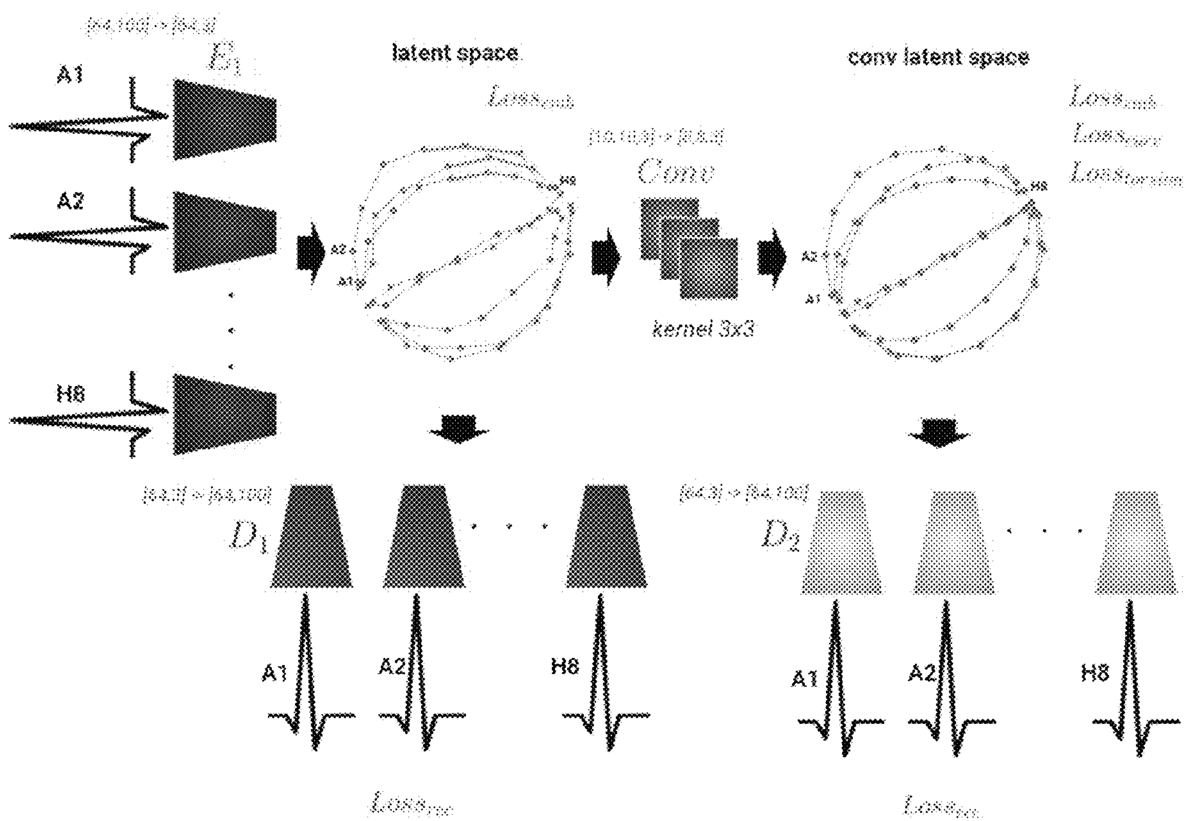
FIG. 17 shows one embodiment of a network architecture.

One embodiment of a complete network architecture is shown in FIG. 17. Such an architecture includes encoder E1 and decoder D1 as proposed by Denner. E1 is a fully connected Siamese network comprising 64 sub-networks, which all share the same weights. A sub-network $net_i$ receives an input $x_i$, which is the mean QRS recorded at electrode $e_i$. The decoder D1 is also a Siamese network that reconstructs the QRS signal from the latent space. A reconstruction loss enforces that the input and reconstructed input must be similar. The latent space is constrained to three numbers that represent the x, y, z coordinates of the electrodes. In the latent space, the shape of the BC is constrained by fitting a basket geometry; this loss is called the embedding loss $L_{emb}$, and is discussed in more detail below. Such a network has a very limited number of trainable parameters, and requires learning a function from each QRS to xyz. As a result, the network generalizes well even with a small amount of training data. Intuitively, we expect the encoder to learn a non-linear mapping so that similarities of QRS reflect similarities in 3D coordinates. The motivation for this is that the closer the electrodes are to the ventricle, the more the morphology of the QRS changes. Therefore, when learning such mapping, the network preferably accounts for these non-linear similarity changes in QRS space.

In Denner's setup, the network architecture was not able to adjust the position of one electrode based on signals from the neighboring electrodes because the sub-network of E1 received only a single QRS signal as input. Here we take into account the signal and the predicted positions of the neighboring electrodes. This allows for more robust predictions as well as the ability to indirectly model the stiffness of splines to create realistic 3D reconstructions of the BC. To achieve this, a convolutional filter Conv can be introduced that slides over 3×3 neighbors and over the BC reconstruction in latent space (in FIG. 17, see the location marked in green on the BC in the latent space).

After the Conv layer, torsion and curvature losses can be applied, constraining the relations of the electrodes along a spline. This creates a second latent space (conv latent space), which can be thought of as a smoothed version of the first latent space. In the conv latent space, the embedding loss is applied again after feeding the 3D positions through the decoder $D_2$.

In one embodiment, all these networks ($E_1$, $D_1$, $D_2$, Conv) are trained end-to-end and all losses are combined in a weighted sum and minimized. $E_1$ is a three-layered fully connected NN with 50, 25 and 3 neurons per layer. $D_1$ and $D_2$ have 25, 50 and 100 neurons per layer. Overall, and in one embodiment, the whole network architecture has less than 20,000 trainable parameters.

Continuing to refer to the embodiment of the network architecture of FIG. 17, Encoder ($E_1$) is a Siamese network with 64 sub-networks that all share the same weights (red). As input $E_1$ receives the mean QRS signals recorded at the 64 electrodes of a BC (A1, A2, . . . H8), and maps it into a 3D space. The sub-network learns a function from a single QRS signal to a single point in space represented by xyz-coordinates. From here, there are two paths: one path feeds the embeddings into decoder 1 ($D_1$) and reconstructs the QRS signals. The second path consists of smoothing the shape of the baskets using a convolution kernel (Conv) by including neighborhood information and producing a smoothed embedding in the Conv latent space. Then, the signal is reconstructed using decoder 2 ($D_2$). The reconstruction losses ($L_{rec}$) are applied after the decoders and the embedding losses ($L_{emb}$) which fit a basket geometry are applied in the latent spaces. In the Conv latent space we have additional losses ($L_{curv}$ and $L_{torsion}$) that constrain the shape of the splines. In one embodiment, all these networks are trained end-to-end and the final loss function combines all losses into a weighted sum (see equation 3 below). As shown in FIG. 18, and according to one embodiment, inputs to convolution layers are provided where an 8×8 grid (bright green) is padded to a 10×10 grid with respective adjacent electrode positions.

Losses

The overall loss $L_{full}$ can be represented by the weighted sum over 4 different losses:

$$L_{full}=\alpha\cdot L_{REC}+\beta\cdot L_{EMB}+\gamma\cdot L_{torsion}+\delta\cdot L_{curv} \tag{3}$$

with α, β, γ and δ being the hyperparameters.

Reconstruction Loss

Overall reconstruction loss is the absolute difference between the inputs X and the output from $D_1$ and $D_2$. It measures how well the QRS signal was able to be reconstructed through the different paths:

$$L_{REC}=\Sigma|X-D_1(R_1(X))|+|X-D_2(\text{Conv}(E_1(X)))| \tag{4}$$

Curvature and Torsion Loss

The stiffness of the splines can be modelled indirectly by minimizing curvature and torsion of the splines. The BC can be represented by multiple discrete space curves. Since the electrodes are fixed along a spline and two opposite splines form a ring, the BC can be represented as 4 rings of discrete curves. The vertices of a curve i can be denoted as $\vec{v}_{i,j}$ and the edges as $\vec{e}_{i,j}$, which are the difference vector between two consecutive vertices $\vec{v}_{i,j}$ and $\vec{v}_{i,j+1}$.

The curvature $k_i$ for each ring i can be calculated as the sum of all magnitudes of the second derivative of the curve. For the second derivative the change of unit tangent vectors is calculated. The tangent vector for ring i and electrode number j is the edges $\vec{e}_{i,j}$. $L_{curv}$ is the average sum of $k_i$ for n rings:

$$L_{curv}=\frac{1}{n}\sum_{i}^{n}\sum_{j}^{8}\left\|\frac{\vec{e}_{i,j-1}-\vec{e}_{i,j}}{\left\|\vec{e}_{i,j-1}-\vec{e}_{i,j}\right\|}-\frac{\vec{e}_{i,j}-\vec{e}_{i,j+1}}{\left\|\vec{e}_{i,j}-\vec{e}_{i,j+1}\right\|}\right\| \tag{5}$$

Torsion loss calculates the out-of-plane rotation of a curve and is defined for an edge $\vec{e}_{i,j}$. Two consecutive edges always form a plane with the two edge vectors as basis. For three consecutive edges, the first two edges define a plane and the last two edges define another plane. The torsion at edge $\vec{e}_{i,j}$ is the angle between the normals of the two planes. The unit normal $\vec{n}_{i,j}$ is calculated as the cross product of two consecutive edges $\vec{e}_{i,j}$ and $\vec{e}_{i,j-1}$, and then normalized. The calculation of $L_{torsion}$ minimizes the total torsion of the BC:

$$n_{i,j}=\frac{\vec{e}_{i,j}\times\vec{e}_{i,j-1}}{\left\|\vec{e}_{i,j}\times\vec{e}_{i,j-1}\right\|} \tag{6}$$

$$L_{torsion}=\frac{1}{n}\sum_{i}^{n}\sum_{j}^{8}\arccos\left(\vec{n}_{i,j}\cdot\vec{n}_{i,j+1}\right) \tag{7}$$

Minimizing curvature and torsion constrains both the bending of a spline and the out-of-plane rotation along a spline.

Embedding Losses

The embedding loss $L_{emb}$ forces the latent space to reassemble the xyz coordinates of the electrode locations in a Euclidean space. The loss constrains the 3D points in the latent space to be arranged like a sphere. In particular, when there are multiple BC locations, the network must ensure that all BC locations form a sphere and the QRS signals can still be reconstructed from that location. The embedding loss is calculated separately for each latent space, and the sum of the losses gives the total loss $L_{EMB}$:

$$L_{EMB}=L_{emb}(E_1(X))+L_{emb}(\text{Conv}(E_1(X))) \tag{8}$$

In the following, two different embedding losses are explained. The sphere embedding loss $L_{emb\text{-}sphere}$ proposed by Denner, and $L_{emb\text{-}shapemodel}$ that is used in the SSM.

In Denner, the pairwise distance matrix $D_{sphere}\in R^{64\times64}$ of an undeformed BC (unit sphere) is used to enforce a similar pairwise distance of 3D points in the latent space. Besides the distance matrix of a sphere a second prior is given in form of a weighting matrix $M\in R^{64\times64}$, with a weight for every pair of electrodes. The idea of the weighting matrix is to constrain some deviations from the unit sphere more than others, e.g., the pairwise distances between electrodes along a spline are relatively fixed, while distances of electrodes from different splines can deviate strongly.

$$L_{emb\text{-}sphere}(D_{sphere},D_{\hat{p}})=M\odot\|D_{sphere}-D_{\hat{p}}\| \tag{9}$$

With $D\in R^{64\lambda64}$ representing the pairwise distance matrix of the 3D points of one BC position in the latent space.

The newly proposed embedding loss uses an SSM of the BC (see Datasets section below). The shape model provides the eigenvectors ϕ, the eigenvalues λ, and the mean shape $\bar{x}$. In each training step, a realistic shape s from the shape model is computed that is the most similar to the current 3D reconstructions p in the latent space. Then we can compute the squared error between the realistic shape and the 3D reconstructions:

$$L_{emb\text{-}shapemodel}(s,p)=\|s-p\|^2 \tag{10}$$

To compute s, the current predictions p must be rotated and translated to line up with the standard rotation of the training data for the SSM. Rotation R and translation t are calculated via Kabsch algorithm. Then, p can be projected into the space of deformation parameters of the SSM:

$$d=\Phi\cdot((R\cdot p+t)-\bar{x}) \tag{11}$$

For a deformation value $d_i$ in d that is not in the range $[-3\sqrt{\lambda_i}, +3\sqrt{\lambda_i}]$ of realistic deformation parameters, value $d_i$ is replaced by the deformation value for the mean shape $d_{\bar{x}_i}$. This can be viewed as a projection back on the manifold of realistic deformations. From the final deformation parameters, the shape of the basket is calculated, and inverse Rotation $R^T$ and inverse translation −t are applied to obtain s.

Alignment to Anatomy

Previously, a method for estimating the relative position of BCs in the atria was presented; such a learned reconstructed space of BCs (RSB) contains information about deformation and displacement of the different BC positions. However, there is no information about the global position, i.e., the orientation of the RSB or its connection to anatomical features. The focus of this section is to learn global positioning of the RSB with respect to an anatomy.

Global position can be determined by mapping a precomputed RSB into the patient's anatomy. When a BC is inserted into an atrium, deformation of the BC is caused by collision with the atrial wall. Therefore, the shape of the BC must match the anatomy and the reconstructed shapes of the BCs include information about the form of the anatomy. With only one BC position, there are many possible solutions to fit the BC into the anatomy. However, using multiple BC positions and biological priors can highly reduce the solution space.

Biological priors can limit the possible solution space by adding additional constraints on the rotation of the RSB. Here, we use information such as the direction from which the BCs are inserted, e.g., the septum (for LA), and the direction from which the strongest amplitude signal arises, e.g., the mitral valve (for LA). These priors enforce a realistic solution for the registration of the anatomy and the RSB.

Segmentations

Segmentations of the heart chambers are extracted from CT scans using the software from Slicer 3D. The software is based on a region-growing approach using intensity statistics (see Xu et al.). The segmentations are convened to triangular meshes. For all patients with available CT scans, the 3D reconstructions of the BC positions are calculated using the constrained autoencoder model.

Registration

The mapping between the RSB and the anatomy mesh can be formalized as a rigid registration problem. We search for the translation vector t and the rotation matrix R which when applied to the RSB provides the best fit to the anatomy mesh. The parameters are learned iteratively via gradient descent. To find a plausible local minima, biological priors are used for initialization.

Initialization

Initialization requires location of certain anatomical landmarks, such as the septum, located at the interface between the LA and RA, and the mitral valve, located between the LV and RA. Since the landmarks are located at the boundary between different parts of the heart, their position can be estimated automatically:

$$G_{M_1M_2} = \left\{ \vec{g} \mid \vec{g} \in M_1 \wedge \exists \vec{p} \in M_2 : \sqrt{\sum_{i=1}^{n} (g_i - p_i)} < t \right\} \quad (12)$$

$$O_{M_1M_2} = \frac{1}{|G_{M_1M_2}|} \sum_{i=1}^{|G_{M_1M_2}|} \vec{g}_i \quad (13)$$

$M_1$ and $M_2$ are adjacent structures in the heart and G is the set of all points in $M_1$ that have a Euclidean distance less than t to any of the points in $M_2$. The average of all points in G then determines the estimated location of the landmark. The location of the septum $o_{lara}$ with $M_1$=la and $M_2$=ra and the location of the mitral valve $o_{lalv}$ with $M_1$=la and $M_2$=lv.

Figures 19A, 19B:
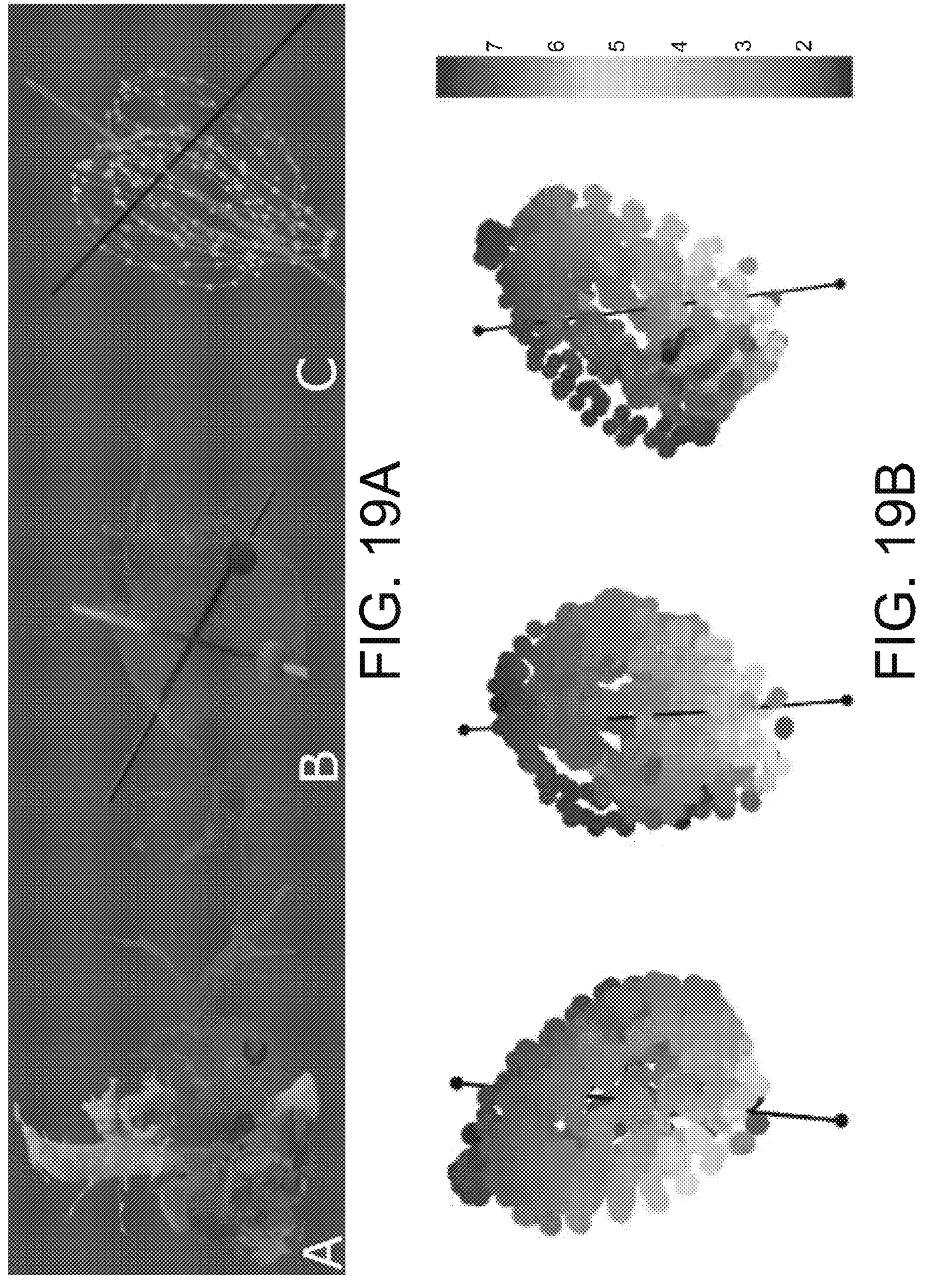
FIGS. 19A and 19B show segmentations of the heart and the reconstructed spaces of basket catheters (RSBs), respectively.

In FIG. 19A, Panel A shows segmentations of LA (blue), RA (red) and SVC (green) with estimated positions of the septum (pink) and mitral valve (dark blue). Panel B shows the left atrium with axes $\vec{a}_{sc}$ (pink) and $\vec{a}_{mc}$ (blue). Panel C shows the RSB with calculated axis $\vec{b}_{sc}$ (pink) and $\vec{b}_{mc}$ (blue).

Given the location of the landmarks, two axes can be defined in the anatomy mesh (see Figure Panel B in FIG. 19A). The axis $\vec{a}_{sc}$ points from the septum to the center of mass of the LA and the axis $\vec{a}_{mc}$ points from the mitral valve to the center of mass of the LA $c_{la}$.

$$\vec{a}_{sc} = c_{la} - o_{lara} \quad (14)$$

$$\vec{a}_{mc} = c_{la} - o_{lalv} \quad (15)$$

The corresponding counterparts $\vec{b}_{sc}$ and $\vec{b}_{mc}$ can be defined in the RSB (see Panel C in FIG. 19A). For only one BC, the axis $\vec{b}_{sc}$ is the vector pointing from the proximal tip $\vec{p}_{proximal}$ to the distal tip $\vec{p}_{distal}$ of the BC. If there are multiple BC positions, the average direction from the proximal to the distal tip is calculated over n BC positions:

$$\vec{b}_{sc} = \sum_{i=1}^{n} \left( \vec{p}_{i_{distal}} - \vec{p}_{i_{proximal}} \right) \quad (16)$$

The connection between $\vec{b}_{sc}$ and $\vec{a}_{sc}$ is that $\vec{a}_{sc}$ is the standard direction for BC insertion, where the BC is inserted with the distal tip first so that the proximal end is closer to the septum than the distal end.

To estimate the corresponding axis $\vec{b}_{mc}$ for $\vec{a}_{mc}$, the effect of distance from the mitral valve on signal intensity must be considered. The mitral valve is a gateway between the left atrium and the left ventricle, and therefore the signal can pass through with less resistance. Therefore, the closer the QRS is recorded to the mitral valve, the greater the amplitude of the QRS signal. The greatest change of amplitude across the RBS is calculated using multi-output regression (see FIG. 19B). Using x, y, z coordinates as the target variables Y and the maximum amplitude value as the dependent variable X, the linear model calculates the least squares solution of intercept $\vec{i}$ and direction vector $\vec{d}$. This direction vector $\vec{d}$ is used as axis $\vec{b}_{mc}$.

The corresponding vectors ($\vec{a}_{mc}$ and $\vec{b}_{mc}$, $\vec{d}_{sc}$ and $\vec{b}_{sc}$) in the anatomy and RSB are normalized and aligned using Kabsch's algorithm, which finds a rotation $R_{init}$ between the two sets of vectors. In FIG. 19B, the values of the maximum amplitudes are visualized in millivolts across an RSB. The RBS is displayed from three different angles. The axis of largest change is calculated using regression and displayed in black.

Optimization

For optimization, a loss function (equation 8) is defined which is minimized for the translation $\vec{t}$ and the Euler angles $e_x$, $e_y$, $e_z$ defining the rotation matrix R. The current estimated rotation R and $\vec{t}$ are applied to the electrode positions P in the RBS to obtain the registered positions $P_{reg}$. P and $P_{reg}$ are of the form [n, 3], where n represents the number of electrodes:

$$P_{reg}=P\cdot R+\vec{t} \quad (17)$$

$$\text{Loss}=\alpha\cdot\text{Loss}_{in\text{-}mesh}+\beta\cdot\text{Loss}_{mc\text{-}prior}+\gamma\cdot\text{Loss}_{sc\text{-}prior} \quad (18)$$

The loss function is composed of several parts. $\text{Loss}_{mc\text{-}prior}$ and $\text{Loss}_{sc\text{-}prior}$ maintain the alignment of the RSB axes with the anatomy axes used for initialization. This ensures that the solution is biologically plausible. The $\text{Loss}_{in\text{-}mesh}$, on the other hand, prevents electrode positions from being mapped outside the anatomy mesh. $\text{Loss}_{in\text{-}mesh}$ is calculated as the average difference vector between electrode positions outside the mesh and the closest point on the mesh surface.

$$Loss_{in-mesh} = \sum_{i=1}^{n}(p_{reg_i} - cp_i)m_i \quad (19)$$

with $cp_i$ being the closest point to $p_{reg_i}$ and also a surface point on the mesh. The boolean $m_i$ is true if the electrode position $p_{reg_i}$ is mapped outside of the mesh.

Simulation

Evaluating the accuracy of 3D reconstruction of cardiac catheters is challenging. Many experiments are performed in water tanks or are based on comparison to other systems. In Denner, the accuracy of the method is based on comparison to 3D reconstructions of CARTO. Given reconstruction of unrealistic BC deformations, this data cannot serve as ground truth. Furthermore, this data is limited since deformation and relations of BCs cannot be changed in a controlled way.

Consequently, simulations can serve as a valuable tool to evaluate accuracy and identify biases. As the system is learning on QRS signals, the activation pattern in the ventricles is simulated. This provides ground truths as well as a controlled way to test different scenarios.

Modeling of Ventricular Activation

The simulation requires the specification of the location of excitable cells v in the ventricle and the location of measurement electrodes e in the atria. On this basis, a lead field matrix G can be calculated, which indicates how activation at a particular cell affects the recorded signal at a particular electrode. G is of size $[n_e, 3\cdot n_v]$, where $n_e$ is the number of electrodes and it is the number of excitable cells. The factor of three results from modeling activation at the ventricle as rotation-free dipoles, so there are three entries for each cell representing the x,y,z direction. To define the location of the excitable cells, a CT segmentation of the heart is used, and each vertex of the ventricular meshes is used as a cell location.

As proposed by Kahlmann et al., the modeled signals A at the electrodes can be calculated via matrix multiplication of lead field matrix G and signal propagation matrix Q.

$$A=G\cdot Q \quad (20)$$

Figure 20:
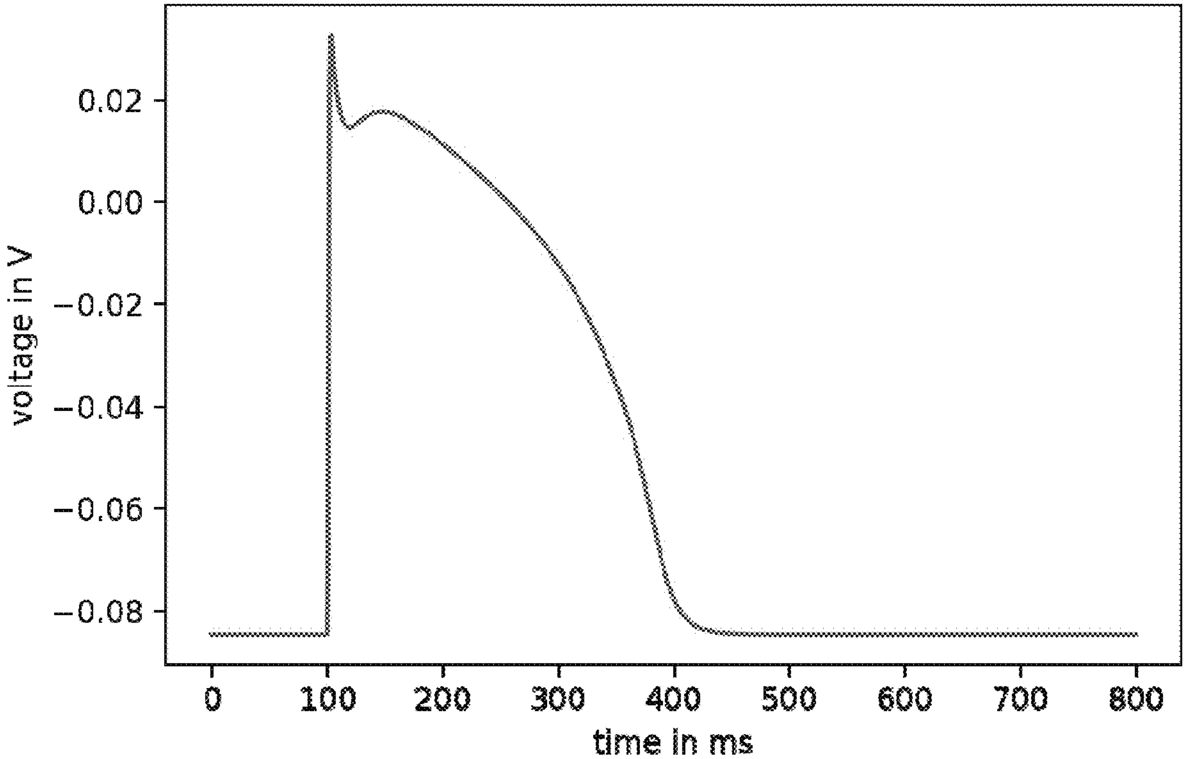
FIG. 20 shows an example of an action potential in a Purkinje cell.

A is of size $[n_e, t]$, where t is the duration of the signal. Q is of size $[3\cdot n_v, t]$ and encodes the activation of each cell at time t separately for x, y, and z directions. A single activation of a cell is modeled with a Beeler-Reute model for Purkinje cells and is shown in FIG. 20, where an example of an action potential of a Purkinje cell via the Beeler-Reuter model is shown (see Beeler et al.). Activation of the Purkinje cells in the ventricles is the main driver of the QRS signal. The derivative of the signal is the change in activity that can be measured in the atria. Here the propagation velocity for Purkinje cells is approximately by 2.5 msec. (see Ideker et al.) To define the matrix Q, the onset of activation must be shifted accordingly. There are two main phases of activation (see FIG. 21). Phase one models signal propagation from the AV node to the apex along a narrow path. To estimate the onset of the signal, the geodesic distance along the path is multiplied by the propagation velocity. In the second phase, the cells of the entire ventricle are excited, starting from the apex. Here, the Euclidean distances for each cell location to the apex location are used to model the signal displacement. The direction of the signal is estimated from the triangular mesh of the ventricles by taking the normal of a triangle and projecting it onto the vector pointing from the valve to the apex.

In FIG. 21, there are shown modelled propagation patterns in the ventricles (red: left ventricle, blue: right ventricle). Each vertex of the mesh is modeled as a cell. In Panel A three landmarks are predefined for each ventricle: valve (red), AV node (blue), apex (green). In Panel B, the signal first travels from the AV node to the apex. The activation times (early (red) to late (yellow)) of the cells differ due to the geodesic distance of the activation pathway. In Panel C, the second step of signal propagation is the activation of all cells of the ventricle. This starts at the apex and then travels toward the atria. Here, we use a simplified model in which the activation time of each cell is based on the Euclidean distance from the apex.

Performance Measurement

To evaluate the performance of the space of learned BC positions, four accuracy metrics are used that compare the ground truth with the predicted data. These metrics provide in-formation about how accurate the space, the position and the deformation of the BC is learned.

The overall accuracy is captured by the average electrode distance $M_{avg}$ and the center of mass difference $M_{center}$. See Denner. To calculate these metrics, first a rotation R and a translation t that best match the predicted space of the baskets $P_i$ with the ground truth space of the baskets $GT_i$ are calculated using the Kabsch algorithm. Then, the average distance of all electrodes and the average distance of the center of mass for each BC position are calculated. The center of the BC positions are calculated as the average 3D point of all electrode position of one BC, where $pc_i$ denotes the center of a predicted BC position and $gtc_i$ is the center of a ground truth BC position:

$$M_{avg} = \frac{1}{n}\sum_{i}^{n}\|(R\cdot P_i + t) - GT_i\| \quad (21)$$

$$M_{center} = \frac{1}{n}\sum_{i}^{n}\|(R\cdot pc_{i_i} + t) - gtc_i\| \quad (22)$$

To assess the quality of the estimated deformation of a BC, the deformation score $M_{deform}$ is defined [5]. Each BC predictions $P_i$ is registered separately with the ground truth $GT_i$. Therefore, for every BC position i, a rotation $R_i$ and a translation $t_i$ is determined. The registered predictions are then compared to the ground truth data by calculation the average electrode difference across BC positions, $$M_{deform} = \frac{1}{n}\sum_{i}^{n}\|(R_i\cdot P_i + t_i) - GT_i\| \quad (23)$$

The local score $M_{local}$ is used to estimate how well the space of n BC positions is estimated in a local neighborhood defined by a threshold t. The difference between the pairwise electrode distance $D_{GT} \in [n \cdot 64, n \cdot 64]$ of the ground truth space of the basket and the pairwise electrode distance $D_{\hat{p}} \in [n \cdot 64, n \cdot 64]$ of the predicted space of baskets are calculated. A mask $M \in [n \cdot 64, n \cdot 64]$ is applied which is 1 for all pairwise distance $D_{GT} < t$ and 0 otherwise:

$$M_{local} = M - \|D_{GT} - D_{\hat{p}}\| \quad (23)$$

Datasets

A variety of data is used to evaluate both the qualitative and quantitative performance of our algorithms. Real-world data has been recorded from both humans and animals. They include additional CT scans, fluoroscopic images, and data from the CARTO3 navigation system. Furthermore, there are different types of simulated data. In total, there are 5 different datasets listed in Table 1, where R indicates real data and S indicates simulated data.

TABLE 1

| Different Names and Types of Datasets Employed | | |
|---|---|---|
| | type of data | additional data |
| R1 | patient data | CARTO ® 3 screenshots |
| R2 | animal data | fluoroscopic images |
| R3 | patient data | CT scans |
| S1 | simulated data on CARTO ® 3 reconstructions | |
| S2 | simulated data on smoothed CARTO ® 3 reconstructions | |

Real Data Recordings

All real-world data recordings are made using a 64-electrode BC (FIRMap™, Abbott, Abbott Park, IL) with a length of 50 mm or 60 mm. The BC is inserted into an atrium, and then an intracardiac EGM is recorded. For each position of the BC, at least 60 seconds of the signal are recorded, after which the BC is moved to another position or another recording is made in the same position. Additionally, a 12-lead ECG is recorded in parallel at all times.

Figure 22:
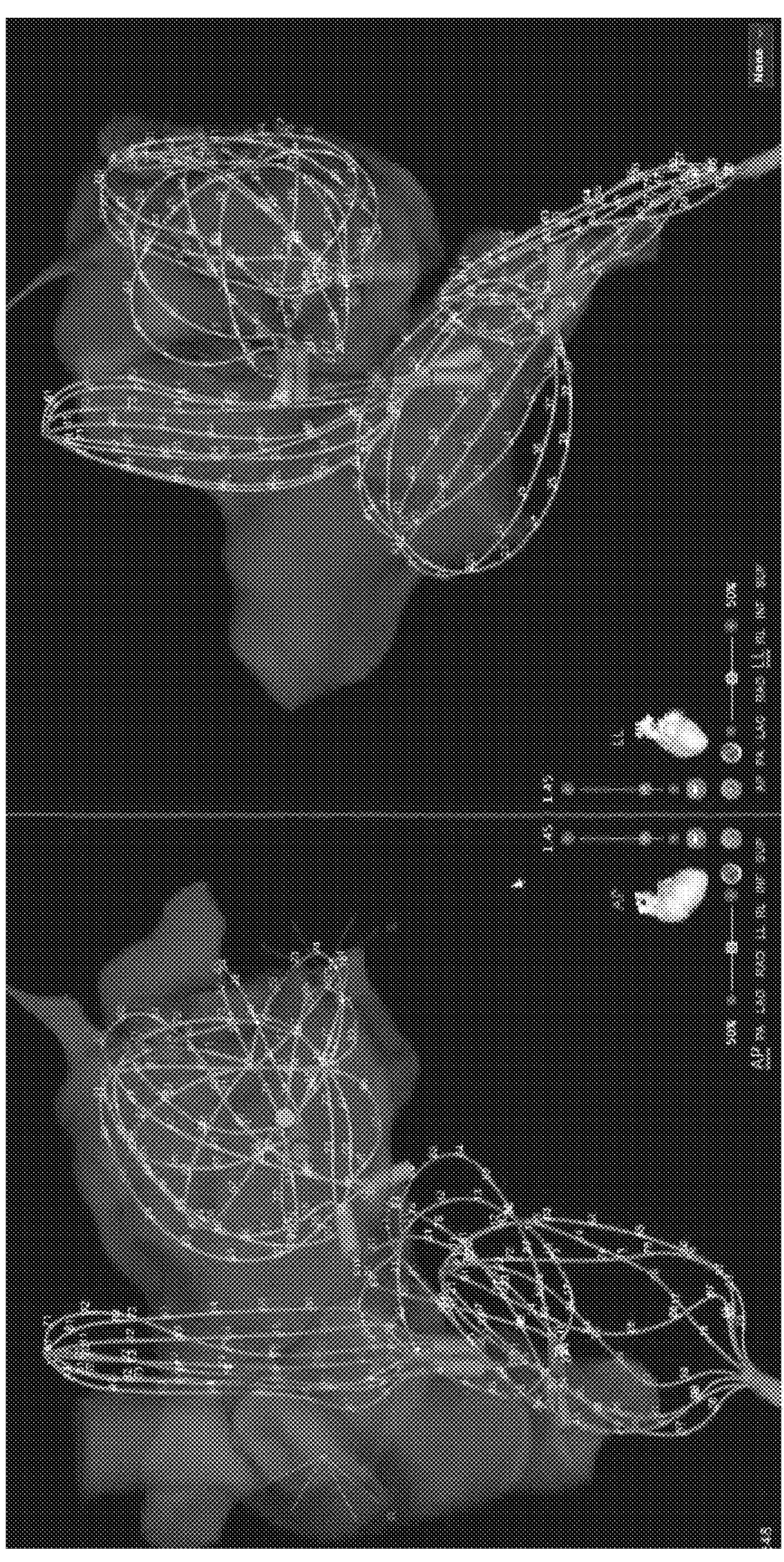
FIG. 22 shows two orthogonal screenshots from a CARTO system.

Dataset R1 (see Table 2) consists of 217 recordings from 19 patients recorded in the left atrium. For all these procedures the real-time navigation system CARTO3 was used and two orthogonal screenshots were taken. See FIG. 22, where two orthogonal screenshots from a CARTO®3 system show all BC positions for one procedure in the left and right atrium. These screenshots show all the BC positions for an entire procedure and allow the reconstruction of the shapes in 3D. Dataset R2 (see Table 3) was recorded on a dog and fluoroscopic images were made after each change in position of the BC. Dataset R3 (see Table 4) consists of 135 recordings from 18 patients. A CT of the chest was available for all of these patients. The CTs were acquired using single CT (SOMATOM Definition Edge, Siemens Healthcare, Erlangen, Germany) with a standard protocol of 100 kVp and 1.0 mm slice thickness.

TABLE 2

| R1: with CARTO ® screenshots | | |
|---|---|---|
| Patient name | Positions | Recordings |
| 02-002 | 6 | 19 |
| 02-003 | 4 | 12 |
| 02-004 | 4 | 13 |
| 02-005 | 2 | 6 |
| 02-006 | 3 | 9 |
| 02-007 | 3 | 9 |
| 02-008 | 4 | 12 |

TABLE 2-continued

| R1: with CARTO ® screenshots | | |
|---|---|---|
| Patient name | Positions | Recordings |
| 02-009 | 6 | 18 |
| 02-010 | 2 | 12 |
| 02-012 | 2 | 6 |
| 03-016 | 4 | 12 |
| 03-017 | 4 | 12 |
| 03-018 | 5 | 17 |
| 03-019 | 4 | 12 |
| 03-020 | 5 | 15 |
| 03-021 | 4 | 12 |
| 03-022 | 7 | 21 |

TABLE 3

| R2: with fluoroscopic images | | |
|---|---|---|
| Patient name | Positions | Recordings |
| dog4 | 7 | 7 |

TABLE 4

| R3: with CT scans | | |
|---|---|---|
| Patient name | Positions | Recordings |
| 02-001 | 3 | 9 |
| 02-004 | 4 | 13 |
| 02-009 | 6 | 18 |
| P-ROT-001 | 1 | 7 |
| P-ROT-003 | 2 | 6 |
| P-ROT-004 | 1 | 1 |
| P-ROT-006 | 2 | 4 |
| P-ROT-019 | 2 | 4 |
| P-ROT-020 | 1 | 2 |
| P-ROT-027 | 1 | 1 |
| P-ROT-028 | 2 | 4 |
| P-ROT-032 | 2 | 3 |
| P-ROT-034 | 1 | 2 |
| P-ROT-035 | 3 | 8 |
| P-ROT-039 | 6 | 22 |
| P-ROT-045 | 4 | 7 |
| P-ROT-046 | 3 | 10 |
| P-ROT-052 | 4 | 19 |

CARTO® Reconstructions

To reconstruct the 3D shapes of the CARTO® predictions from the screenshots (see FIG. 22), corresponding electrode positions are annotated in each image. Since the two orthogonal views are utilized, the camera motion is known and the position of each electrode can be computed in 3D space. Overall, 140 different basket shapes estimated with CARTO® are reconstructed. For the SSM, the data is spit into training (126 shapes) and test data (13 shapes).

Simulated Data

Figure 23:
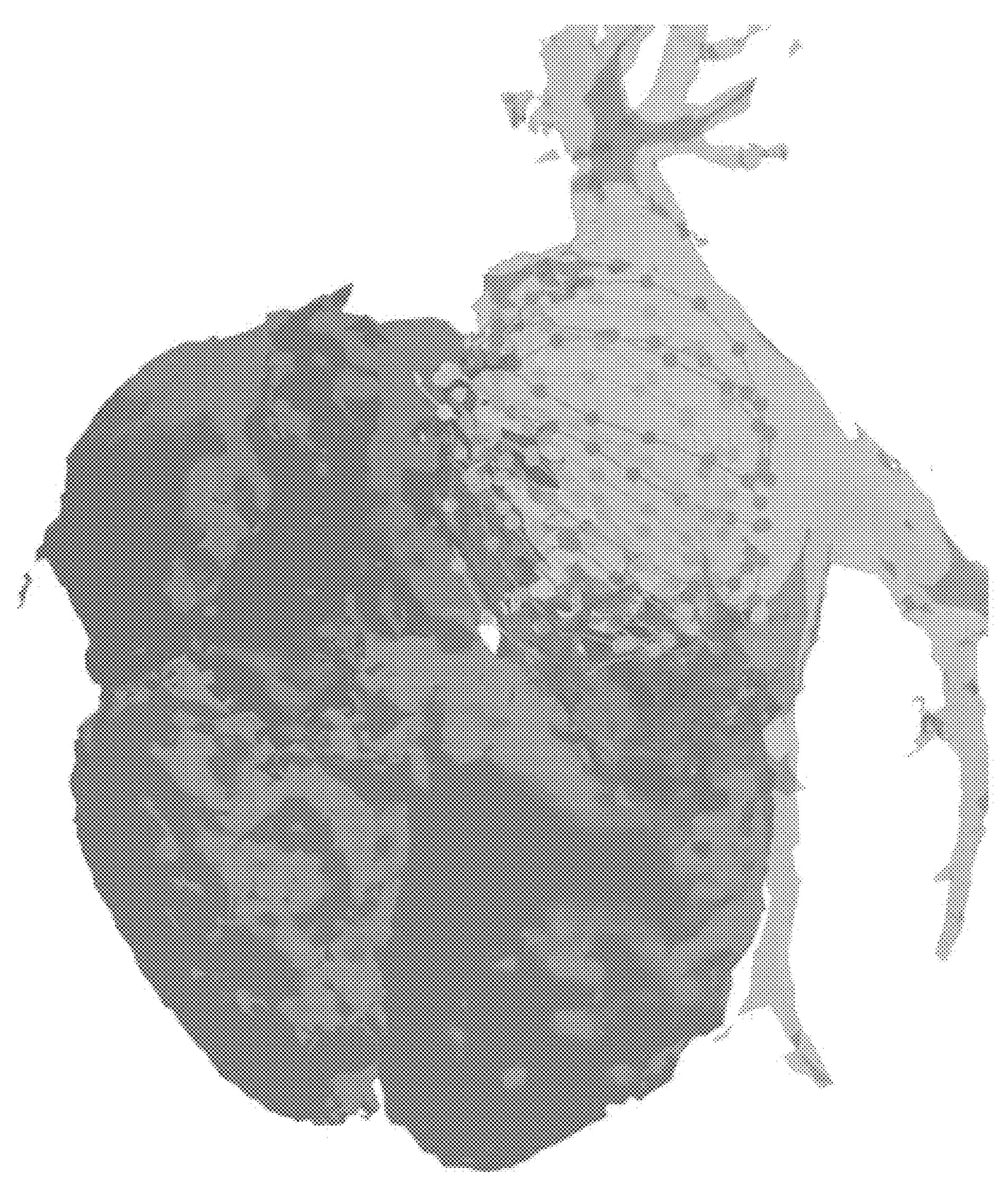
FIG. 23 shows a segmentation extracted from a CT scan of a human heart.

FIG. 23 shows segmentations extracted from a CT scan displaying RA (red), LA (blue), RV (purple), LV (green) portions. The CARTO® reconstructions are placed into the LA and electrode positions serve as sensor points for which the QRS signal is simulated. Here the CARTO reconstructions for patient 02-006 are displayed.

The theoretical background of the simulation process is described above. For the S2 dataset, CARTO reconstructions are placed into the atria. All BC positions of one patient are placed together. Therefore, the simulated data consists of signals for 18 procedures with 69 overall BC positions. For each BC position, 64 QRS complexes are simulated, one for each electrode. For the S1 dataset, we simulate the signal for preprocessed CARTO® reconstructions. Such preprocessing is described above. Dataset S1 data is split into validation and test data. See Table 5.

TABLE 5

Split of test and validation data

| | | | | | | | | | |
|---|---|---|---|---|---|---|---|---|---|
| val: | 02-002 | 02-003 | 02-005 | 02-006 | 02-007 | 02-008 | 03-019 | 03-021 | 03-022 |
| test: | 02-004 | 02-009 | 02-010 | 02-012 | 03-016 | 03-017 | 03-018 | 03-020 | |

Experiments and Results

Complexity of Simulated Data

Figure 24:
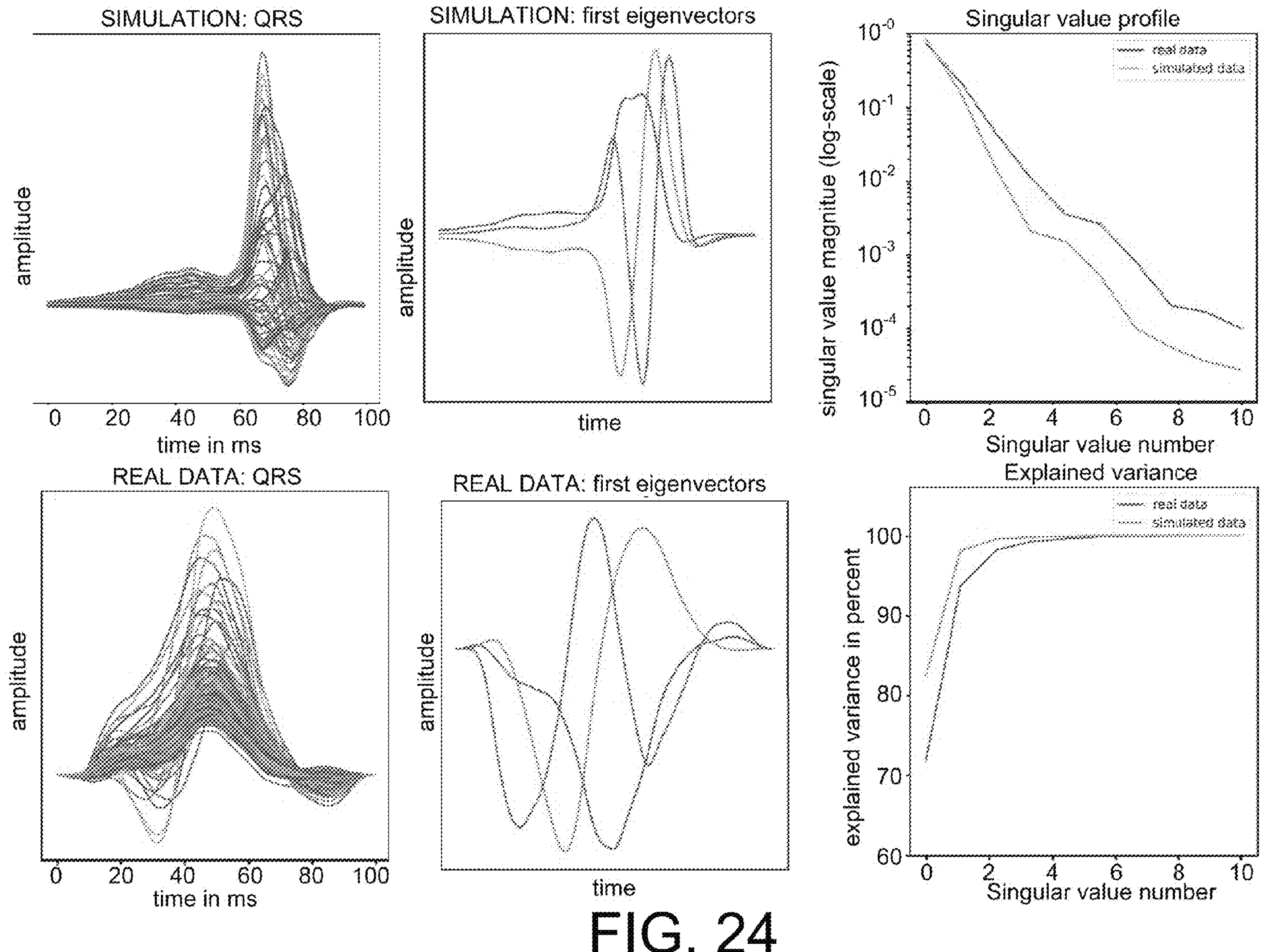
FIG. 24 shows simulated QRS complexes compared to real QRS complexes.

An important question is whether simulated data are complex enough to train and test one embodiment of the model. We assume this is the case if the simulated signals are of similar complexity to the real data. For simulation, the anatomy of patient 02-009 was chosen. The simulated and real QRS complexes of patient 02-009 are compared via singular value decomposition (SVD). FIG. 24 shows the morphology of the QRS complex of the simulated data and the real data, as well as the singular value profiles and the explained variance. Although the simulated data exhibit differences in morphology and duration compared with the real data, the complexity of the signal is comparable. The first three components can explain 98.1% (real data) and 99.5% (simulated data) of the variance. When the fourth component is taken into account, the explained variance increases to 99.3% (real data) and 99.8% (simulated data). In FIG. 24, data of simulated QRS complexes is compared with real QRS complexes measured in the atria. Compared are QRS morphology and complexity. The first column of FIG. 24 shows the QRS signal, the second column displays the first three eigenvectors of the signal, and the third column visualizes the singular values profiles and the explained variances. Our results show that simulated and real data have the same number of relevant components in an SVD and are therefore assumed suitable for training and testing in the models.

Effect of $L_{curvature}$, $L_{torsion}$ and Conv Layer

We introduced a Conv layer as well as two additional losses ($L_{curvature}$ and $L_{torsion}$) to constrain any unrealistic zig-zagging along splines. Our additional hypothesis was that the performance of our model could be increased by these changes, as the network can now access information about neighboring electrodes.

Figure 25:
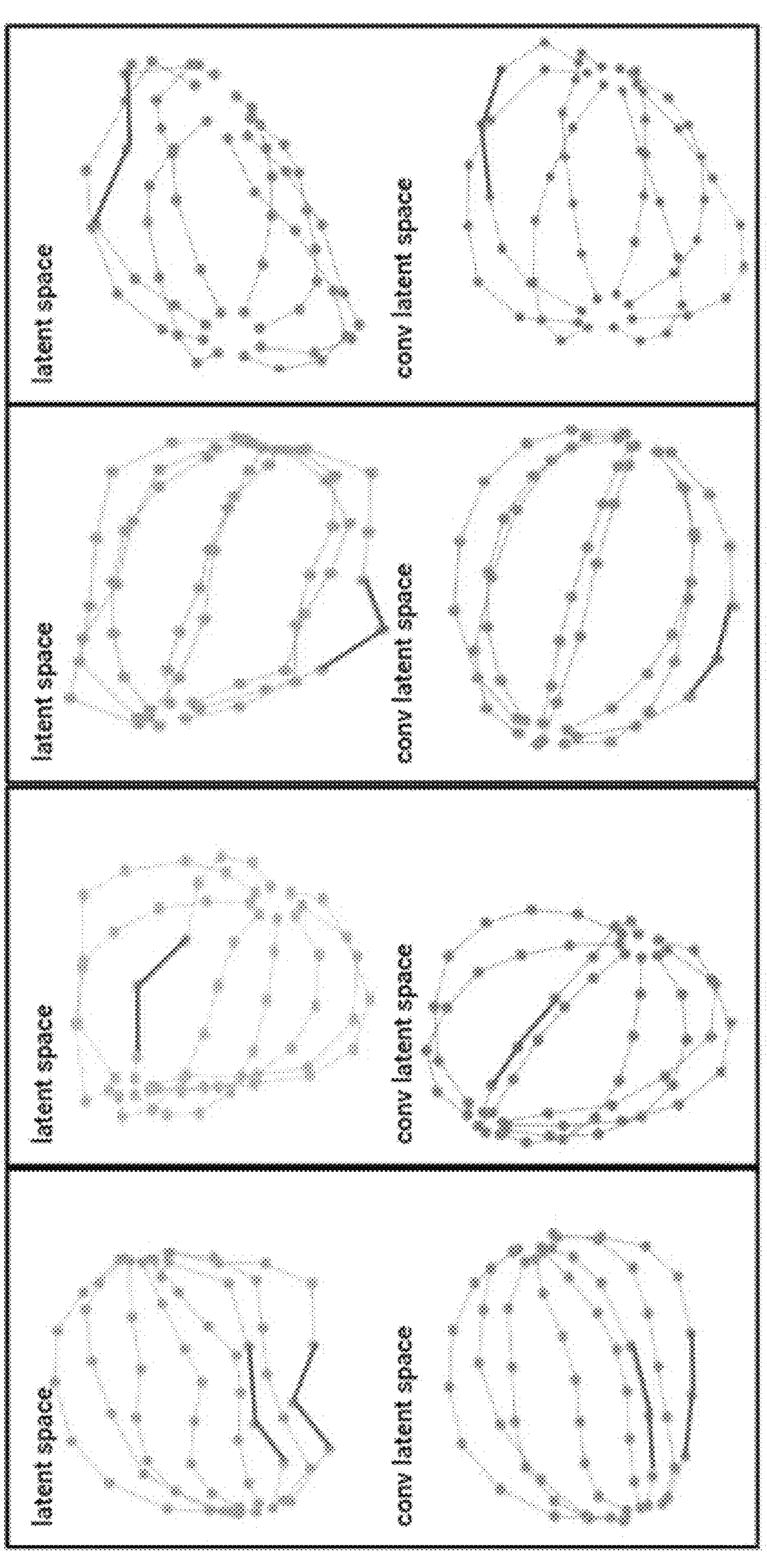
FIG. 25 illustrates differences between latent and Conv latent spaces.
Figure 26:
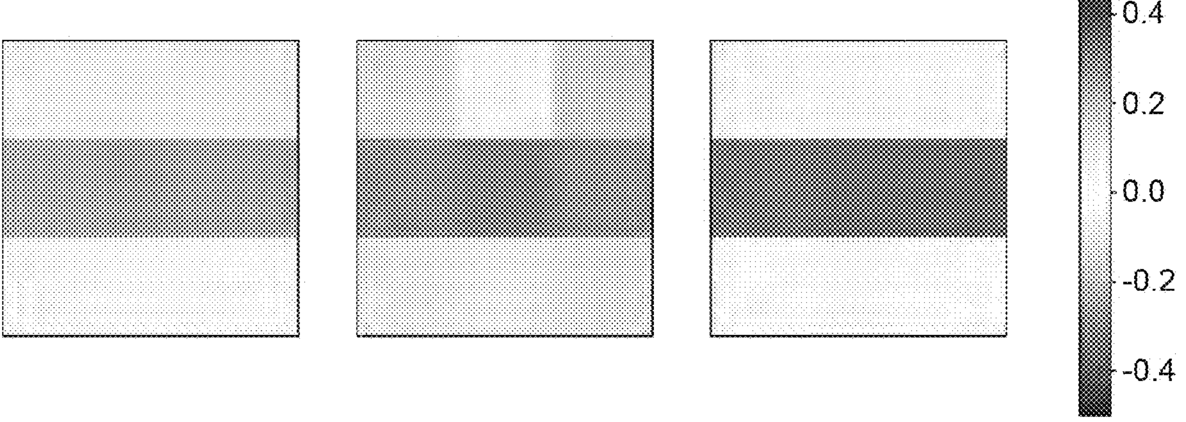
FIG. 26 shows a visualization of learned filters in a Conv layer of a network.

In the model described above, the predicted shapes of BCs can be visualized in latent space and the Conv latent space, which facilitates the interpretation of the effect of the Conv layer. FIG. 25 visualizes the differences between latent space and the Conv latent space. Specific regions of the splines are highlighted in violet to show the smoothing effect. In FIG. 25, such pairs of BCs are shown in latent space and Conv latent space. Highlighted in pink are some zig-zags along splines that were successfully smoothed out in the Conv latent space. FIG. 26 visualizes the learned filters, where the network learns a strong association of electrodes along splines (horizontal axis). The filters show high values along the horizontal axis, representing weights for neighboring electrodes along the same spline, and lower weights for neighboring electrodes of other splines. This corresponds well with the deformation profile of a BC. The performance is evaluated using the simulated data S1, and the 3D reconstructions are then compared to the ground truth. Three models are compared, the base model of Denner, the proposed model with Conv layer, and the proposed model with Conv layer with the additional losses. The performance is calculated for all available latent spaces. See Table 6 below.

TABLE 6

Deformation score in mm for different models compared across latent spaces

| | latent space | Conv latent space |
|---|---|---|
| Baseline [5] | 5.6 ± 2.63 | |
| Conv layer | 5.12 ± 2.11 | 4.76 ± 2.17 |
| Conv layer + $L_{curv}$ + $L_{torsion}$ | 4.67 ± 2.27 | 4.35 ± 2.08 |

The deformation score which compares ground truth shapes with the reconstructed shapes shows that performance is increased in the Conv latent space compared to the latent space. The model using Conv layer shows an improvement in score and standard deviation compared to the baseline (i.e., Denner). However, the best performance is achieved with the additional losses $L_{curv}$ and $L_{torsion}$ with a deformation value of 4.35±2.08 mm. Overall, the changes in the model contribute to more realistic, robust, and accurate BC reconstructions while maintaining the same level of interpretability.

Deformations

Figure 27:
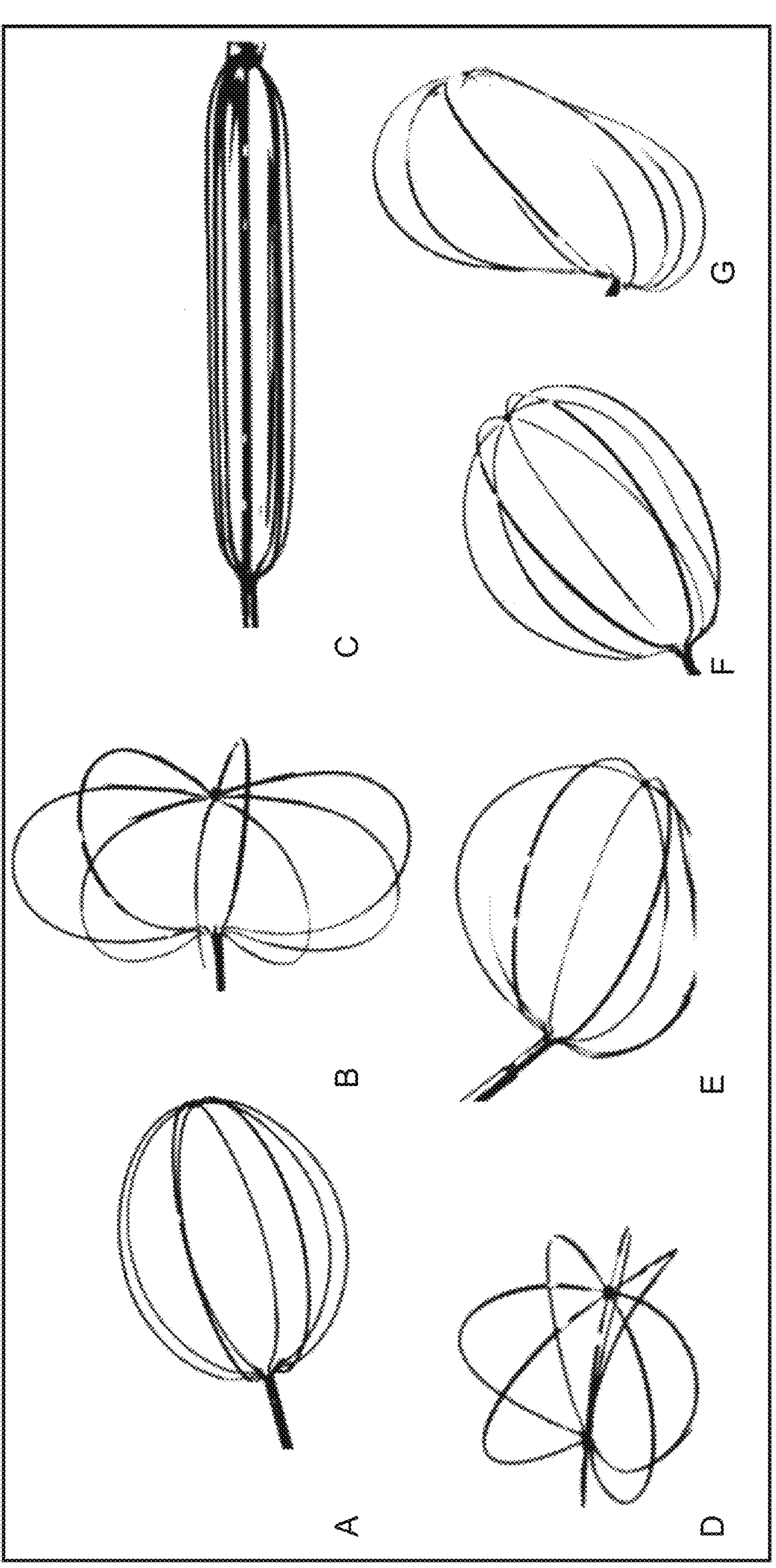
FIG. 27 shows photos of actual or real basket catheters in deformed shapes.

In this section, the effect of different embedding losses is compared. Embedding loss $L_{emb\text{-}shapemodel}$ uses an SSM described above. The extracted dimensions of the SSM are visualized in FIG. 28. and real photos of a BC with different deformations are shown in FIG. 27. The SSM disentangles meaningful dimensions of the deformation.

In FIG. 28, The first six dimensions of the SSM are shown along with the percentage of variance each dimension explains. Highlighted in black are the locations of each A1 electrode. The first component explains 47.5% of the variance in the data and represents the strain of the BC (as also seen in Panels B and C of FIG. 27). Components 2 and 3 of FIG. 28 appear to show forces acting on different sides of the BC (similar to Panel G in FIG. 27). The next three dimensions provide the basis for encoding spline-bunching (compare to Panel D of FIG. 27).

The first dimension explains almost 50% of the variance in the data and represents the distance between the distal and proximal poles. The next two dimensions, each explaining 10% of the variance, represent the pressure exerted from specific sides of the basket (from above or below, from the right or left side). Dimensions four to six efficiently encode spline bunching. Panel D of FIG. 27 shows the spline bunching of a real BC, where the angle between the two lowest splines is larger due to the bottom contact. Such deformation can be modeled with a combination of components four through six. Overall, the first six dimensions explain 84% of variance in the data and can reconstruct the data with an average electrode distance of less than 1 mm.

The $L_{emb\text{-}shapemodel}$ can be implemented with the SSM using various numbers of dimensions. Here it is implemented with six and one dimensions. For evaluation, a best model from above is selected and only the embedding loss is varied. $L_{emb\text{-}sphere}$ and $L_{emb\text{-}shapemodel}$ are compared based on the deformation and local score. The simulated data S1 are used for training and testing. See Table 7 below.

TABLE 7

Comparison of different embedding losses based on deformation score and local score in mm

| | deformation score | local score with threshold 50 |
|---|---|---|
| $L_{emb\text{-}sphere}$ | 4.35 ± 2.08 | 3.74 ± 0.99 |
| $L_{emb\text{-}shapemodel}$ with one component | 4.03 ± 1.72 | 2.83 ± 0.69 |
| $L_{emb\text{-}shapemodel}$ with six component | 4.04 + 1.64 | 2.82 ± 0.72 |

Both deformation and local scores are improved with $L_{emb\text{-}shapemodel}$ compared to $L_{emb\text{-}sphere}$. There is no significant difference between using one or six components; apparently the first dimension is most relevant for the model to adapt to. Overall, the best performance is obtained with a deformation value of 4.03±1.72 mm and a local value of 2.831±0.69 mm at threshold 50.

The improvement of performance can be explained when considering more stretched deformations (see the left panel in FIG. 29). With $L_{emb\text{-}shapemodel}$, the reconstructed shape is more similar to the ground truth than the one trained with $L_{emb\text{-}sphere}$. $L_{emb\text{-}sphere}$ is prone to learn more spherical shapes, while $L_{emb\text{-}shapemodel}$ can learn a wider range of deformations. The local score for multiple thresholds is shown in the right panel of FIG. 29, where $L_{emb\text{-}shapemodel}$ is shown to outperform $L_{emb\text{-}sphere}$ for all thresholds.

In FIG. 29, the left panel displays ground truth deformation (violet) from two views. The first panel on the left side of FIG. 29 shows the prediction with the $L_{emb\text{-}shapemodel}$ and the third panel on the right side of FIG. 29 visualizes predictions computed with $L_{emb\text{-}sphere,2}$. The local score with different thresholds (10 mm, 30 mm, 50 mm, 70 mm, and 100 mm) is calculated 2G for the different modes.

Overall, it can be said that the $L_{emb\text{-}shapemodel}$ is useful to capture a larger variety of deformations, and therefore the deformation score and local score are improved. Although the SSM manages to capture multiple meaningful dimensions for deformations, only the first one is relevant for $L_{emb\text{-}shapemodel}$.

Accuracy

Simulated vs. Real Data

In one embodiment, the accuracy of the model is estimated using different datasets: R1, S1 and S2. R1 contains real recordings and CARTO reconstructions. S1 is based on simulations of preprocessed CARTO reconstructions, and S2 is based on simulations based on original CARTO reconstructions.

For hyperparameter tuning, the validation set of S1 is used and the lowest score was achieved with $\alpha$=1.0, $\beta$=0.14, $\gamma$=0.06, and $\delta$=1.9. The Adams optimizer is initialized with a learning rate of 5e-3 and early stopping is used. Hyperparameters are only tuned on the S1 dataset because it contains ground truth shapes that show realistic deformations. For S2 the deformations can be unrealistic and for R1 no ground truth is available. The tuned model is then tested on S1, S2, R1 and compared based on the metrics defined in Section 4.5.

The results are displayed in Table 8 below. For S1, an average electrode distance of 4.4 mm and a deformation score of 4 mm is achieved. The center of mass is estimated with 1.2 mm error. For the real data R1, where the reconstructions get compared to CARTO reconstructions, the average electrode distance is 7.3 mm, the deformation score is 5.18 mm, and the center of mass is estimated with an error of 3.62 mm.

TABLE 8

Performance on real data and on simulated data in mm

| | avg electrode distance | deformation score | center of mass | local score with threshold 30 |
|---|---|---|---|---|
| S1 | 4.42 ± 1.82 | 4.03 ± 1.72 | 1.15 ± 0.31 | 1.4 ± 0.06 |
| S2 | 6.11 ± 2.71 | 5.15 ± 2.31 | 1.7 ± 0.85 | 2.0 ± 0.54 |
| R1 | 7.31 ± 2.85 | 5.18 ± 2.07 | 3.62 ± 1.67 | 3.34 ± 1.79 |

Reasons for the decreased performance of the real data could be noise as well as comparison to unrealistic shapes. To test the hypothesis if decreased scores can be linked to the unrealistic CARTO reconstructions, we look to the performance reflected in the S2 dataset. It can be seen that the model has increased deformation error (from 4 mm to 5.15 mm) due to the incapability of learning the original CARTO shapes. The deformation error is comparable for the R1 and S2 dataset with 5.15 mm and 5.18 mm. Therefore, it could be argued that some parts of the deterioration for R1 can be explained due to the unrealistic shapes, to which the reconstructions are compared.

Figure 30:
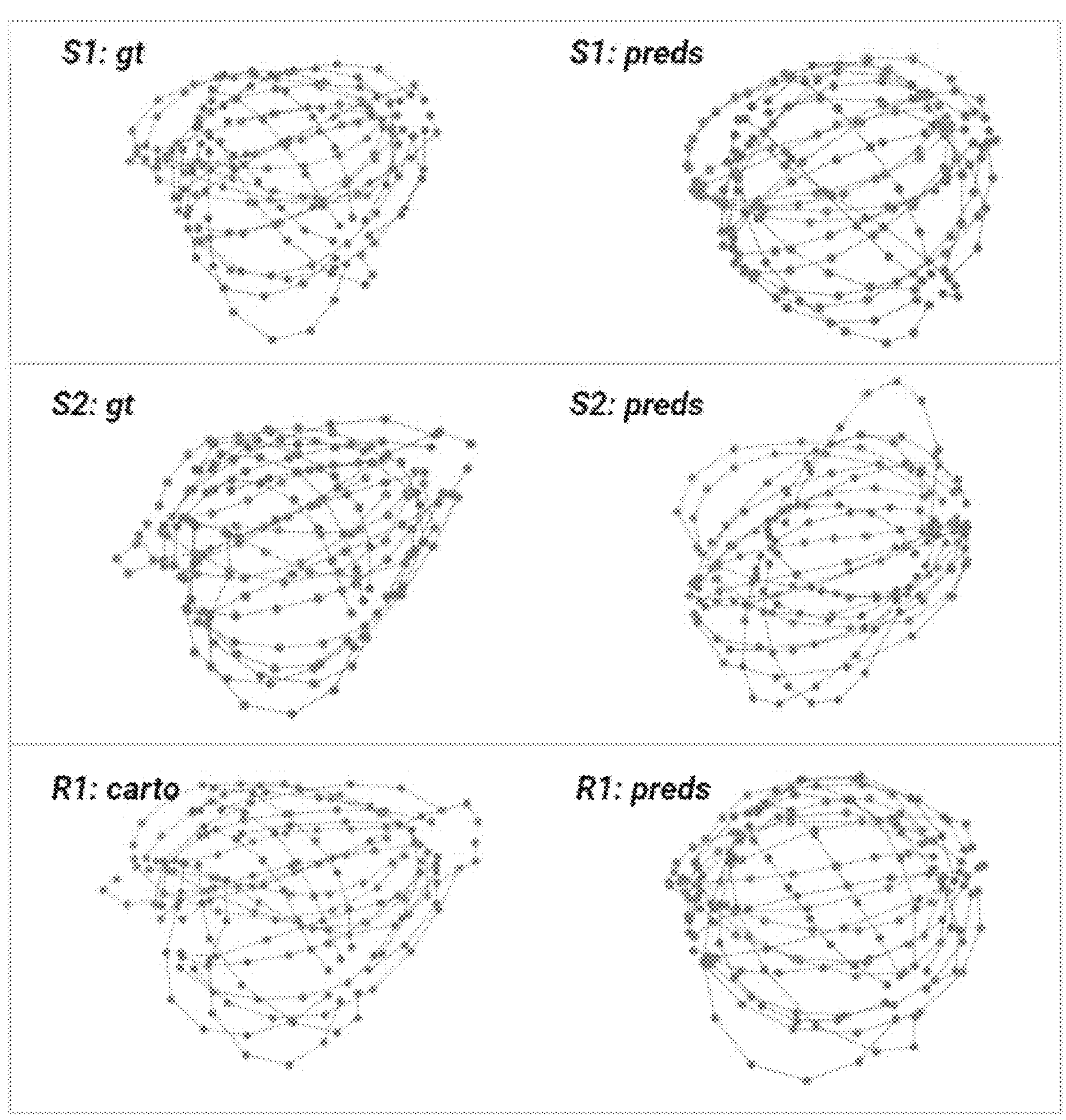
FIG. 30 shows visualizations of ground truth data and predicted reconstructions.

The error of estimating the center of mass varies especially strongly between real and simulated data (R1: 3.62 mm, S1: 1.15 mm, and S2: 1.7 mm). This could be due to errors of the CARTO navigation system. Since the different positions of the BC are estimated at different time points they might not integrate well in space and are influenced by the movement of the patient. FIG. 30 shows visualizations of ground truth data (left panel) and the corresponding predicted reconstructions (right panel) for three different datasets (S1, S2, R1).

For dataset S1, a local score of 1.4 mm is obtained for threshold 30. This calculates the accuracy in a 30 mm radius around each electrode. With good local accuracy, multiple EGF maps can be compared. Even further, important conclusions can be drawn, such as whether two EGF maps show the same source. An example of this can be found in FIG. 31, which shows recordings and EGF results obtained from two different positions measuring the same source.

Animal Data: Pull Back Experiment

Real ground truth information about the position and shape of the BC in the atrium can be extracted from fluoroscopic images. In an animal experiment, the BC catheter was placed into an atrium, and for every BC position a recording was made alongside a fluoroscopic image. From the fluoroscopic images, no 3D shapes could be reconstructed, since the electrodes were not visible and only one view was provided. Therefore, the following experiment was constructed. The physician pulled out the catheter by 5 mm after each recording. Then the recordings were fed through our constrained autoencoder model to reconstruct the electrode locations based on the QRS signals measured. The distances of the distal tips of the different BC positions were compared. Overall the average distance between the reconstructed positions was 4.3 mm±1.3 mm. Assuming that the tip of the BC moved 5 mm each time, an error of 1.4 mm±0.6 mm was calculated. In FIG. 32, the change of location is displayed based on the fluoroscopic images and based on the predictions of the autoencoder model. In the left panel of FIG. 32, the fluoroscopic image for the first BC position is displayed. Black crosses mark the distal and proximal tip of the first BC position. AB denotes the ablation catheter and CS the coronary sinus catheter. The blue dot marks the distal tip of the next 6 BC positions, which have been extracted from other fluoroscopic images. In the right panel of FIG. 32, the location and shape of seven BC positions are predicted via an autoencoder model based on the QRS complex that has been measured. Blue dots mark the distal tip of each BC position.

Alignment to Anatomy

In this section, the performance of the anatomy alignment algorithm is assessed. For the recordings in dataset R3, 3D reconstructions are computed using the auto-encoder model described above, and then aligned with the segmentation of the corresponding CT. A parameter to determine landmarks is set to 3 mm. As convergence criteria for the iterative alignment, the improvement over the last 5 steps should be less than 0.001.

Figure 33:
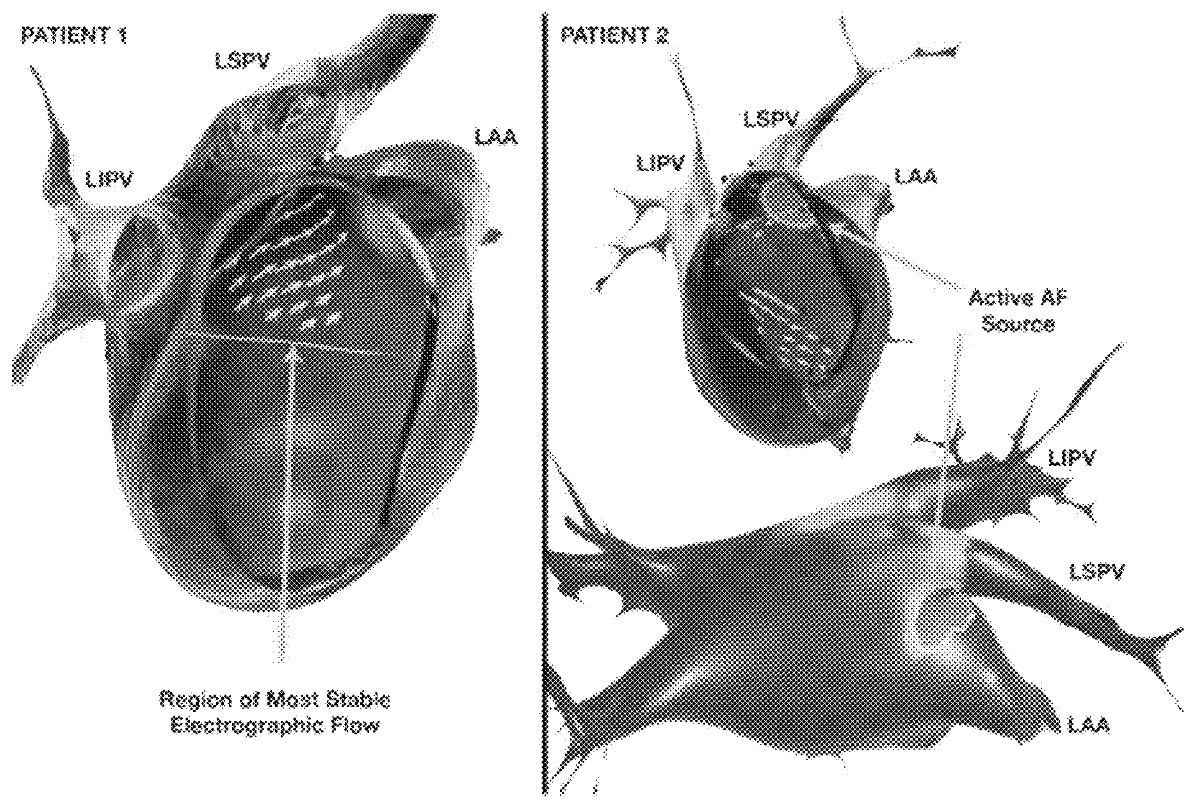
FIG. 33 shows an example of the alignment of anatomy and basket catheter positions.

In FIG. 33, BC positions aligned to the anatomy are displayed. In FIG. 33, instead of showing electrode positions, the summary maps of Ablacon EGF software are visualized, showing sources, rotors, and regions of stable flow. Based on these regions of interest, an expert can qualitatively assess if such an alignment is plausible.

For example, experts verified that for Patient 1 the mapping of the passive rotor to the entry of the LAA is realistic for this patient. To determine the location of the source for Patient 2, a summary map was projected onto the anatomy using the nearest neighbor. It can be seen that the source projects onto the ridge as also predicted from CARTO data.

In FIG. 33, and further as described above, the alignment of anatomy and BC positions is visualized. The EGF summary maps of Ablacon are projected on the surface of the BC positions. For Patient 1, a cutting plane is displayed through the LA, and it can clearly be seen how the BC is placed in the anatomy. The white area indicates a rotor and is mapped to the entry of LAA. For Patient 2, the location of a source is displayed using a cutting plane and projecting the summary EGF map onto the anatomy surface. It can be clearly seen that the source is located on the ridge.

Figure 34:
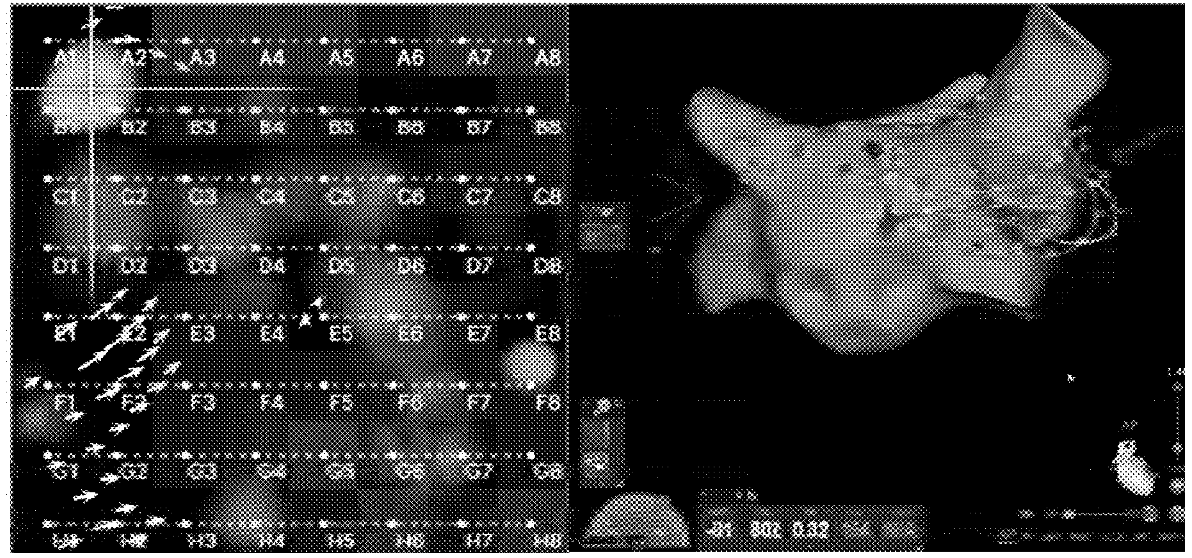
FIG. 34 shows an EGF summary map and corresponding CARTO screenshot.

For quantitative assessment, the location of the strongest source for all patients was annotated by experts using results provided by the methods described and disclosed herein and those of the CARTO system. The LA was separated into 13 predefined anatomical regions (see FIGS. 4A and 4B) to determine the location of a source. The regions are denoted: roof, ridge, appendage, lateral wall, anterior wall, septum, left upper pulmonary vein (LUPV), left inferior pulmonary vein (LIPV), posterior wall, inferior wall, coronary sinus, right inferior pulmonary vein (RIPV) and right upper pulmonary vein (RUPV). To determine the location of the source using CARTO, three experts independently inspected the CARTO screenshots and the Ablacon EGF source maps (see FIG. 34). In FIG. 34, experts annotated the regions of the sources based on CARTO screenshots and summary EGF maps computed using Ablacon EGF software. On the left of FIG. 34, an EGF summary map shows a source close to electrodes A1, A2, B1 and B2. On the right of FIG. 34, a corresponding CARTO screenshot of the BC position is displayed. A red arrow points to the location of electrodes A1, B1, A2 and B2. The anatomy is visualized in antero-posterior (AP) view, and therefore rough estimates of anatomical regions are possible.

Regions assigned based on our anatomy alignment and those based on CARTO were next compared. The same or a neighboring region was assigned in 83% of the cases. Specifically, the same region was assigned in 50% of cases and a neighboring region in 33% of cases. In a total of 3 cases (17%), the allocation was different. FIG. 35 is a table listing source locations estimated using CARTO and the method described and disclosed herein. In FIG. 35, the location of the prevalent source is determined with two methods, based on CARTO and based on our methods and techniques. Rows colored in green indicate that the same or an adjacent region was predicted. Red rows show the patients for whom the predictions did not match.

Discussion

Realistic Shapes and Deformations of BCs

A first issue relates to learning realistic shapes and deformations of BCs. Previous models (i.e., Denner) have predicted reconstructions with zigzags along splines and show a tendency to team undeformed BC shapes. In this work, it can be shown that realistic shapes can be estimated by introducing a (Conv layer and additional losses such as curvature and torsion losses, which indirectly model the stiffness of the splines. According to our hypothesis, these changes also had a positive effect on the overall deformation score. The analysis of the simulated data showed that the ground truth was better reproduced with the Conv layer and the additional losses. It can be argued that the problem of learning unrealistic zigzag along splines was eliminated with these changes.

A statistical shape model was developed for learning the correct deformation of BCs. The shape model captures meaningful dimensions of change. The first dimension captures 47% of variance and represents the stretching of the BC. In particular, learning of longitudinal deformation was improved by including the shape model as a loss. The deformation score was improved to 4 mm. Surprisingly, there was no significant difference between using a shape model with only the first component and using six components. This could be explained by the high variance covered by the first component. The main challenge in teaming the space of QRS morphology and BC deformations simultaneously is that the network can bend either the BC or the space. Therefore, additional constraints could be helpful such as a Lipschitz continuity constraint that could enforce continuous changes of similarity of the QRS morphology and similarity of the positions in x,y,z.

In summary, all changes described and disclosed herein resulted in improved performance. Overall, the deformation score was improved from 5.6±2.6 mm to 4.0±1.6 mm on simulated data. While learning realistic shapes can be ensured by the modifications, learning correct deformations can still be improved.

Accuracy of 3D Reconstructions

Another issue relates to the accuracy of 3D reconstructions. The accuracy of navigation systems is often assessed using phantoms (see, e.g., Bourier et al.) due to the lack of ground truth for reconstructions in the human heart. Therefore, it is challenging to assess the overall accuracy of our model. In the work described and disclosed herein, this problem is addressed from different angles. Firstly, we simulate QRS complexes that are of comparable complexity to QRS data recorded in real patients. The accuracy of 3D reconstructions measured for simulated data is 4.4-1.8 mm overall and 1.4 mm in a 30 mm neighborhood. The deformation score achieves a value of 4 mm and the location of the center of mass is estimated with an error of 1.2 mm. One limitation of the simulation is the lack of modeling noise. Furthermore, the QRS complexes are simulated directly, so the preprocessing pipeline of the proposed model is not tested. Both of these factors could result in lower accuracy with real data. In addition, accuracy may vary depending on the density of electrodes in space. Therefore, the representation of the accuracy value in one number may not reflect the full complexity of the problem. Secondly, an experiment was performed on a canine model in which a BC was retracted in increments of 5 mm. When reconstructed using our model, the error in estimating the position of the tip of the BC was 1.4±0.6 mm. These are promising results, as they are similar to the center of mass values of the simulated data which were 1.2 mm. The general applicability of these results is limited due to the size of the dataset, which consists of only 7 recordings from one animal. In addition, the tip of the BC may have moved more or less than 5 mm in the human heart. The results would be more meaningful if the BC positions could have been reconstructed from the fluoroscopic images. Furthermore, these results were recorded in an animal model and therefore may not be as applicable to human patients.

3D reconstructions predicted from human patients lack ground truth data. Therefore, a comparison is made with 3D reconstructions from a third-party navigation system. This navigation system produces unrealistic deformations of the BC, and it is therefore questionable how accurately such a system performs. In addition, due to sensitivity to body and cardiac motion, the results could be even less accurate if there is a long time between recordings. The reconstructions were calculated from screenshots, and annotation errors cannot be completely ruled out either. Therefore, some question arises about whether the data are close to ground truth data. The comparison shows an average electrode distance of 7.3 mm, a deformation score of 5.2 mm, a center of mass score of 3.6 mm, and a local score of 3.3 mm with a threshold of 30 mm. In particular, the error of localizing the center of mass is increased compared to the simulation results and the results of the canine model. This could indicate errors of the third-party navigation system over time, and it might not reflect the true accuracy of our model in human patients.

In conclusion, overall performance is better for the simulated data than real data, which might be due to the simplification of the simulation process. The deformation score is similar for simulated data and the real data compared to CARTO, whereas the center of mass difference shows large deviations. However in the canine mode, the point accuracy is comparable to the center of mass difference of the simulated data. Overall, more experiments are needed for correctly assessing the accuracy of the model on real data. So far the accuracy is estimated to be in the range of 4.4 mm to 7.3 mm.

Accuracy of Alignment with the Anatomy Model

The quality of the alignment of reconstructions with anatomy depends on several factors. First, the quality of the reconstructions plays a major role as the shape of the BC is matched to the shape of the anatomy. Second, the number of BC positions in a procedure affects the solution space. In particular, if there is only one position, many different solutions will fulfill all constraints. Thus, no optimal solution will be found. However, the current results show that in 83% of the cases, the position and orientations are roughly estimated as in the CARTO system. So it can be assumed that the three proposed constraints are relevant and the initialization is appropriate. To find the optimal solution, further constraints are needed. A score that identifies which electrode is in contact with the atrial wall is therefore proposed, which may be accomplished by processing the atrial waves.

In summary, the results suggest that the proposed constraints are relevant for identifying plausible positioning in the LA. Further constraints are needed to provide an optimal solution, and a wall contact score is proposed for this purpose.

Figure 36:
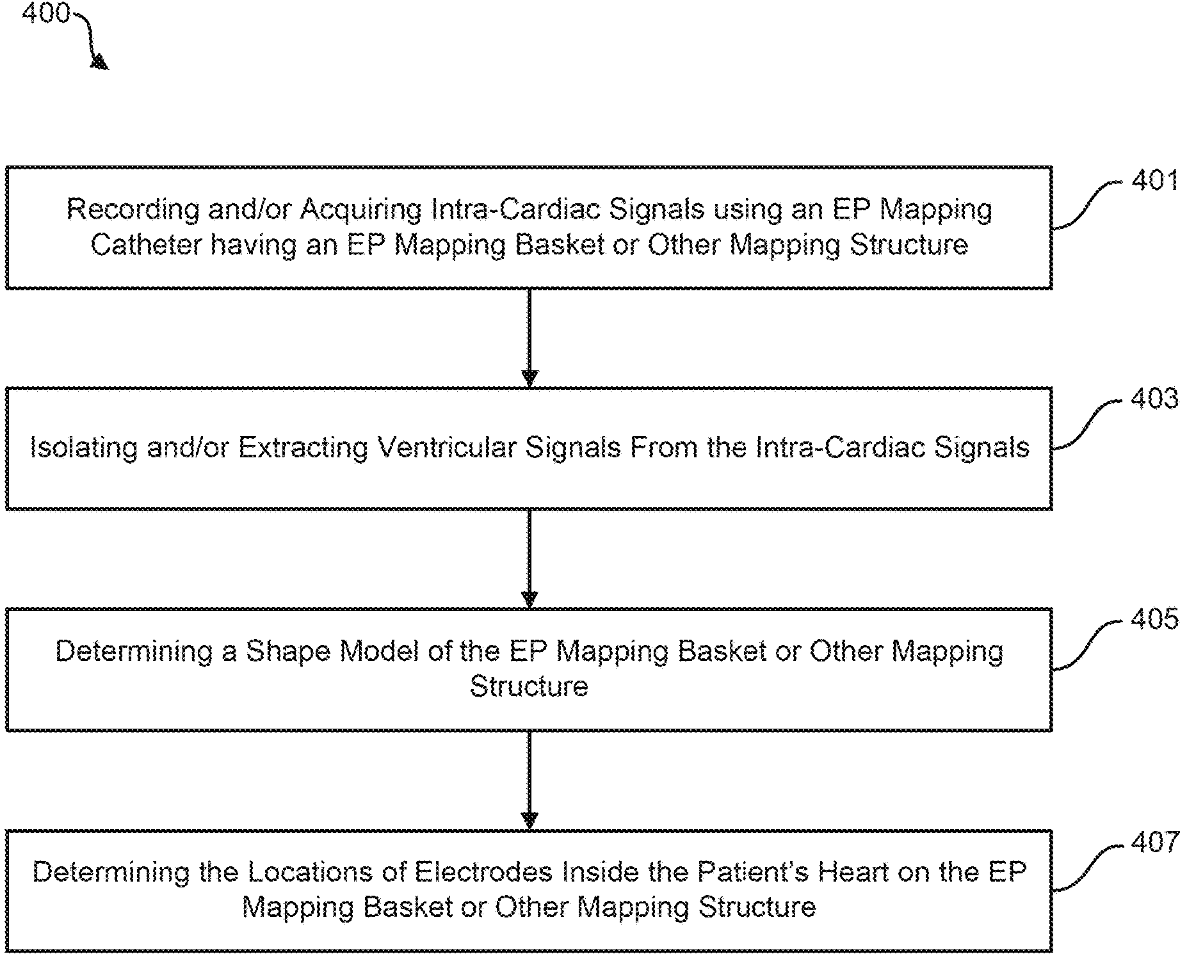
FIG. 36 shows one embodiment of a method according to some embodiments.

Referring now to FIG. 36, there is shown one embodiment of a method according to some embodiments. In method 400, step 401 comprises recording and/or acquiring intracardiac signals using an EP mapping catheter having an EP mapping basket or other EP mapping structure. Step 403 comprises isolating and/or extracting ventricular signals from the intra-cardiac signals; At step 405, a shape model of the EP mapping basket or other EP mapping structure is determined. At step 407, the locations of electrodes on the EP mapping basket or other EP mapping structure inside the patient's heart are determined.

CONCLUSIONS

The challenge of electroanatomical mapping is to create a static visualization of a dynamical system. Approaches based on magnetic, current, and impedance 3D reconstruction are highly influenced by breathing and cardiac movement. Biosignal-based approaches, however, reconstruct electrode positions dependent on QRS signatures measured. This is a measurement taken directly in the heart and are therefore independent of heart and body movement. Furthermore, biosignals can be used for retrospective analysis since no extra recording or hardware is required.

Some biosignal-based approaches fall short of correctly estimated shapes of the BC. Here, a new NN is proposed that successfully learns realistic shapes and improves the learning of BC deformations. One such NN is a Siamese autoencoder with two latent spaces connected by a convolutional layer. Additional losses indirectly model the stiffness of the splines. Furthermore, an SSM is developed and included in a loss to enable the learning of a wider range of deformations. Overall the deformation score has been improved from 5.6±2.6 mm to 4±1.6 mm.

The overall accuracy of the model was evaluated based on simulated, patient, and animal data. The local accuracy is estimated to be between 1.4 mm and 3.34 mm for a 30 mm neighborhood. This enables a reliable comparison of electrographic flow maps for multiple BC positions. With this reconstruction, it can be determined if two sources recorded at different positions are the same or different sources. The overall accuracy is estimated to be between 4.4 mm and 7.3 mm. A hybrid approach connecting biosignal and magnetic reconstructions may also be employed to increase overall accuracy. Mapping of 3D reconstruction into MRI/CT model is commonly performed by registration with intraprocedural anatomy information. Whereas the 3D reconstructions are often mapped outside of the intraprocedural anatomy, indicating a mismatch. In this thesis, three priors are used to map the reconstructions into an anatomy model of LA. (1) All electrodes should be located inside the anatomy, (2) the direction of inserting the BC is taken into account, and (3) the direction of maximum amplitude in the reconstructed space should be pointing to the mitral valve. In 83% of the cases, these constraints were sufficient to find a plausible fit. However, to find an optimal solution more constraints are required. The distance to the wall could be estimated based on atrial waves and included in the optimization.

In conclusion, new algorithms for biosignal-based reconstruction and anatomy alignment have been developed. These enable more realistic reconstructions of BC shapes and also permit extraction of global information. Without extra hardware, the generation of a panoramic map of a whole atrium is made possible by visualizing the electrographic flow on the surface of an anatomy model.

The methods described and disclosed herein may be generalized and extended to other types of catheters beyond BCs, including, but not limited to, multielectrode mapping catheters, circular loop catheters; five-splined mapping catheters (e.g., PentaRay®, catheter from Biosense Webster), linear catheters (e.g., Decapolar® catheter from Biosense Webster); grid catheters (e.g., HD Grid® catheters from Abbott); mini-basket catheters (e.g., Orion® catheters from Boston Scientific); and other EP mapping catheter designs. In addition, the anatomy alignment algorithms described and disclosed herein may be extended to the RA. Furthermore, a Lipschitz continuity constraint can be included to restrict the similarity of QRS morphology to the similarity of the position in x,y,z. A score could be provided that indicates if an electrode has wall contact based on the morphology of atrial waves. An additional constraint for electrodes touching the wall can be employed to limit the solution space of anatomy alignment algorithms.

Further embodiments are disclosed herein or will become apparent to those skilled in the art after having read and understood the claims, specification and drawings hereof.

It will now be seen that the various systems, devices, components and methods disclosed and described herein are capable of detecting with considerable accuracy and precision the locations and types of sources of cardiac rhythm disorders in a patient's heart, diagnosing same, and making better informed and more accurate and likely-to-succeed treatment decisions for patients.

In view of the structural and functional descriptions provided herein, those skilled in the art will appreciate that portions of the described devices and methods may be configured as methods, data processing systems, or computer methods. Accordingly, these portions of the devices and methods described herein may take the form of a hardware embodiment, a software embodiment, or an embodiment combining software and hardware, such as shown and described with respect to computer system 300 illustrated in FIG. 1B. Furthermore, portions of the devices and methods described herein may be a computer method stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, systems, and computer methods. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in an individual block, plurality of blocks, or block diagram.

In this regard, FIG. 1B illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, and/or transform sensor or electrode data and image data associated with the analysis of cardiac electrical activity and the carrying out of the combined electrophysiological mapping and analysis of the patient's heart 10 and ablation therapy delivered thereto. Likewise, systems 100 shown in FIGS. 2A and 2B may be modified to permit the acquisition of both body surface and intra-cardiac electrode data simultaneously or sequentially. In addition, the various components, devices and systems 300 illustrated in FIGS. 1A through 2B can be implemented and used sequentially and/or apart from one another, including in different locations, and may also be implemented and used together in a unified interconnected system 300.

It will now be seen that the various systems, devices, components and methods disclosed and described herein are capable of detecting with considerable accuracy and precision the locations of sources of cardiac rhythm disorders in a patient's heart.

What have been described above are examples and embodiments of the devices and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are possible. Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing outlines features of several embodiments so that those skilled in the art may better understand the detailed description set forth herein. Those skilled in the art will now understand that many different permutations, combinations and variations of the systems, devices, components and methods described and disclosed herein fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems, both in the use of electrophysiological mapping systems and in the use of cardiac ablation systems.

LIST OF ABBREVIATIONS

AF Atrial Fibrillation
BC Basket Catheter
CT Computed Tomography
ECG Electrogram
EGM Electrocardiogram
LAA Left Atrial Appendage
LIPV Left Inferior Pulmonary Vein
LUPV Left Upper Pulmonary Vein
PCA Principle Component Analysis
RBF Radial Basis Function
RIPV Right Inferior Pulmonary Vein
RSB Reconstructed Space of BCs
RUPV Right Upper Pulmonary Vein
SSM Statistical Shape Model
SVC Superior Vena Cava

BIBLIOGRAPHY

1. G. Lippi, F. Sanchis-Gomar and G. Cervellin. "Global epidemiology of atrial fibrillation: An increasing epidemic and public health challenge". in International Journal of Stroke: 16.2 (February 2021), pages 217-221. issn: 1747-4930, 1747-4949. doi: 10.1177/1747493019897870. url: http://journals.sagepub.com/doi/10.1177/(urlseen 07/03/2022).
2. S. Rolf, G. Hindricks, P. Sommer, S. Richter, A. Arya, A. Bollmann, J. Kosiuk and E. Koutalas. "Electroanatomical mapping of atrial fibrillation: Review of the current techniques and advances". in Journal of Atrial Fibrillation: 7.4 (31 Dec. 2014), page 1140. issn: 1941-6911. doi: 10.4022/jafib.1140. url: https://www.ncbi.nlm.nih.gov/pmc/articles/PMC5135200/(urlseen 08/03/2022).
3. Y.-H. Kim, S.-A. Chen, S. Ernst, C. E. Guzman, S. Han, Z. Kalarus, C. Labadet, Y.-J. Lin, L.-W. Lo, A. Nogami, E. B. Saad, J. Sapp, C. Sticherling, R. Tilz, R. Tung, Y. G. Kim and M. K. Stiles. "2019 APHRS expert consensus statement on three-dimensional mapping systems for tachycardia developed in collaboration with HRS, EHRA, and LAHRS". In Journal of Arrhythmia: 36.2 (April 2020), pages 215-270. issn: 1880-4276, 1883-2148. doi: 10.1002/joa3.12308. url: https://onlinelibrary.wiley.com/doi/10.1002/joa3. 12308 (urlseen 11/03/2022).
4. L. Gepstein, G. Hayam and S. A. Ben-Haim. "A Novel Method for Nonfluoroscopic Catheter-Based Electroanatomical Mapping of the Heart: In Vitro and In Vivo Accuracy Results". in Circulation: 95.6 (18 Mar. 1997), pages 1611-1622. issn: 0009-7322, 1524-4539. doi: 10.1161/01.CIR.95.6.1611. url: https://www.ahajournals.org/doi/10.1161/01.CIR.95.6.1611 (urlseen 11/03/2022).
5. S. Denner. "GPS in the Heart—Towards a Purely Biosignal Based intracardiac Navigation System". Master's Thesis. Munich: Technical University of Munich, 2021.
6. S. Jarvis and S. Saman. "Cardiac system 1: anatomy and physiology" in Nursing Times: 114:2 (2018), pages 34-37.
7. R. J. Hunter, Y. Liu, Y. Lu, W. Wang and R. J. Schilling. "Left Atrial Wall Stress Distribution and Its Relationship to Electrophysiologic Remodeling in Persistent Atrial Fibrillation". in Circulation: Arrhythmia and Electrophysiology: 5.2 (1 Apr. 2012), pages 351-360. doi: 10.1161/CIRCEP.111.965541. url: https://www.ahajournals.org/doi/10.1161/CIRCEP.111.965541 (urlseen 02/03/2022).
8. R. Mandapati, A. Skanes, J. Chen, O. Berenfeld and J. Jalife. "Stable Microreentrant Sources as a Mechanism of Atrial Fibrillation in the Isolated Sheep Heart". in Circulation: 101.2 (18 Jan. 2000), pages 194-199. issn: 0009-7322, 1524-4539. doi: 10.1161/01. CIR.101.2.194. url: https://www.ahajournals.org/doi/10.1161/01.CIR.101.2.194 (urlseen 13/03/2022),
9. J. Heeringa, D. A. van der Kuip, A. Hofman, J. A. Kors, G. van Herpen, B. H. Stricker, T. Stijnen, G. Y. Lip and J. C. Witteman. "Prevalence, incidence and lifetime risk of atrial fibrillation: the Rotterdam study". in European Heart Journal: 27.8 (March 2006), pages 949-953. issn: 0195-668X. doi: 10.1093/eurheartj/ehi825. eprint: https://academic.oup.com/eurheartj/article-pdf/27/8/949/9626276/ehi825.pdf. url: https://doi.org/10.1093/eurheartj/ehi825.
10. A. Hall. Understanding ECG: The Complete Guide to 12-Lead EKG Interpretation. Independently Published, 2019. isbn: 9781090705730. url: https://books.google.de/books?id=BwdRwwEACAAJ.
11. E. A. Ashley and J. Niebauer. Cardiology Explained. London: Remedica, 2004.
12. F. Kusumoto and MyiLibrary. Understanding intracardiac EGMs and ECGs. OCLC: 1264842736. Chichester, UK: Wiley-Blackwell, 2010. isbn: 9781405184106.
13. T. Oesterlein, D. Frisch, A. Loewe, G. Seemann, C. Schmitt, O. Dössel and A. Luik. "Basket-Type Catheters: Diagnostic Pitfalls Caused by Deformation and Limited Coverage". in BioMed Research International: 2016 (13 Dec. 2016), e5340574. issn: 2314-6133. doi: 10.1155/2016/5340574. url: https://www.hindawi.com/journals/bmri/2016/5340574/(urlseen 31/01/2022).
14. T. Szili-Torok, Z. Kis, R. Bhagwandien, S. Wijchers, S.-C. Yap, M. Hoogendijk, N. Dumas, P. Haeusser, T. Geczy, M. H. Kong and P. Ruppersberg. "Functional electrographic flow patterns in patients with persistent atrial fibrillation predict outcome of catheter ablation". In Journal of Cardiovascular Electrophysiology: 32.8 (august 2021), pages 2148-2158. issn: 1045-3873, 1540-8167. doi: 10.1111/jce.15115. url: https://onlinelibrary.wiley.com/doi/10.1111/jce.15115 (urlseen 04/03/2022).
15. C. R. News. Abbott to acquire Topera and Advanced Cardiac Therapeutics. url: https://4bmyaa9xaf0tl8hb3wxlj3nh-wpengine.netdna-ssl.com/wp-content/uploads/sites/12/2014/10/Firmap_main-_Main.jpg (urlseen 04/03/2022).
16. B. K. Horn and B. G. Schunck. "Determining optical flow". In Artificial Intelligence: 17.1 (1981), pages 185-203. issn: 0004-3702. doi: https://doi.org/10.1016/0004-3702(81)90024-2. url: https://www.sciencedirect.com/science/article/pii/0004370281900242.
17.1. Goodfellow, Y. Bengio and A. Courville. Deep Learning. http://www.deplearningbook.org. MIT Press, 2016.
18. B. O. Ayinde and J. M. Zurada. "Deep Learning of Constrained Autoencoders for Enhanced Understanding of Data". in IEEE Transactions on Neural Networks and Learning Systems: 29.9 (September 2018), pages 3969-3979. issn: 2162-237X, 2162-2388. doi: 10.1109/TNNLS.2017.2747861. url: https://ieeexplore.ieee.org/document/8051252/(urlseen 14/03/2022).

19. M. Rudolph, B. Wandt and B. Rosenhahn. "Structuring Autoencoders". in 2019 IEEE/CVF International Conference on Computer Vision Workshop (ICCVW): 2019, pages 615-623. doi: 10.1109/ICCVW.2019.00075.

20. Y. Xu and M. Vaziri-Pashkam. "Limits to visual representational correspondence between convolutional neural networks and the human brain", in Nature Communications: 12.1 (December 2021), page 2065. issn: 2041-1723. doi: 10.1038/s41467-021-22244-7. url: http://www.nature.com/articles/s41467-021-22244-7 (urlseen 14/03/2022).

21. T. Hope, Y. S. Resheff and I. Lieder. Learning TensorFlow: A Guide to Building Deep Learning Systems. 1st. O'Reilly Media, Inc., 2017. isbn: 1491978511.

22. G. Koch, R. Zemel and R. Salakhutdinov. "Siamese Neural Networks for One-shot Image Recognition". In 2015.

23. L. Zollei, W. Grimson, A. Norbash and W. Wells. "2D-3D Rigid Registration of XRay Fluoroscopy and CT Images Using Mutual Information and Sparsely Sampled Histogram Estimators." In January 2001: pages 696-703.

24. W. Kabsch. "A solution for the best rotation to relate two sets of vectors". in Acta Crystallographica Section A: 32.5 (September 1976), pages 922-923. doi: 10.1107/S0567739476001873. url: https://doi.org/10.1107/S0567739476001873.

25. J. Farre, R. H. Anderson, J. A. Cabrera, D. Sanchez-*Quintana*, J. M. Rubio, J. Romero and F. Cabestrero. "Fluoroscopic Cardiac Anatomy for Catheter Ablation of Tachycardia". in Pacing and Clinical Electrophysiology: 25.1 (January 2002), pages 76-94. issn: 0147-8389, 1540-8159. doi: 10.1046/j.1460-9592.2002.00076.x. url: http://doi.wiley.com/10.1046/j.1460-9592.2002.00076.x (urlseen 11/03/2022).

26. Y. Jiang, D. Farina, M. Bar-Tal and O. Dossel. "An Impedance-Based Catheter Positioning System for Cardiac Mapping and Navigation". In IEEE Transactions on Biomedical Engineering: 56.8 (august 2009), pages 1963-1970. issn: 0018-9294, 1558-2531. doi: 10.1109/TBME.2009.2021659. url: https://ieeexplore.ieee.org/document/4915797/(urlseen 11/03/2022).

27. F. Bourier, R. Fabrig, P. Wang, P. Santangeli, K. Kurzidim, N. Strobel, T. Moore, C. Hinkel and A. Al-Ahmad. "Accuracy Assessment of Catheter Guidance Technology in Electrophysiology Procedures: A Comparison of a New 3D-Based Fluoroscopy Navigation System to Current Electroanatomic Mapping Systems". in Journal of Cardiovascular Electrophysiology: 25.1 (January 2014), pages 74-83. issn: 10453873. doi: 10.1111/jce. 12264. url: https://onlinelibrary.wiley.com/doi/10.1111/jce.12264 (urlseen 11/03/2022).

28. P. Sommer. "3D Mapping for PVI—Geometry, Image Integration and Incorporation of Contact Force Into Work Flow". in Journal of Atrial Fibrillation: 10.6 (April 2018), page 1795. issn: 1941-6911. doi: 10.4022/jafib.1795. url: http://www.jafib.com/published.php?type=full&id=1795 (urlseen 12/03/2022).

29. S. K. Sonovane, D. M. Milner, S. P. Singh, A. K. Abdel Aal, K. S. Shahir and A. Chaturvedi. "Comprehensive Imaging Review of the Superior Vena Cava". In RadioGraphics: 35.7 (November 2015), pages 1873-1892. issn: 0271-5333, 1527-1323. doi: 10.1148/rg. 2015150056. url: http://pubs.rsna.org/doi/10.1148/rg.2015150056 (urlseen 14/03/2022).

30. L. Tenbrink. "Investigating dense body surface electrode data for non-invasive detection of intracardiac arrhythmia drivers". Master's Thesis. Munich: Technical University of Munich, 2021.

31. M. Ester, H.-P. Kriegel, J. Sander and X. Xu. "A density-based algorithm for discovering clusters in large spatial databases with noise". in Proceedings of the Second International Conference on Knowledge Discovery and Data Mining: KDD'96. Portland, Oregon: AAAI Press, 2 Aug. 1996, pages 226-231. (urlseen 26/01/2022).

32. D.-h. Xu, B.-h. Wang, Y. Zhang, H-d. Sheng and Y.-1. Ye. "[3D reconstruction of the heart model based on the region growing segmentation]". In Zhongguo yi liao qi xie za zhi=Chinese journal of medical instrumentation: 31.1 (January 2007), pages 17-21. issn: 1671-7104. url: http://europepmc.org/abstract/MED/17432119.

33. G. W. Beeler and H. Reuter. "Reconstruction of the action potential of ventricular myocardial fibres". in The Journal of Physiology: 268.1 (1 Jun. 1977), pages 177-210. issn: 00223751. doi: 10.1113/jphysiol.1977.sp011853. url: https://onlinelibrary. wiley-.com/doi/10.1113/jphysiol.1977.sp011853 (urlseen 31/01/2022).

34. W. Kahlmann, E. Poremba, D. Potyagaylo, O. Dössel and A. Loewe. "Modelling of patient-specific Purkinje activation based on measured ECGs". In Current Directions in Biomedical Engineering: 3.2 (1 Sep. 2017), pages 171-174. issn: 2364-5504. doi: 10.1515/cdbme-2017-0177. url: https://www.degruyter.com/document/doi/10.1515/cdbme-2017-0177/html (urlseen 31/01/2022).

35. R. E. Ideker, W. Kong and S. Pogwizd. "Purkinje Fibers and Arrhythmias". in Pacing and Clinical Electrophysiology: 32.3 (march 2009), pages 283-285. issn: 01478389, 15408159. doi: 10.1111/j.1540-8159.2008.02232.x. url: https://onlinelibrary.wiley.com/doi/10.111/j.1540-8159.2008.02232.x (urlseen 31/01/2022).

36. S. Nattel. "New ideas about atrial fibrillation 50 years on". In: Nature 415.6868 (2002), pp. 219-226.

37. W. M. Feinberg, J. L. Blackshear, A. Laupacis, R. Kronmal, and R. G. Hart. "Prevalence, age distribution, and gender of patients with atrial fibrillation: analysis and implications". In: Archives of internal medicine 155.5 (1995), pp. 469-473.

38. P. A. Wolf, E. J. Benhamin, A. J. Belanger, W. B. Kannel, D. Levy, and R. B. D'Agostino. "Secular trends in the prevalence of atrial fibrillation: the Framingham Study". In: American heart journal 131.4 (1996), pp. 790-795.

39. M. Keller. Formation of Intracardiac Electrograms under Physiological and Pathological Conditions. Vol. 21. KIT Scientific Publishing, 2014.

40. A. F. Members, A. J. Camm, G. Y. Lip, R. De Caterina, I. Savelieva, D. Atar, S. H. Hohnloser, G. Hindricks, P. Kirchhof, E. C. for Practice Guidelines (CPG), et al. "2012 focused update of the ESC Guidelines for the management of atrial fibrillation: an update of the 2010 ESC Guidelines for the management of atrial fibrillation Developed with the special contribution of the European Heart Rhythm Association". In: European heart journal 33.21 (2012), pp. 2719-2747.

41. H. Calkins, J. Brugada, D. L. Packer, R. Cappato, S.-A. Chen, H. J. Crijns, R. J. Damiano Jr, D. W. Davies, D. E. Haines, M. Haissaguerre, et al. "HRS/EHRA/ECAS Expert Consensus Statement on Catheter and Surgical Ablation of Atrial Fibrillation: Recommendations for Personnel, Policy, Procedures and Follow-Up: A report of the Heart Rhythm Society (HRS) Task Force on Catheter and Surgical Ablation of Atrial Fibrillation Developed in partnership with the European Heart Rhythm Association (EHRA) and the European Cardiac Arrhythmia Society (ECAS); in collaboration with the American College of Cardiology (ACC), American Heart Association (AHA), and the Society of Thoracic Surgeons (STS). Endorsed and Approved by the governing bodies of the American College of Cardiology, the American Heart Association, the European Cardiac Arrhythmia Society, the European Heart Rhythm Association, the Society of Thoracic Surgeons, and the Heart Rhythm Society." In: Europace 9.6 (2007), pp. 335-379.

42. K. Nademanee, J. McKenzie, E. Kosar, M. Schwab, B. Sunsaneewitayakul, T. Vasavakul, C. Khunnawat, and T. Ngarmukos. "A new approach for catheter ablation of atrial fibrillation: mapping of the electrophysiologic substrate". In: Journal of the American College of Cardiology 43.11 (2004), pp. 2044-2053.

[8] M. Haissaguerre, P. Jais, D. C. Shah, A. Takahashi, M. Hocini, G. Quiniou, S. Garrigue, A. Le Mouroux, P. Le Métayer, and J. Clémenty. "Spontaneous initiation of atrial fibrillation by ectopic beats originating in the pulmonary veins". In: New England Journal of Medicine 339.10 (1998), pp. 659-666.

[43. L. Nagaraju, D. Menon, and P. F. Aziz. "Use of 3D electroanatomical navigation (CARTO-3) to minimize or eliminate fluoroscopy use in the ablation of pediatric supraventricular tachyarrhythmias". In: Pacing and Clinical Electrophysiology 39.6 (2016), pp. 574-580.

44. F. Bourier, R. Fahrig, P. Wang, P. Santangeli, K. Kurzidim, N. Strobel, T. Moore, C. Hinkel, and A. AL-AHMAD. "Accuracy assessment of catheter guidance technology in electrophysiology procedures: a comparison of a new 3D-based fluoroscopy navigation system to current electroanatomic mapping systems". In: Journal of cardiovascular electrophysiology 25.1 (2014), pp. 74-83.

45. A. J. Weinhaus and K. P. Roberts. "Anatomy of the human heart". In: Handbook of cardiac anatomy, physiology, and devices. Springer, 2005, pp. 51-79.

46. R. K. Clark. Anatomy and physiology: understanding the human body. Jones & Bartlett Learning, 2005.

47. J. Sundnes, G. T. Lines, X. Cai, B. F. Nielsen, K.-A. Mardal, and A. Tveito. Computing the electrical activity in the heart. Vol. 1. Springer Science & Business Media, 2007.

48. R. Malathi and J. Krishnan. Recent Advancements in System Modelling Applications: Proceedings of National Systems Conference 2012. Vol. 188. Springer Science & Business Media, 2013.

49. S. Silbernagl, A. Despopoulos, W.-R. Gay, A. Rothenburger, and S. O. Wandrey. Color atlas of physiology. Vol. 5. Thieme Stuttgart, 2009.

50. C. Schmitt, I. Deisenhofer, and B. Zrenner. Catheter ablation of cardiac arrhythmias: a practical approach. Springer Science & Business Media, 2006.

51. Cardiac Rhythm News. Abbott to acquire Topera and Advanced Cardiac Therapeutics. [Online; accessed Jun. 18, 2021]. 2014. url: https://4bmyaa9xaf0tl8hb3wxlj3nh-wpengine.netdna-ssl.com/wp-content/uploads/sites/12/2014/10/Firmap_main_Main.jpg. 52.1. Goodfellow, Y. Bengio, and A. Courville. Deep Learning. http://www.deeplearningbook. org. MIT Press, 2016.

53. Y. LeCun, L. Bottou, Y. Bengio, and P. Haffner. "Gradient-based learning applied to document recognition". In: Proceedings of the IEEE 86.11 (1998), pp. 2278-2324.

54. V. Dumoulin and F. Visin. "A guide to convolution arithmetic for deep learning". In: ArXiv e-prints (March 2016). eprint: 1603.07285.

55. C. Knackstedt, P. Schauerte, and P. Kirchhof. "Electro-anatomic mapping systems in arrhythmias". In: Europace 10.suppl_3 (2008), pp. iii28-iii34.

56. G. Stabile, M. Scaglione, M. del Greco, R. De Ponti, M. G. Bongiorni, F. Zoppo, E. Soldati, R. Marazzi, M. Marini, F. Gaita, et al. "Reduced fluoroscopy exposure during ablation of atrial fibrillation using a novel electro-anatomical navigation system: a multicentre experience". In: Europace 14.1 (2012), pp. 60-65.

57. Y.-H. Kim, S.-A. Chen, S. Ernst, C. E. Guzman, S. Han, Z. Kalarus, C. Labadet, Y.-J. Lin, L.-W. Lo, A. Nogami, et al. "2019 APHRS expert consensus statement on three dimensional mapping systems for tachycardia developed in collaboration with HRS, EHRA, and LAHRS". In: Journal of arrhythmia 36.2 (2020), p. 215.

58. L. Gepstein, G. Hayam, and S. A. Ben-Haim. "A novel method for nonfluoroscopic catheter-based electroanatomical mapping of the heart: in vitro and in vivo accuracy results". In: Circulation 95.6 (1997), pp. 1611-1622.

59. S. Shpun, L. Gepstein, G. Hayam, and S. A. Ben-Haim. "Guidance of radiofrequency endocardial ablation with real-time three-dimensional magnetic navigation system". In: Circulation 96.6 (1997), pp. 2016-2021.

60. G. Nollo, M. Marconcini, L. Faes, F. Bovolo, F. Ravelli, and L. Bruzzone. "An automatic system for the analysis and classification of human atrial fibrillation patterns from intracardiac electrograms". In: IEEE Transactions on Biomedical Engineering 55.9 (2008), pp. 2275-2285.

61. G. Baldazzi, M. Orrù, M. Matraxia, G. Viola, and D. Pani. "Supervised Classification of Ventricular Abnormal Potentials in Intracardiac Electrograms". In: 2020 Computing in Cardiology. IEEE. 2020, pp. 1-4.

62. T. G. Oesterlein, J. Schmid, S. Bauer, A. Jadidi, C. Schmitt, O. Dössel, and A. Luik. "Analysis and visualization of intracardiac electrograms in diagnosis and research: concept and application of KaPAVIE". In: Computer methods and programs in biomedicine (2016), pp. 165-173.

63. M. Zihlmann, D. Perekrestenko, and M. Tschannen. "Convolutional recurrent neural networks for electrocardiogram classification". In: 2017 Computing in Cardiology (CinC). IEEE. 2017, pp. 1-4.

64. G. Mori, S. Belongie, and J. Malik. "Efficient shape matching using shape contexts". In: IEEE Transactions on Pattern Analysis and Machine Intelligence 27.11 (2005), pp. 1832-1837.

65. R. C. Veltkamp. "Shape matching: Similarity measures and algorithms". In: Proceedings International Conference on Shape Modeling and Applications. IEEE. 2001, pp. 188-197.

66. S. Belongie, J. Malik, and J. Puzicha. "Shape matching and object recognition using shape contexts". In: IEEE transactions on pattern analysis and machine intelligence 24.4 (2002), pp. 509-522.

67. R. C. Veltkamp and M. Hagedoom. "State of the art in shape matching". In: Principles of visual information retrieval. Springer, 2001, pp. 87-119.

68. M. Vestner, Z. Lăhner, A. Boyarski, O. Litany, R. Slossberg, T. Remez, E. Rodola, A. Bronstein, M. Bronstein, R. Kimmel, et al. "Efficient deformable shape correspondence via kernel matching". In: 2017 International Conference on 3D Vision (3DV). IEEE. 2017, pp. 517-526.

69. B. Schölkopf, A. Smola, and K.-R. Müller. "Nonlinear component analysis as a kernel eigenvalue problem". In: Neural computation 10.5 (1998), pp. 1299-1319.

70. S. T. Roweis and L. K. Saul. "Nonlinear dimensionality reduction by locally linear embedding". In: science 290.5500 (2000), pp. 2323-2326.

71. J. B. Tenenbaum, V. De Silva, and J. C. Langford. "A global geometric framework for nonlinear dimensionality reduction". In: science 290.5500 (2000), pp. 2319-2323.

72. Y. Bengio and M. Monperrus. "Non-local manifold tangent learning". In: Advances in Neural Information Processing Systems 17.1 (2005), pp. 129-136.

73. L. Van Der Maaten. "Learning a parametric embedding by preserving local structure". In: Artificial Intelligence and Statistics. PMLR. 2009, pp. 384-391.

74. E. Lei, O. Castafteda, O. Tirkkonen, T. Goldstein, and C. Studer. "Siamese neural networks for wireless positioning and channel charting". In: 2019 57th Annual Allerton Conference on Communication, Control, and Computing (Allerton). IEEE. 2019, pp. 200-207.

75. P. Huang, E. Gonultas, S. Medjkouh, O. Castaneda, O. Tirkkonen, T. Goldstein. and C. Studer. "Representation-constrained autoencoders and an application to wireless positioning". In: (2018).

76. L. Tenbrink. "Investigating dense body surface electrode data for non-invasive detection of intracardiac arrhythmia drivers". In: (2021).

77. M. Ester, H.-P. Kriegel, J. Sander, X. Xu, et al. "A density-based algorithm for discovering clusters in large spatial databases with noise." In: kdd. Vol. 96. 34. 1996, pp. 226-231. [44] H. W. Kuhn. "The Hungarian method for the assignment problem". In: Naval research logistics quarterly 2.1-2 (1955), pp. 83-97.

78. D. P. Kingma and J. Ba. "Adam: A method for stochastic optimization". In: arXiv preprint arXiv:1412.6980 (2014).

79. W. Kabsch. "A solution for the best rotation to relate two sets of vectors". In: Acta Crystallographica Section A: Crystal Physics, Diffraction, Theoretical and General Crystallography 32.5 (1976), pp. 922-923.

80. A. Nüchter. 3D robotic mapping: the simultaneous localization and mapping problem with six degrees of freedom. Vol. 52. Springer, 2008.

We claim:

1. A method of determining three-dimensional locations of electrodes of an intra-cardiac electrophysiological (EP) mapping basket, the basket configured to be disposed inside or near an atrium or other heart chamber of a patient's heart, the EP mapping basket comprising a plurality of electrodes arranged in a predetermined spatial configuration, the method comprising:

recording or acquiring, using the EP mapping basket, a data acquisition device, and a computing device, a plurality of intra-cardiac signals while the basket is positioned at different locations inside or near the atrium or other heart chamber, the recorded or acquired intra-cardiac signals each having at least one electrode associated therewith wherein each electrode records cardiac electrical activity from a specific three-dimensional location;

using the computing device, isolating or extracting ventricular signals from at least some of the recorded or acquired intra-cardiac signals using signal processing techniques that differentiate ventricular electrical activity from atrial electrical activity based on characteristic waveform morphologies and timing relationships;

using the computing device, determining, using the extracted or isolated ventricular signals, a statistical shape model of the EP mapping basket by analyzing the spatial relationships between the isolated ventricular signals and correlating signal propagation patterns with known cardiac anatomical structures, wherein the statistical shape model accounts for dynamic deformation of the basket during cardiac motion; and determining, in at least near real-time during the cardiac mapping procedure, three-dimensional locations of the electrodes inside or near the patient's atrium or heart chamber by applying the statistical shape model to the isolated ventricular signals, wherein the determined electrode locations are displayed on a visualization system to guide clinical decision-making during the electrophysiological procedure.

2. The method of claim 1, wherein the computing device employs a neural network or other machine learning architecture to compute, determine or reconstruct the extracted or isolated ventricular signals.

3. The method of claim 2, wherein the computing device employs the neural network or other machine learning architecture to generate a center of mass for each or selected positions of the EP mapping basket.

4. The method of claim 2, wherein the computing device employs the neural network or other machine learning architecture or machine learning algorithm to align or project reconstructions of the EP mapping basket and its electrodes onto an anatomy model of the patient's heart.

5. The method of claim 2, further comprising recording or acquiring at least one body surface signal from the patient using at least one body surface electrode, the at least one body surface signal being acquired or recorded simultaneously or substantially simultaneously with the recorded or acquired intra-cardiac signals.

6. The method of claim 5, further comprising, using the computing device, isolating or extracting at least one ventricular signal from the recorded or acquired body surface signal, and determining, using the extracted or isolated intra-cardiac and at least one body surface ventricular signals and the computing device, the locations of the electrodes inside the patient's heart that are associated with each isolated or extracted ventricular signal.

7. The method of claim 2, wherein the isolated or extracted ventricular signals comprise QRS complexes.

8. The method of claim 2, further comprising moving the basket inside the patient's atrium to different positions, and recording or acquiring intra-cardiac signals at each such position.

9. The method of claim 2, further comprising, using the computing device, removing low-frequency or other artefacts or noise from the recorded or acquired intra-cardiac and/or body surface signals.

10. The method of claim 2, further comprising recording or acquiring a plurality of intra-cardiac signals for each electrode while the basket is in a given position within the patient's atrium, and, using the computing device, isolating or extracting a ventricular signal for each such intra-cardiac signal.

11. The method of claim 2, further comprising, using the computing device, determining changes in the three-dimensional locations and orientations of the basket and the electrodes thereof as the basket is moved around, in or near the patient's atrium or other heart chamber.

12. The method of claim 2, further comprising providing a visual display to a user of the locations of the electrodes and/or basket inside or near the patient's atrium or other heart chamber.

13. The method of claim 2, further comprising, using the computing device and the isolated or extracted ventricular signals, at least one neural network to determine the locations of the electrodes and/or basket inside or near the patient's atrium or other heart chamber.

14. The method of claim 2, wherein the locations of at least one of the electrodes and the basket inside or near the patient's atrium or other heart chamber are provided in a visualization to a user in near real time.

15. A system configured to determine three-dimensional location of electrodes of an intra-cardiac electrophysiological (EP) mapping basket, the basket being configured to be disposed inside or near an atrium or other heart chamber of a patient's heart, the EP mapping basket comprising a plurality of electrodes arranged in a predetermined spatial configuration, the system comprising:

a data acquisition or recording device, and a computing device, the data acquisition or recording device and computing device being operably connected to the EP mapping basket and the electrodes thereof, the data acquisition or recording device being configured to record or acquire a plurality of intra-cardiac signals while the basket is positioned at different locations inside or near the atrium or other heart chamber using the plurality of electrodes, the recorded or acquired intra-cardiac signals each having at least one electrode associated therewith, wherein each electrode records cardiac electrical activity from a specific three-dimensional location;

wherein the computing device is configured to isolate or extract ventricular signals from at least some of the recorded or acquired intra-cardiac signals, using signal processing techniques that differentiate ventricular electrical activity from atrial electrical activity based on characteristic waveform morphologies and timing relationships, and the computing device is further configured to determine, using the extracted or isolated ventricular signals, a statistical shape model of the EP mapping basket by analyzing spatial relationships between the isolated ventricular signals and correlating signal propagation patterns with known cardiac anatomical structures, wherein the statistical shape model accounts for dynamic deformation of the basket during cardiac motion and the three-dimensional locations of the electrodes inside or near the atrium or other heart chamber that are associated with each or a plurality of isolated or extracted ventricular signals by applying the statistical shape model to the isolated ventricular signals in at least near real-time during the cardiac mapping procedure, wherein the computing device is further configured to display the determined electrode locations on a visualization system to guide clinical decision-making during the electrophysiological procedure.

16. The system of claim 15, wherein the computing device comprises a neural network or other machine learning architecture to compute, determine or reconstruct the extracted or isolated ventricular signals.

17. The system of claim 15, wherein the computing device employs a neural network or other machine learning architecture to generate a center of mass for each or selected positions of the EP mapping basket.

18. The system of claim 16, wherein the computing device is configured to employ a neural network or other machine learning architecture or machine learning algorithm to align or project reconstructions of the EP mapping basket and its electrodes onto a model of the patient's heart.

19. The system of claim 16, wherein the system is further configured to record or acquire at least one body surface signal from the patient using at least one body surface electrode, the at least one body surface signal being acquired or recorded simultaneously or substantially simultaneously with the recorded or acquired intra-cardiac signals.

20. The system of claim 19, wherein the system is further configured to isolate or extract at least one ventricular signal from the recorded or acquired body surface signal, and determine, using the extracted or isolated intra-cardiac and at least one body surface ventricular signals and the computing device, the locations of the electrodes inside the patient's heart that are associated with each isolated or extracted ventricular signal.

21. The system of claim 20, wherein the isolated or extracted ventricular signals comprise QRS complexes.

22. The system of claim 16, wherein the system is further configured to record or acquire intra-cardiac signals as the basket is moved inside the patient's atrium to different positions.

23. The system of claim 16, wherein the computing device is configured to remove low-frequency or other artefacts or noise from the recorded or acquired intra-cardiac and/or body surface signals.

24. The system of claim 16, wherein the computing device is configured to record or acquire a plurality of intra-cardiac signals for each electrode while the basket is in a given position within the patient's atrium, and to isolate or extract a ventricular signal for each such intra-cardiac signal.

25. The system of claim 16, wherein the computing device is further configured to determine changes in the three-dimensional locations and orientations of the basket and the electrodes thereof as the basket is moved around, in or near the patient's atrium or other heart chamber.

26. The system of claim 16, wherein the system further comprises a visual display operably connected to the computing device configured to provide a user such that the user can see the locations of the electrodes and/or basket inside or near the patient's atrium or other heart chamber.

27. The system of claim 16, further comprising at least one neural network configured to provide the locations of the electrodes and/or basket inside or near the patient's atrium or other heart chamber.

28. The system of claim 16, wherein the computing device and a display are configured to provide a visualization of locations of at least one of the electrodes and the basket inside or near the patient's atrium or other heart chamber to a user.

* * * * *